US009496502B2

(12) United States Patent
Pan et al.

(10) Patent No.: US 9,496,502 B2
(45) Date of Patent: Nov. 15, 2016

(54) ORGANIC IONIC COMPOUNDS, COMPOSITIONS AND ELECTRONIC DEVICES

(75) Inventors: Junyou Pan, Frankfurt am Main (DE); Amir Hossain Parham, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 342 days.

(21) Appl. No.: 14/117,049

(22) PCT Filed: Apr. 18, 2012

(86) PCT No.: PCT/EP2012/001671
§ 371 (c)(1),
(2), (4) Date: Nov. 12, 2013

(87) PCT Pub. No.: WO2012/152366
PCT Pub. Date: Nov. 15, 2012

(65) Prior Publication Data
US 2014/0249606 A1 Sep. 4, 2014

(30) Foreign Application Priority Data
May 12, 2011 (EP) .................................. 11003921

(51) Int. Cl.
*H01L 51/00* (2006.01)
*A61N 5/06* (2006.01)
*H01L 51/50* (2006.01)

(52) U.S. Cl.
CPC ......... *H01L 51/0058* (2013.01); *A61N 5/0616* (2013.01); *H01L 51/0052* (2013.01); *H01L 51/0067* (2013.01); *H01L 51/0085* (2013.01); *H01L 51/5032* (2013.01); *H01L 51/5016* (2013.01); *Y02E 10/549* (2013.01)

(58) Field of Classification Search
CPC ....................... H01G 9/2013; H01L 51/0032
See application file for complete search history.

(56) References Cited

U.S. PATENT DOCUMENTS

| 5,900,327 A * | 5/1999 | Pei .................. C08G 61/00 313/504 |
| 6,059,943 A * | 5/2000 | Murphy ............... C08J 5/2275 204/296 |
| 6,326,091 B1 * | 12/2001 | Schoo .................... C09K 11/06 257/40 |
| 6,853,472 B2 * | 2/2005 | Warner ................. C07C 311/48 252/500 |
| 9,172,049 B2 * | 10/2015 | Jenekhe ............... C07D 215/06 |
| 2005/0008896 A1 | 1/2005 | Imanishi et al. |
| 2007/0207341 A1 | 9/2007 | Iida et al. |
| 2007/0215865 A1 | 9/2007 | Liu et al. |
| 2007/0215879 A1 | 9/2007 | Liu et al. |

FOREIGN PATENT DOCUMENTS

| JP | 2005047892 A | 2/2005 |
| JP | 2006233162 A | 9/2006 |
| JP | 2008508985 A | 3/2008 |
| JP | 2009530847 A | 8/2009 |
| WO | WO-2006020602 A1 | 2/2006 |
| WO | WO-2007111763 A2 | 10/2007 |

OTHER PUBLICATIONS

Li et al., "Organic Light-Emitting Materials and Devices", 5 pages.
Chen, Fang-Chung, et al., "Phosphorescent Light-Emitting Electrochemical Cell", Applied Physics Letters, vol. 81, No. 22, (2002), pp. 4278-4280.
International Search Report for PCT/EP2012/001671 mailed May 22, 2012.

* cited by examiner

*Primary Examiner* — Evan Pert
(74) *Attorney, Agent, or Firm* — Drinker Biddle & Reath LLP

(57) ABSTRACT

The present invention relates inter alia to novel compositions, compounds and formulations of multi-charged organic cations or anions having a functional organic group or a non-functional organic group. The present invention further relates to devices comprising the these compositions, compounds or formulations.

20 Claims, No Drawings

ORGANIC IONIC COMPOUNDS, COMPOSITIONS AND ELECTRONIC DEVICES

RELATED APPLICATIONS

This application is a national stage application (under 35 U.S.C. §371) of PCT/EP2012/001671, filed Apr. 18, 2012, which claims benefit of European Application No. 11003921.1, filed May 12, 2011. Both are incorporated herein by reference in their entirety.

The present invention relates inter alia to a novel electronic device comprising a non-polymeric organic ionic compound comprising a multi-charged cation or anion having a functional organic group or a non-functional organic group, and one or more ion(s) as counter ion(s), preferably being as small that it may act as a mobile ion in films containing the organic ionic compound, characterized in that the said non-polymeric organic ionic compound comprises no metal-complex containing a transition metal. Furthermore, the present invention relates to an organic ionic compound comprising a multi-charged cation or anion having a functional organic group, and one or more ion(s) as counter ion(s) preferably being as small that it may act as a mobile ion in films containing the organic ionic compound, characterized in that the said non-polymeric organic ionic compound comprises no metal-complex containing a transition metal. Moreover, the present invention relates to a composition comprising an organic ionic compound according to the invention and another functional compound. The organic ionic compound or the composition may be used in organic devices as functional or non-functional materials. Further the present invention relates to a formulation comprising a ionic organic compound or a composition of the present invention. Furthermore, the present invention relates to the use of the compositions, compounds, formulations and/or devices according to the present invention in phototherapy for the treatment and/or prophylaxis of diseases and/or cosmetic conditions.

Organic electronic devices, such as organic light emitting diodes (OLEDs) have many advantages over their inorganic counterpart (light emitting diodes—LEDs) in that they are intrinsically flexible, and can be coated on large area by, for example, printing technologies, such as ink jet printing and screen printing.

However, in OLEDs active metals, such as Ba and Ca, are used as cathode. Oxygen and humidity can inhibit or destroy the function of OLEDs by attacking the cathode or organic functional layers. Therefore, OLEDs require excellent encapsulation to ensure long lifetime both in storage and in operation. An alternative device with a less sensitive cathode will ease the OLED production.

Further, in OLED, the functional layers, are usually very thin, typically less than 100 nm or even less than 50 nm. Moreover, these thin layers are required to be highly homogeneous, which is a still big challenge for printing technology even on a flat substrate, let alone if the surface is curved.

Moreover, the production of OLEDs with a multilayer structure, is still an elaborate and cost intensive task. In comparison to OLEDs, so called OLECs (organic light emitting electrochemical cells) are much simpler, typically consisting only one or two functional layer sandwiched between two electrodes. And the emissive layer could be made much thicker than OLED. This leads to a wider process windows, and even makes it possible to adopt the established printing technology for OLEC production. Thus, the production costs in particular for mass production could be expected to be much lower as compared to the ones of OLEDs.

Furthermore, OLECs do not rely on air-sensitive charge-injection layers or metals such as Ba or Ca for electron injection, which further simplifies their preparation and makes them more cost efficient, as compared to OLEDs. This is due to the less stringent requirements for encapsulation of OLECs.

The underlying technology of OLECs differ from the one of OLEDs or LEDs. Both OLEDs and LEDs are diodes with forward bias and reverse bias. In contrast to OLECs the I-V (current-voltage) curves of both OLEDs and LEDs are asymmetric. They represent semiconductor technologies whereas an OLEC is basically an electrochemical or more precisely an electrolytic cell. Charge transport in OLEDs occurs via the movement of holes and electrons from molecule to molecule until holes and electrons recombine to form so called excitons, i.e. electron-hole-pairs. Light is emitted when excitons decay radiatively. In OLECs, upon applying a voltage, the electrolyte is oxidized at the anode and reduced at the cathode. The molecular cations and/or anions diffuse under the electrical field and in the meanwhile doping the organic emissive materials until they meet together to form a so called p-n junction. Further an exciton is formed on the organic emissive compounds in the p-n junction. The radiative decay of the exciton leads to the emission of light. The original work and the principle of OLECs can be referred to the paper by Qibing Pei et al., Science, 1995, 269, 1086-1088. The OLECs can, in principle, show symmetric I-V curves, have low driving voltages, and there is no need for active metals as cathode.

The second type of light emitting electrochemical device comprising ionic materials is a device with an ionic p-n junction as reported by Daniel A. Bernards, et al., Science 2008, 313, 1416, wherein two layers are laminated together. One of the layers has a mobile anion and the other one has a mobile cation; by ion exchange an ionic p-n junction is formed in the interface between two layers. Here the ionic p-n junction is formed before the voltage is applied. The emission of light can then occur in the p-n junction. A similar light emitting device was also disclosed in US 2007/0157662 A1.

The third type of light emitting electrochemical device is the so-called organic light emitting electrochemical transistors (OLEETs), as firstly reported by Yumusak et al., Appl. Phys. Lett. 97, 033302 (2010). The OLEET has the same device structure like organic field-effect transistor, having, source, drain and gate electrodes, but has a mixture of organic emissive material and ionic compound between source and drain.

Though, there are obviously advantages of electrochemical device over OLEDs, there is still a great demand to provide materials for organic light emitting electrochemical devices, such as OLECs in order to enhance performance, particularly life time and efficiency. This will be also beneficial for other organic electronic devices, for example organic solar cell, etc.

So far, most OLECs have been built with mono-salt, for example Lithium salts (for example lithium trifluoromethanesulfonate as reported by Qibing Pei et al., Science, 1995, 269, 1086-1088) and organic ionic compounds (for example methyltrioctylammonium trifluoromethanesulfonate (MATS) as reported by Jen et al., in Adv. Mater. 2009, 21, 1972-1975). All of them comprising one mobile mono-ion for example $Li^+$ and trifluoromethanesulfonate. Whereas, the only possible function of the counter ions is believed to induce the doping in the organic active materials.

Chen et al., reported very recently an OLEC containing double-charged fluorene trimer emitter in J. Chem. Mater, with DOI: 10.1039/c0jm03446k. However, the performance of the reported OLED is still far from good for application.

Objectives of the present invention are, thus, novel compositions comprising ionic compounds, ionic compounds, formulations, and electronic devices comprising the compositions and/or compounds.

The present invention relates to a composition comprising at least one non-polymeric organic ionic compound and at least one further compound which is a non-ionic organic functional compound, characterized in that the organic ionic compound has the following formula (1):

$$(M)^{m+/-}{}_y \times (N)^{n-/+} \quad \text{Formula (1);}$$

wherein the used symbols and indexes have the following meanings:

M is an organic ion having the charge m+ or m−;
N is an organic or inorganic counter ion being the same or different at each occurrence having the charge n− or n+;
m indicates the number of the charge of M and is an integer of ≥2;
y indicates the number of N, and is an integer of ≥1;
n indicates the number of the charge of N and is an integer of ≥1;
wherein the net charge of the compound of formula (1) is zero;
and wherein the said non-ionic organic functional compound is selected from the group consisting of host materials, phosphorescent emitters, fluorescent emitters, hole transporting materials (HTM), hole injecting materials (HIM), electron transporting materials (ETM), and electron injecting materials (EIM), preferably phosphorescent emitters, fluorescent emitters and host materials.

Preferably the composition comprises 3, particularly preferably 2 and very particularly preferably 1 non polymeric organic ionic compounds of formula (1).

Preference is given to a composition according top the present invention comprising one non polymeric organic ionic compound of formula (1) and 4, preferably 3, particularly preferably 2, and very particularly preferably 1 further non-ionic organic functional compound selected from host materials, phosphorescent emitters, fluorescent emitters, hole transporting materials (HTM), hole injecting materials (HIM), electron transporting materials (ETM), and electron injecting materials (EIM), preferably phosphorescent emitters, fluorescent emitters and host materials.

Organic functional groups or compounds can be characterized by their molecular frontier orbitals, i.e. the highest occupied molecular orbital (HOMO) (sometimes also referred to as valence band) and the lowest unoccupied molecular orbital (LUMO)(sometimes also referred to as conduction band). The HOMO and LUMO levels are routinely measured (by e.g. XPS=X-ray photoelectron spectroscopy, UPS=ultra-violet photoelectron spectroscopy or CV=cyclovoltammetry) or calculated (by quantum chemical methods such as (time dependent) DFT=density functional theory) which are known to the person skilled in the art. One skilled in the art is also aware of the fact that absolute values of these energy levels significantly depend on the method used. The reliable comparison of HOMO and LUMO energy levels of organic functional materials requires the employment of the same measurement method or calculation method.

The said further non-ionic organic functional compound may be selected from small molecules, polymers, oligomers, or dendrimers, blends or mixtures thereof.

The term small molecule as used herein is defined as molecules being not a polymer, oligomer, dendrimer, or a blend. Small molecule in the context of the present invention is a monomeric or dimeric compound. In particular, repeating structures are absent in small molecules. The molecular weight of small molecules is typically in the range of polymers with a low number of repeating units, oligomers or less.

The molecular weight of the small molecule is preferably below 5000 g/mol, particularly preferably below 4000 g/mol, and very particularly preferably below 3000 g/mol.

Further polymer and oligomer, preferably neutral, can also be mixed with the compound according to formula (1). Th oligomer possibly be used in this invention have preferably 3 to 9 repeat units. The branching index of the oligomers is between 0 (linear oligomer without branching) and 1 (completely branched dendrimer). The term dendrimer as used herein is defined according to M. Fischer et al. in Angew. Chem., Int. Ed. 1999, 38, 885). The molecular weight of oligomer or dendrimer suitable for the present invention can be from 3000 g/mol to 10000 g/mol, preferably below 8000 g/mol, very preferably below 7000 g/mol.

The polymers in the context of the invention preferably have 10 to 10000, particularly preferably 20 to 5000 and very particularly preferably 50 to 2000 repeat units. The molecular weight MW of the polymers is preferably in the range of 10000 to 2000000 g/mol, particularly preferably in the range of 100000 to 1500000 g/mol, and very particularly preferably in the range of 200000 to 1000000 g/mol. The determination of MW can be performed according to standard techniques known to the person skilled in the art by employing gel permeation chromatography (GPC) with polystyrene as internal standard, for instance.

If said composition comprises at least one ionic compound according to formula (1) and at least one non-ionic host (matrix) material, the weight ratio of the ionic compound and the host material can be from 1:10 to 10:1, preferably from 1:8 to 8:1, particularly preferably from 1:4 to 4:1, and very particularly preferably from 1:2 to 2:1.

If said composition comprises at least one ionic compound according to formula (1) and at least one non-ionic EIM and/or ETM, the ionic compound has a concentration from 1 to 99 wt %, preferably from 10 to 90 wt %, particularly preferably from 20 to 80 wt %, and very particularly preferably from 30 to 70 wt %.

If said composition comprises at least one ionic compound according to formula (1) and at least one non-ionic HIM and/or HTM, the ionic compound has a concentration from 1 to 99 wt %, preferably from 10 to 90 wt %, particularly preferably from 20 to 80 wt %, and very particularly preferably from 30 to 70 wt %.

Further preference is given to a composition according to the present invention comprising an non-ionic fluorescent and/or non-ionic phosphorescent emitter and a non-ionic host material.

The term "host material" as used herein can be both a host material for fluorescent emitters and a host material for phosphorescent emitters (also referred to as matrix or matrix material).

It is furthermore preferred that the composition according to the present invention comprises a host (matrix) compound or host (matrix) group and a fluorescent or phosphorescent emitter compound. The before mentioned host (matrix) group is thereby meant as (a part of the) ion M of the organic ionic compound according to formula (1), whereas the host (matrix) compound is a separate compound, which is the non-ionic organic functional material. The concentration of the fluorescent emitter can be from 1 to 20 wt %, preferably from 2 to 15 wt %, and particularly preferably from 3 to 10 wt %, and very particularly preferably from 3 to 8 wt %. The concentration of the phosphorescent emitter can be from 1 to 30 wt %, preferably from 2 to 25 wt %, and particularly preferably from 5 to 20 wt %, and very particularly preferably from 10 to 20 wt %.

The composition according to the invention is preferably one wherein the function of the functional organic group of the ion M of the organic ionic compound according to the invention is different from the function of the non-ionic functional organic compound. It is, however, conceivable that both have the same function.

The compound according to formula (1) in said composition may either be a non-functional or a functional material. In the most simple case the multi-charged organic cation or anion M in compound of formula (1) is consisting of the functional or non functional organic group which itself is a multi-charged compound. In another case the multi-charged organic cation or anion M in compound of formula (1) comprises at least two groups, namely the functional or non-functional organic group and one or more charged groups.

In the following many organic functional molecules or materials are listed which can serve as fluorescence emitter, phosphorescence emitter, host (matrix) material, EIM, ETM, HIM, and HTM, for instance. If these compounds are non-ionic in nature they can be used as non-ionic organic functional material for the compositions according to the present invention. Based on the non-ionic compounds given below, however, also ionic compounds suitable to be included in M of formula (1) can be built in different ways. One typical way is to replace one or more hydrogen atom of an non-ionic organic functional or non-functional compounds by a charged group. Examples for charged groups are —$SO_3^-$, —$O^-$, —$S^-$, —$NO_2^-$, —$NO_3^-$, —$NH_4^+$. The more suitable charged groups will be described below. Suitable charged groups can be selected from anions or cations groups described below for N in formula (1).

Since the ionic compound of formula (1) provides more than one charge, it is possible to have either counter ions having more than one charge or having more than one counter ions within the compound. In both cases the charge density is higher than in salts having only monovalent ions. Furthermore, the multi-charged ion induces higher local electrical field in the films, which may be of benefit to doping or other processes involved in the electronic device. One of two effects, or both may be, at least in part, the reason for the improved performance of electronic devices according to the present invention as will be shown in the example section below.

The scope of functional organic group in the context of the present invention includes the groups selected from a fluorescence or phosphorescence emitting group, a matrix/host group, a hole injection group, a hole transport group, a hole blocking group, an electron injection group, an electron transport group, an electron blocking group and a dye.

In case the organic ion M comprises a non functional group the organic ion M is a non functional compound. The term "non functional" used herein is meant in that the groups or compounds characterized by that term are different from a fluorescence or phosphorescence emitting group/compound, a matrix group/compound, a hole injection group/compound, a hole transport group/compound, a hole blocking group/compound, an electron injection group/compound, an electron transport group/compound, and electron blocking group/compound or a dye. That is, the non functional group/compound according to the invention is a group having no functions as emitter, host/matrix, hole injection/transport/blocking, electron injection/transport/blocking, or dye. The non functional group/compound is present since then the organic ion M is only a divalent cation or anion providing more than one charge.

In one preferred embodiment, said composition comprises at least one compound of formula (1), wherein M comprises a non functional group or is itself a non functional compound.

In another preferred embodiment, said composition comprises at least one compound of formula (1), wherein M comprises a functional group or is itself a functional compound.

The terms fluorescent emitter refers to a material which, upon receiving excitonic energy by any kind of energy transfers from other materials, or by forming an exciton either electrically or optically, undergoes radiative decay to emit light. The term fluorescent emitter relates to materials or compounds which undergo a radiative transition from an excited singlet state to its ground state. The term phosphorescent emitter, may also be used hereafter, relates to luminescent materials or compounds which comprise transition metals. This typically includes materials emitting light caused by spin forbidden transition(s), e.g., transitions from excited triplet and/or quintet states.

Preferred fluorescent emitter compounds are selected from polyaromatic compounds, such as, for example, 9,10-di(2-naphthylanthracene) and other anthracene derivatives, derivatives of tetracene, xanthene, perylene, such as, for example, 2,5,8,11-tetra-t-butylperylene, phenylene, for example 4,4'-(bis(9-ethyl-3-carbazovinylene)-1,1'-biphenyl, fluorene, aryl-pyrenes (US 2006/0222886), arylenevinylenes (U.S. Pat. No. 5,121,029, U.S. Pat. No. 5,130,603), derivatives of rubrene, coumarine, rhodamine, quinacridone, such as, for example, N,N'-dimethylquinacridone (DMQA), dicyano-methylenepyrane, such as, for example, 4 (dicyanoethylene)-6-(4-dimethyl-aminostyryl-2-methyl)-4H-pyrane (DCM), thiopyrans, polymethine, pyrylium and thiapyrylium salts, periflanthene, indenoperylene, bis(azinyl) imine-boron compounds (US 2007/0092753 A1), bis(azinyl) methene compounds and carbostyryl compounds.

Further preferred fluorescent emitter compounds can be referred to non-polymeric fluorescent emitter described in C. H. Chen et al.: "Recent developments in organic electroluminescent materials" Macromol. Symp. 125, (1997), 1-48 and "Recent progress of molecular organic electroluminescent materials and devices" Mat. Sci. and Eng. R, 39 (2002), 143-222.

Preferred fluorescent emitter compounds are selected from the class of the monostyrylamines, the distyrylamines, the tristyrylamines, the tetrastyrylamines, the styrylphosphines, the styryl ethers and the arylamines.

A monostyrylamine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. The corresponding phosphines and ethers are defined analogously to the amines. For the purposes of this invention, an arylamine or an aromatic amine is taken to mean a compound which contains three substituted or unsubstituted aromatic or heteroaromatic ring systems bonded directly to the nitrogen. At least one of these aromatic or heteroaromatic ring systems is preferably a condensed ring system, preferably having at least 14 aromatic ring atoms. Preferred examples thereof are aromatic anthracene-amines, aromatic anthracene-diamines, aromatic pyrene-amines, aromatic pyrene-diamines, aromatic chrysene-amines and aromatic chrysene-diamines. An aromatic anthracene-amine is taken to mean a compound in which one diarylamino group is bonded directly to an anthracene group, preferably in the 9 position. An aromatic anthracene-diamine is taken to mean a compound in which two diarylamino groups are bonded directly to an anthracene group, preferably in the 9,10-position. Aromatic pyrene-amines, pyrene-diamines, chrysene-amines and chrysene-diamines are defined analogously thereto, where the diarylamino groups on the pyrene are preferably bonded in the 1 position or in the 1,6-position.

Further preferred fluorescent emitter compounds are selected from indenofluorene-amines and indenofluorene-diamines, for example in accordance with WO 2006/122630, benzoindenofluorene-amines and benzoindenofluorene-diamines, for example in accordance with WO 2008/006449, and dibenzoindenofluorene-amines and dibenzoindeno-fluorene-diamines, for example in accordance with WO 2007/140847.

Examples of fluorescent emitter compounds from the class of the styrylamines are substituted or unsubstituted tristilbene-amines or the dopants described in WO 2006/000388, WO 2006/058737, WO 2006/000389, WO 2007/065549 and WO 2007/115610. Distyryl-benzene and distyrylbiphenyl derivatives are described in U.S. Pat. No. 5,121,029. Further styrylamines are found in US 2007/0122656 A1.

Particularly preferred styrylamine dopants and triarylamine dopants are the compounds of the formulae (2) to (7) and as disclosed in U.S. Pat. No. 7,250,532 B2, DE 102005058557 A1, CN 1583691 A, JP 08053397 A, U.S. Pat. No. 6,251,531 B1, and US 2006/210830 A.

Formula (2)

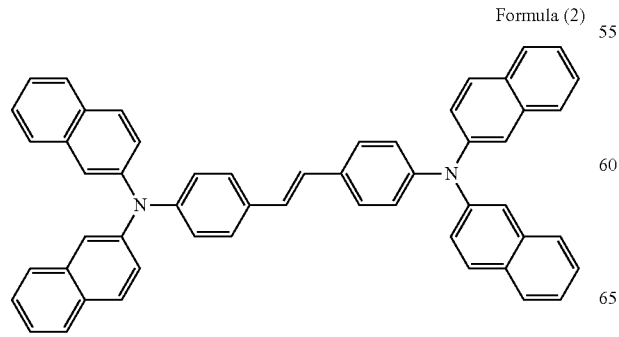

Formula (3)

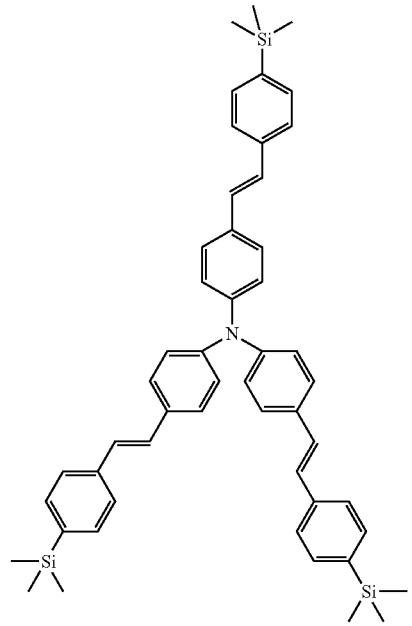

Formula (4)

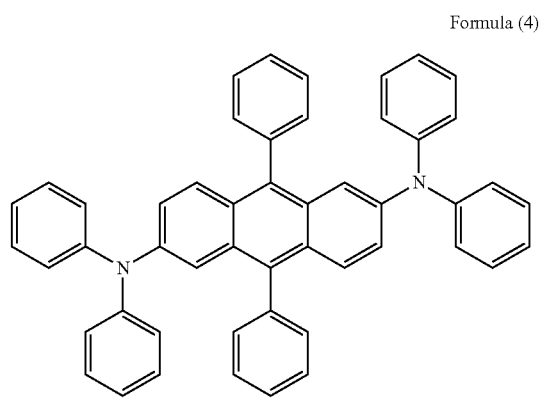

Formula (5)

Formula (6)

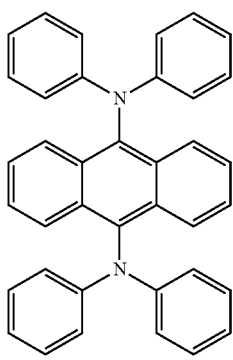

Formula (7)

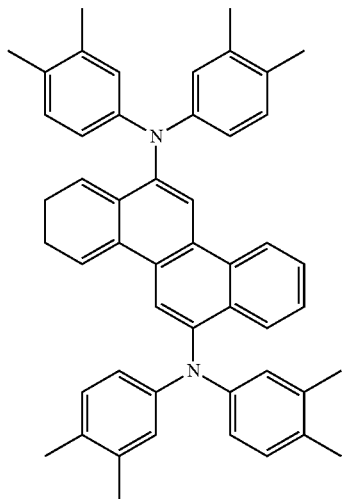

Further preferred fluorescent emitter compounds are selected from the group of triarylamines as disclosed in EP 1957606 A1 and US 2008/0113101 A1.

Further preferred fluorescent emitter compounds are selected from derivatives of naphthalene, anthracene, tetracene, fluorene, periflanthene, indenoperylene, phenanthrene, perylene (US 2007/0252517 A1), pyrene, chrysene, decacyclene, coronene, tetraphenylcyclopentadiene, pentaphenylcyclopentadiene, fluorene, spirofluorene, rubrene, coumarine (U.S. Pat. No. 4,769,292, U.S. Pat. No. 6,020,078, US 2007/0252517 A1), pyran, oxazone, benzoxazole, benzothiazole, benzimidazole, pyrazine, cinnamic acid esters, diketopyrrolopyrrole, acridone and quinacridone (US 2007/0252517 A1).

As of the anthracene compounds, particular preference is given to 9,10-substituted anthracenes, such as, for example, 9,10-diphenylanthracene and 9,10-bis(phenylethynyl)anthracene. 1,4-Bis(9′-ethynylanthracenyl)-benzene is also a preferred fluorescence emitter compound.

In case the above mentioned examples of fluorescence emitter compounds are ionic compounds they may act as the multi-charged organic cation or anion M itself. In this case M is consisting of the functional organic group and the functional organic group itself is M.

In this case the ionic compound of formula (1) can be obtained by replacing at least one hydrogen atom in the above described fluorescent emitters by a charged group. In this case the fluorescence emitter compounds are the above-mentioned functional organic group comprised in the multi-charged organic cation or anion M and are bound to the charged parts of M in that at least one hydrogen atom is not present in the above mentioned compounds and the compounds are connected to the charged parts of M via the positions where the hydrogen atoms are not present.

Examples for suitable multicharged cation or anion comprising a fluorescent emitter group are listed as follows. Further suitable examples can be readily made by the combination of the fluorescent emitter groups as described above and the anion and cation groups as described below.

Formula (8)

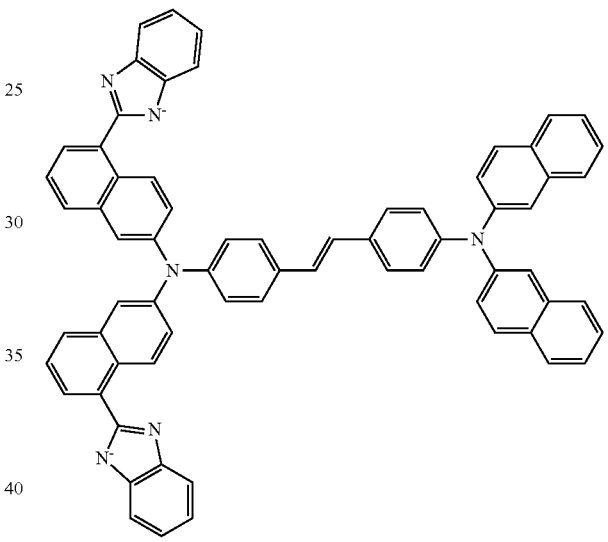

Formula (9)

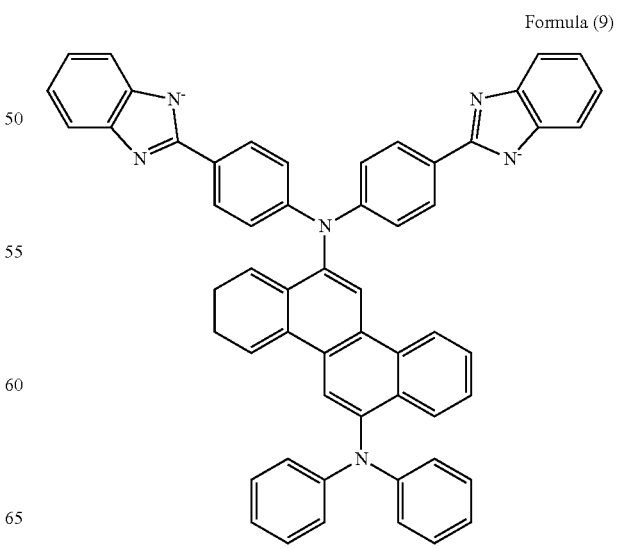

Formula (10)
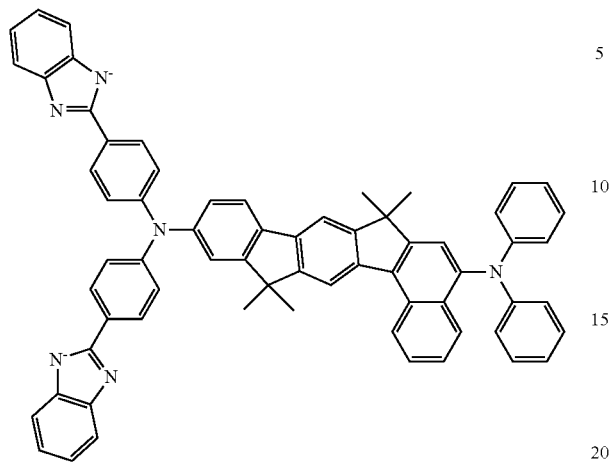
Formula (11)
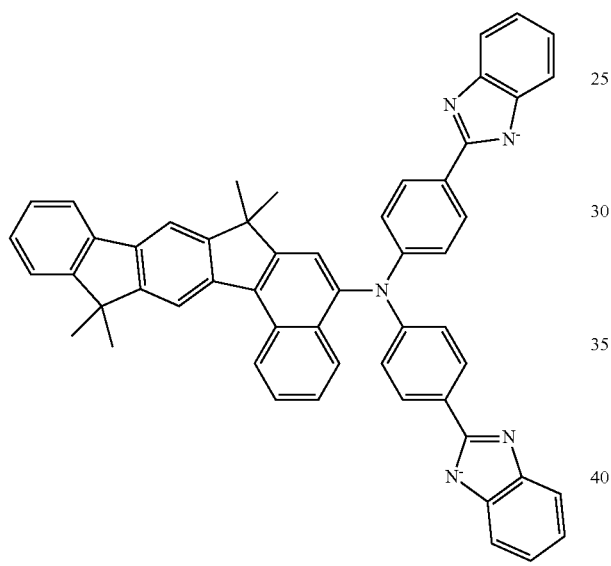
Formula (12)
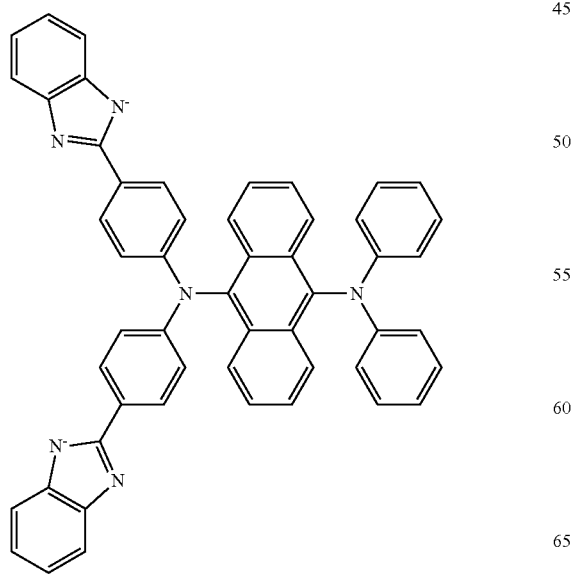
Formula (13)
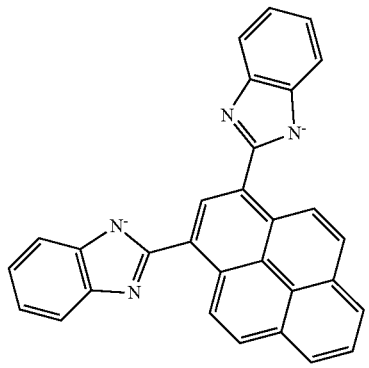
Formula (14)
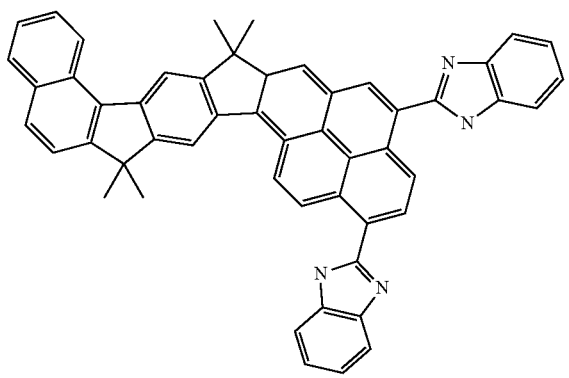
Formula (15)
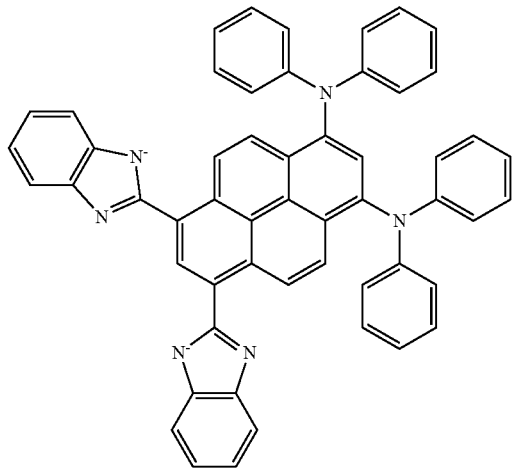

Formula (16)
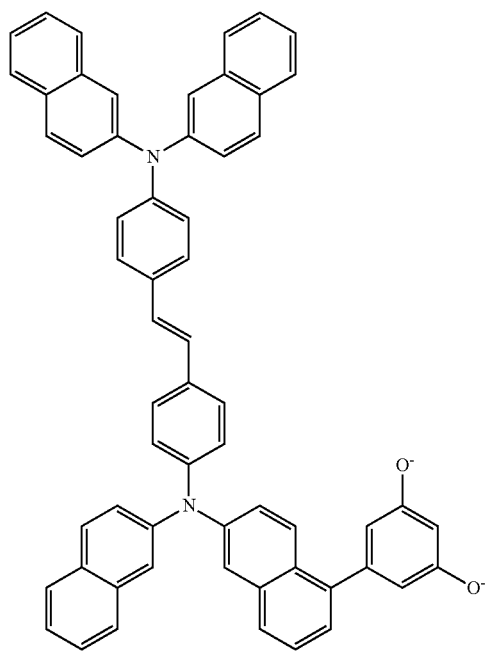
Formula (17)
Formula (18)
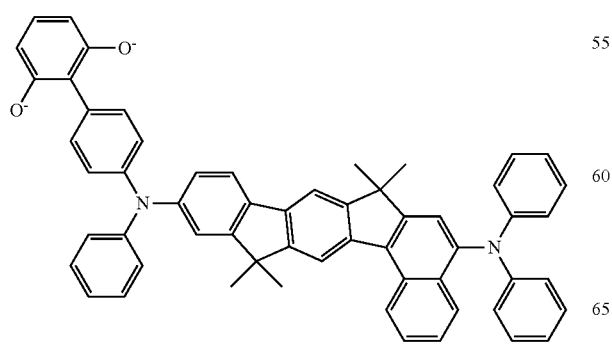
Formula (19)
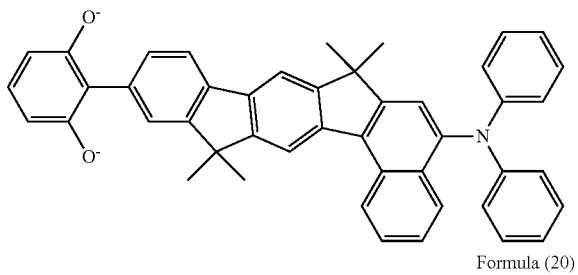
Formula (20)
Formula (21)
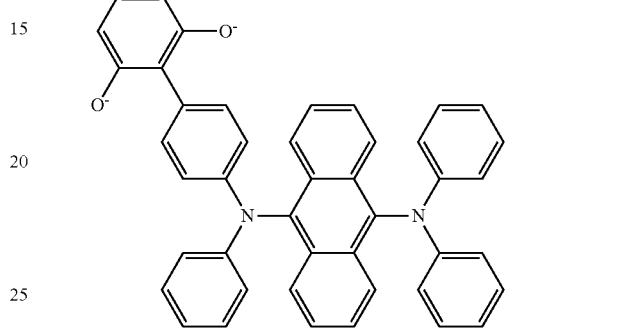
Formula (22)
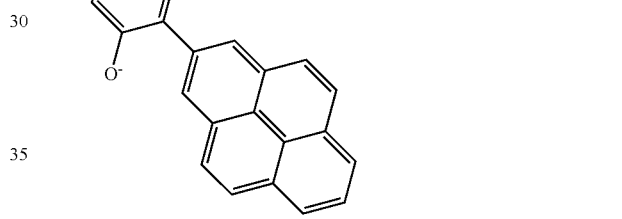
Formula (23)
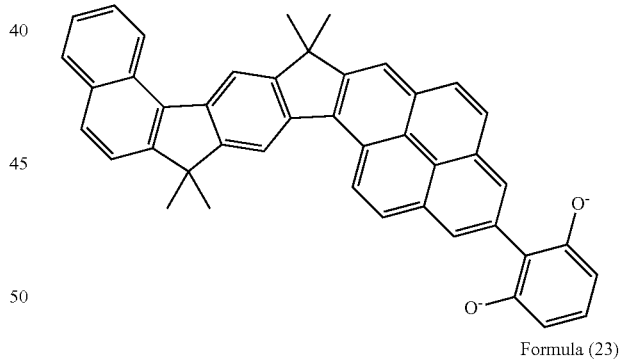
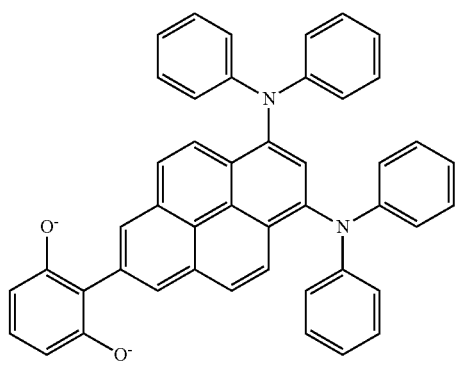

-continued
Formula (24)
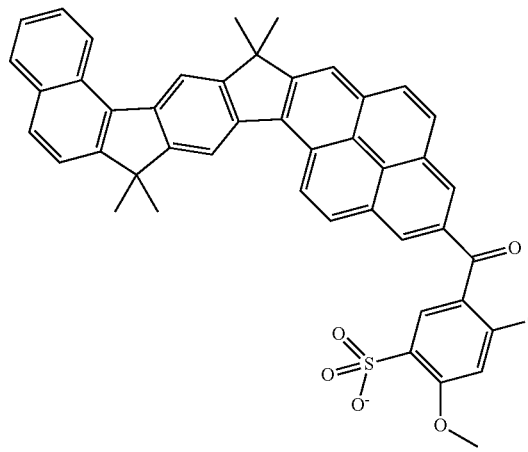
Formula (25)
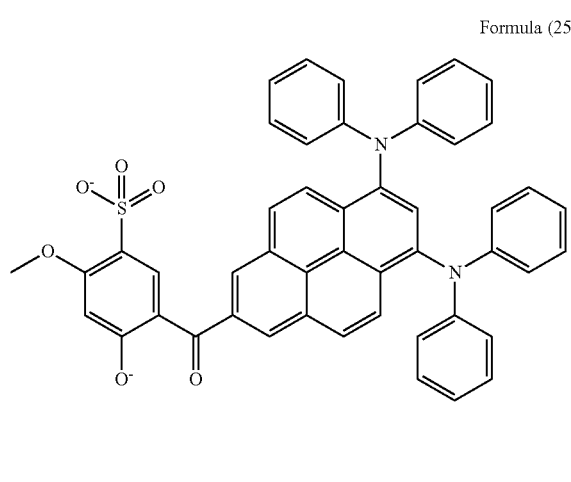
Formula (26)
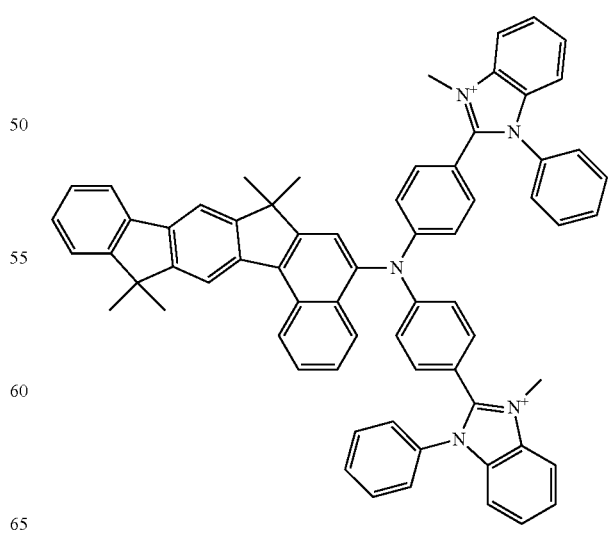
Formula (27)
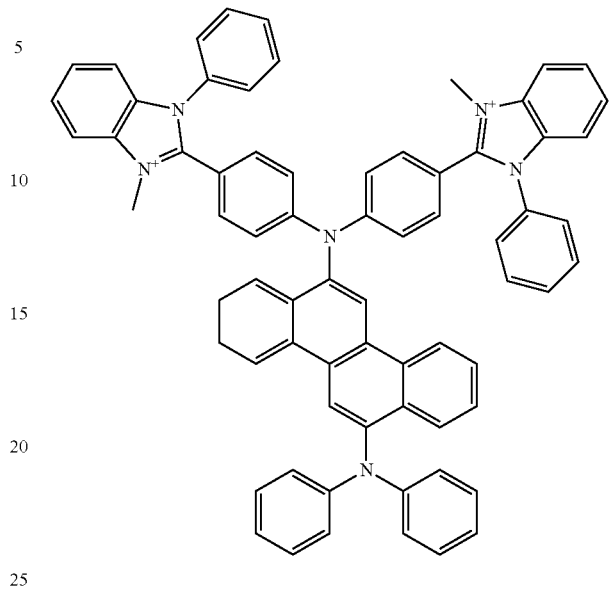
Formula (28)
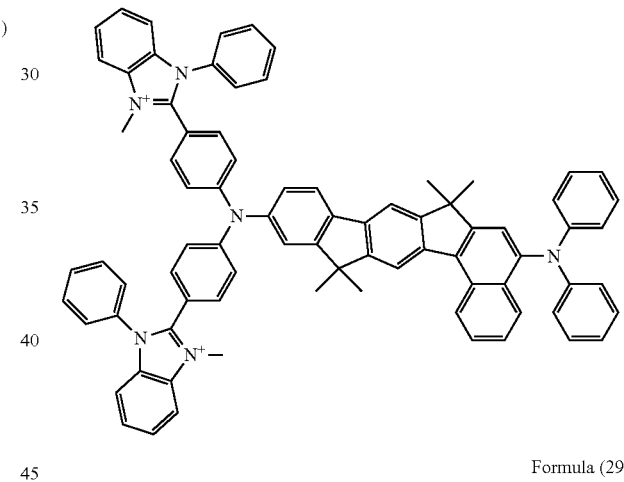
Formula (29)
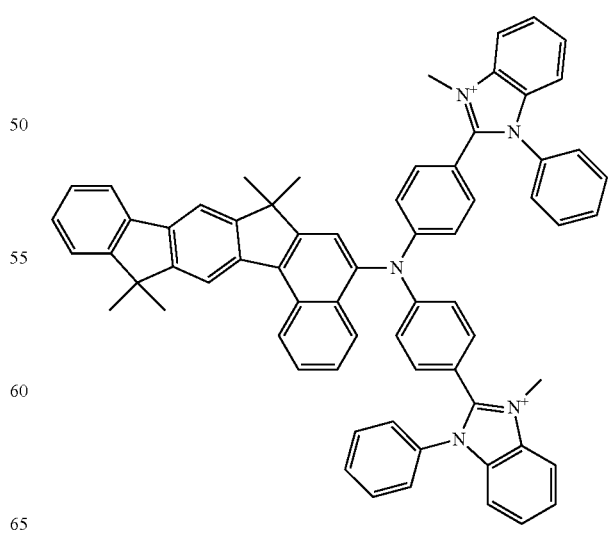

Formula (30)
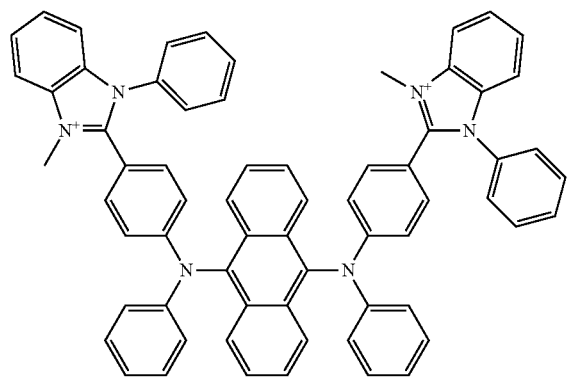
Formula (31)
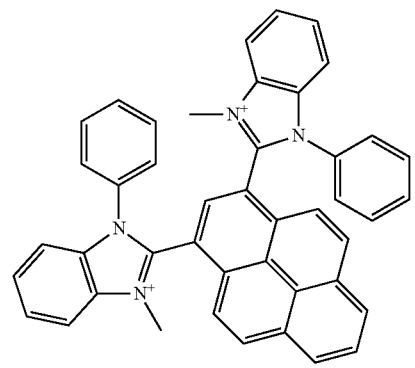
Formula (32)
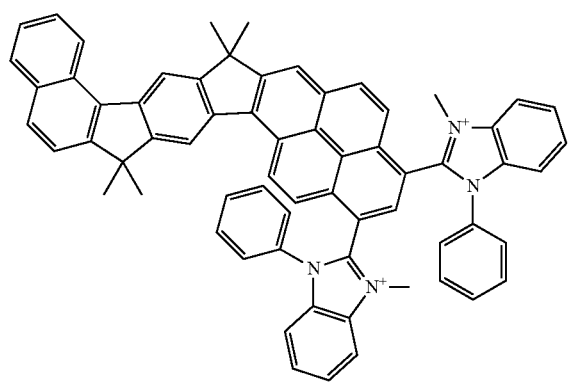
Formula (33)
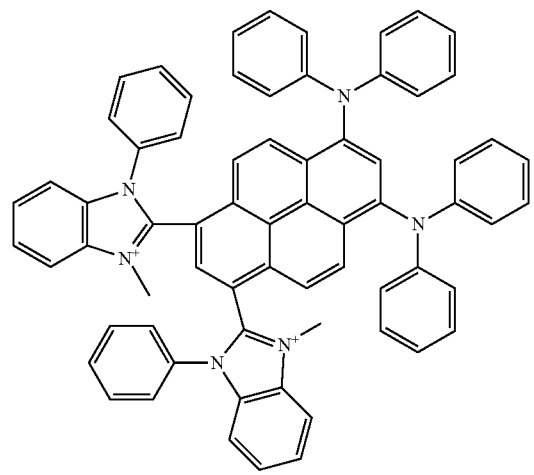
Formula (34)
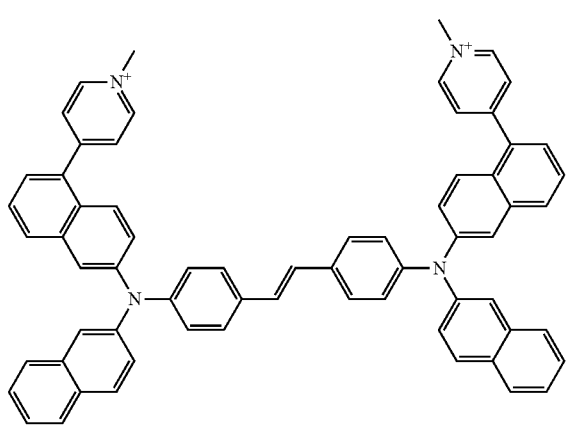
Formula (35)
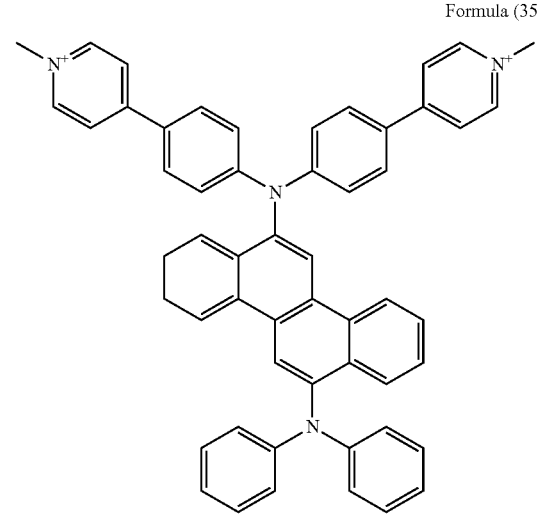
Formula (36)
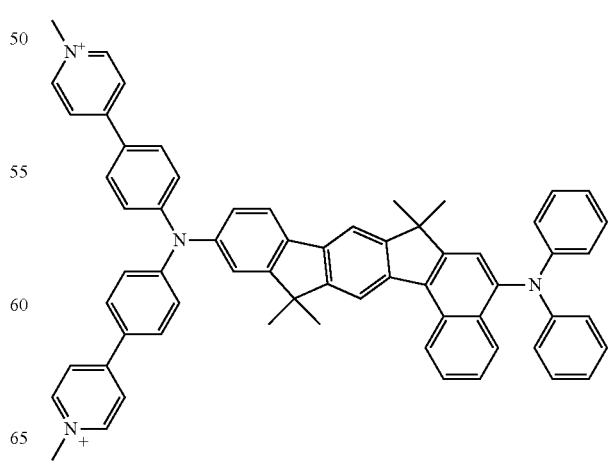

Formula (37)

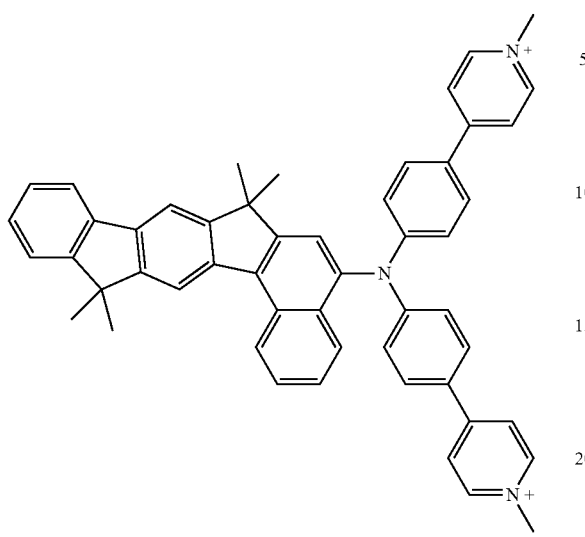

Formula (38)

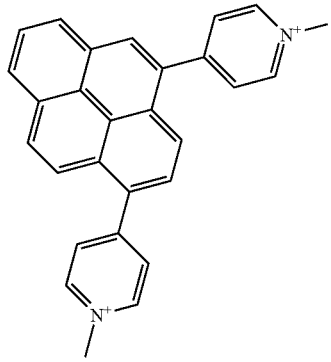

Formula (39)

Formula (40)

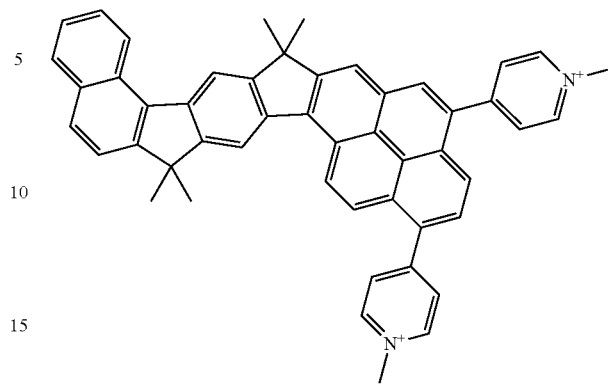

Formula (41)

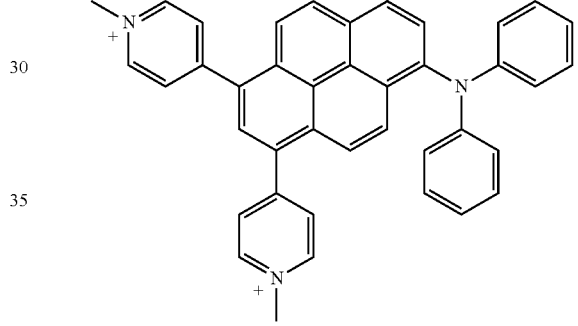

A general synthesis route for obtaining such compounds is provided below.

Further phosphorescent emitter which can be employed in said compositions as non-ionic organic functional material are disclosed in WO 00/70655, WO 01/41512, WO 02/02714, WO 02/15645, EP 1191613, EP 1191612, EP 1191614 and WO 2005/033244. In general, all phosphorescent complexes as used in accordance with the prior art for phosphorescent compounds used in electroluminescent devices and as are known to the person skilled in the art in the area of organic electroluminescence are suitable, and the person skilled in the art will be able to use further phosphorescent complexes without inventive step.

The phosphorescent emitter compound may be a metal complex, preferably with the formula $M(L)_z$, wherein M is a metal atom, L is in each occurrence independently of one another an organic ligand that is bonded to or coordinated with M via one, two or more positions, and z is an integer $\geq 1$, preferably 1, 2, 3, 4, 5 or 6, and wherein, optionally, these groups are linked to a polymer via one or more, preferably one, two or three positions, preferably via the ligands L.

M is in particular a metal atom selected from transition metals, preferably selected from transition metals of group VIII, or lanthanoides, or actinides, particularly preferably selected from Rh, Os, Ir, Pt, Pd, Au, Sm, Eu, Gd, Tb, Dy, Re, Cu, Zn, W, Mo, Pd, Ag, or Ru, and very particularly preferably selected from Os, Ir, Ru, Rh, Re, Pd, or Pt. M may also be Zn.

According to quantum mechanics with respect to metal complexes the transition from excited states with high spin multiplicity, e.g. from excited triplet states, to ground state is forbidden. However, the existence of an heavy atom, for example iridium, osmium, platinum and europium, results in a strong spin-orbit coupling, i.e. the excited singlet and triplet are mixed so that triplet gains some singlet character; and if singlet-triplet mixing yields a radiative decay rate faster than the non-radiative event, then the luminance can be efficient. This kind of emission can be achieved using metal complex, as firstly reported by Baldo et al.; Nature 395, 151-154 (1998).

Preferred ligands of the metal complexes used as phosphorescent emitter compound are 2 phenylpyridine derivatives, 7,8-benzoquinoline derivatives, 2 (2-thienyl)pyridine derivatives, 2 (1-naphthyl)pyridine derivatives or 2 phenylquinoline derivatives. All these compounds may be substituted, for example by fluoro- or trifluoromethyl substituents for blue emission. Auxiliary ligands are preferably acetylacetonate or picric acid.

In particular, complexes of Pt or Pd with tetradentate ligands of the formula (42) as disclosed in US 2007/0087219 A1, wherein $R^1$ to $R^{14}$ and $Z^1$ to $Z^5$ are as defined in the reference, Pt porphyrin complexes having an enlarged ring system (US 2009/0061681 A1) and Ir complexes are suitable, for example 2,3,7,8,12,13,17,18-octaethyl-21H, 23H-porphyrin-Pt(II), tetraphenyl-Pt(II)-tetrabenzoporphyrin (US 2009/0061681 A1), cis-bis(2-phenylpyridinato-N,C2') Pt(II), cis-bis(2-(2'-thienyl)pyridinato-N,C3')Pt(II), cis-bis (2-(2'-thienyl)quinolinato-N,C5')Pt(II), (2-(4,6-difluorophenyl)pyridinato-N,C2')Pt(II) acetylacetonate, or tris(2-phenylpyridinato-N,C2')Ir(III) (Ir(ppy)$_3$, green), bis(2-phenylpyridinato-N,C2)Ir(III) acetylacetonate (Ir(ppy)$_2$ acetylacetonate, green, US 2001/0053462 A1, Baldo, Thompson et al. Nature 403, (2000), 750-753), bis(1-phenylisoquinolinato-N,C2')(2-phenylpyridinato-N,C2')-iridium(III), bis(2-phenylpyridinato-N,C2')(1-phenylisoquinolinato-N,C2')iridium(III), bis(2-(2'-benzothienyl) pyridinato-N,C3')iridium(III) acetylacetonate, bis(2-(4',6'-difluorophenyl)pyridinato-N,C2')iridium(III) piccolinate (Firpic, blue), bis(2-(4',6'-difluorophenyl)pyridinato-N,C2') Ir(III) tetrakis(1-pyrazolyl)borate, tris(2-(biphenyl-3-yl)-4-tert-butylpyridine)-indium(III), (ppz)$_2$Ir(5phdpym) (US 2009/0061681 A1), (45ooppz)$_2$Ir(5phdpym) (US 2009/0061681 A1), derivatives of 2 phenyl-pyridine-Ir complexes, such as, for example, indium(III) bis(2-phenyl-quinolyl-N,C2')acetylacetonate (PQIr), tris(2-phenylisoquinolinato-N,C)Ir(III) (red), bis(2-(2'-benzo[4,5-a]thienyl)pyridinato-N,C3)Ir acetylacetonate ([Btp2Ir (acac)], red, Adachi et al. Appl. Phys. Lett. 78 (2001), 1622-1624).

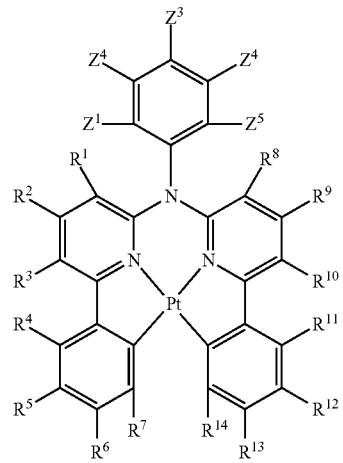

Formula (42)

Also suitable are complexes of trivalent lanthanides, such as, for example, $Tb^{3+}$ and $Eu^{3+}$ (J. Kido et al. Appl. Phys. Lett. 65 (1994), 2124, Kido et al. Chem. Lett. 657, 1990, US 2007/0252517 A1), or phosphorescent complexes of Pt(II), Ir(I), Rh(I) with maleonitrile dithiolate (Johnson et al., JACS 105, 1983, 1795), Re(I) tricarbonyl diimine complexes (Wrighton, JACS 96, 1974, 998 inter alia), Os(II) complexes with cyano ligands and bipyridyl or phenanthroline ligands (Ma et al., Synth. Metals 94, 1998, 245) or Alq$_3$ without a host.

Further phosphorescent emitter compounds with tridentate ligands are described in U.S. Pat. No. 6,824,895 and U.S. Pat. No. 7,029,766. Red-emitting phosphorescent complexes are mentioned in U.S. Pat. No. 6,835,469 and U.S. Pat. No. 6,830,828.

A particularly preferred phosphorescent emitter compound is a compound with the formula (43) and further compounds as disclosed, e.g., in US 2001/0053462 A1.

A particularly preferred phosphorescent emitter compound is a compound with the formula (44) and further compounds as disclosed, e.g., in WO 2007/095118 A1

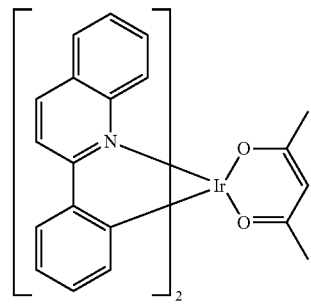

Formula (43)

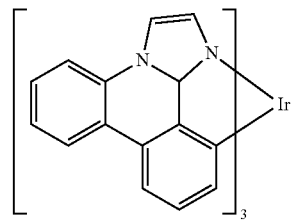

Formula (44)

Further derivatives of metal complexes are described in U.S. Pat. No. 7,378,162 B2, U.S. Pat. No. 6,835,469 B2, and JP 2003/253145 A.

Further preference is given to phosphorescent emitter compounds selected from carbene triple emitter, particularly to carbine complexes comprising iridium as metal. Preferred complexes are N-heterocyclic carbine (NHC) iridium complexes as disclosed in WO 2005/091373, WO 2005/113704, and in P. Erk et al., SID 2006, 11, 2, 131, e.g. fac-Ir(dpbic)$_3$, Ir(pmbic)$_3$, Ir(pmic)$_3$, Ir(dpnic)$_3$, Ir(cn-pmic)$_3$.

Further to metal complex mentioned elsewhere herein, a suitable metal complex according to the present invention can be selected from transition metals, rare earth elements, lanthanides and actinides. Preferably the metal is selected from Ir, Ru, Os, Eu, Au, Pt, Cu, Zn, Mo, W, Rh, Pd, or Ag.

In another embodiment according to the invention the functional organic group is a host or matrix group. In this case the multi-charged organic cation or anion M acts as a so called (co)-host or (co-)matrix material. That is, the matrix group gives the organic ionic compound of formula (1) the function of a host or matrix material for other materials acting as a guest in the matrix formed by the host material.

In organic electroluminescent devices, host materials are usually materials used in combination with emitter compounds being the guest in the host/matrix and have, in general, larger energy gaps between the HOMO and the LUMO as compared to emitter materials. In addition, host materials may preferably have either electron or hole transport property. Host materials can also have both electron and hole transport properties. In the case fluorescence emission is predominantly responsible for photoluminescence in an electroluminescent device, a maximal overlap between the absorption spectrum of the emitter with the photoluminescence spectrum of the host material is desired. This may ensure the energy transfer from host to emitter.

As mentioned above the term host material is also used for matrix or matrix material, particularly if a host is meant which is used in combination with a phosphorescent emitter.

In the present invention the host/matrix material is preferably selected any host, or matrix materials suitable for OLEDs. Preferably the suitable host/matrix group is selected from ketones, carbazoles, triarylamines, indolocarbazole, indenofluorenes, indenocarbazoles, fluorenes, spirobifluorenes, phenanthrenes, dihydrophenanthrenes, thiophenes, benzothiophene, dibenzothiophene, triazines, phosphine oxides, sulfoxides, sulfones, triazole, oxazole, imidazole azacarbazole, oligophenylenes, silanes, azaborole, diazaphosphole, polyaryl alkanes, pyrazoline, pyrazolone, distyryl pyrazine, thiopyrane dioxide, phenylene diamine, tertiary aromatic amines, styryl amines, amino-substituted chalcones, indole, hydrazone, stilbene, silazanes derivatives, aromatic dimethylidene compounds, anthracenes, benzanthracene, fluorene, spirobifluorene, phenanthrene, dihydrophenanthrene, isomers and derivatives thereof.

Preferred host materials suitable for fluorescent emitter compounds are selected from anthracene, benzanthracene, indenofluorene, fluorene, spirobifluorene, phenanthrene, dehydrophenanthrene, thiophene, triazine, imidazole, indolocarbazole, indenocarbazoles, stilbene, phenylene diamine, tertiary aromatic amine, styrylamine, and derivatives thereof.

Further examples for host materials for fluorescent emitter compounds are selected from the classes of the oligoarylenes (for example 2,2'7,7'-tetra-phenylspirobifluorene in accordance with EP 676461 or dinaphthylanthra-cene), in particular the oligoarylenes containing condensed aromatic groups, such as, for example, phenanthrene, tetracene, coronene, chrysene, fluorene, spirofluorene, perylene, phthaloperylene, naphthalo-perylene, decacyclene, rubrene, the oligoarylenevinylenes (for example 4,4'-bis(2,2-diphenylethenyl)-1,1'-biphenyl (DPVBi) or 4,4-bis-2,2-diphenyl-vinyl-1,1-spirobiphenyl (spiro-DPVBi) in accordance with EP 676461), the polypodal metal complexes (for example in accordance with WO 2004/081017), in particular metal complexes of 8 hydroxyquinoline, for example aluminium(III) tris(8-hydroxyquinoline) (aluminium quinolate, Alq$_3$) or bis(2-methyl-8-quinolinolato)-4-(phenylphenolinolato)aluminium, also with imidazole chelate (US 2007/0092753 A1) and quinoline-metal complexes, aminoquinoline-metal complexes, benzoquinoline-metal complexes, the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (e.g. DE 102007024850). Particularly preferred host materials are selected from the classes of the oligoarylenes, containing naphthalene, anthracene, benzanthracene and/or pyrene, or atropisomers of these compounds, the ketones, the phosphine oxides and the sulfoxides. Very particularly preferred host materials are selected from the classes of the oligoarylenes, containing anthracene, benzanthracene and/or pyrene, or atropisomers of these compounds. For the purposes of this invention, an oligoarylene is intended to be taken to mean a compound in which at least three aryl or arylene groups are bonded to one another.

Further preferred host materials preferably for fluorescent emitter compounds are selected, in particular, from compounds of the formula (45)

$$Ar^4—(Ar^5)_p—Ar^6 \quad \text{Formula (45)}$$

wherein $Ar^4$, $Ar^5$, $Ar^6$ are on each occurrence, identically or differently, a mono- or polycyclic aromatic or heteroaromatic ringsystem, which may be substituted by one or more radicals and p is 1, 2 or 3, the sum of the π-electrons in $Ar^4$, $Ar^5$ and $Ar^6$ is at least 30 if p=1 and is at least 36 if p=2 and is at least 42 if p=3.

A mono- or polycylic aromatic ringsystem is a ring system having 6 to 60 aromatic carbon atoms, more preferred 6 to 30, even more preferred 6 to 10 carbon atoms. A mono- or polycylic heteroaromatic ringsystem is a ring system having 5 to 60 aromatic ring atoms, more preferred 5 to 30 and even more preferred 5 to 14 ring atoms. The heteroaromatic ringsystem contains at least one heteroatom selected from N, O and S (the remaining atoms are carbon).

Preferred aromatic ring system are for instance phenyl, naphthyl, anthracyl, phenanthryl, dihydrophenanthryl, pyrene, dihydropyrene, chrysene, perylene, tetracene, pentacene, benzpyrene, fluorene and indene.

Preferred heteroaromatic ringsystems are for instance 5-membered rings, such as pyrrole, pyrazole, imidazole, 1,2,3-triazole, 1,2,4-triazole, tetrazole, furane, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, chinoxalinimidazole, benzoxazole, naphthoxazole, anthroxazole, phenanthroxazole, isoxazole, benzothiazole, benzofurane, isobenzofurane, dibenzofurane, chinoline, isochinoline, pteridine, benzo-5,6-chinoline, benzo-6,7-chinoline, benzo-7,8-chinoline, benzoisochinoline, acridine, phenothiazine, phenoxazine, benzopyridazine, benzopyrimidine, chinoxaline, phenazine, naphthyridine, azacarbazole, benzocarboline, phenanthridine, phenanthroline, thieno[2,3b]thiophene, thieno[3,2b]-thiophene, dithienothiophene, isobenzothiophene, dibenzothiophene, benzothiadiazothiophene or combinations of these groups.

It is particularly preferred in the host materials of the formula (45) for the group $Ar^5$ to stand for anthracene, which may be substituted by one or more substituents R, and for the groups $Ar^4$ and $Ar^6$ to be bonded in the 9 and 10-positions. Very particularly preferably, at least one of the groups $Ar^4$ and/or $Ar^6$ is a condensed aryl group selected from 1- or 2-naphthyl, 2-, 3- or 9-phenanthrenyl or 2-, 3-, 4-, 5-, 6- or 7-benzanthracenyl, each of which may be substituted by one or more radicals $R^1$. Anthracene-based compounds are described in US 2007/0092753 A1 and US 2007/0252517 A1, for example 2-(4-methylphenyl)-9,10-di-(2-naphthyl) anthracene, 9-(2-naphthyl)-10-(1,1'-biphenyl)anthracene and 9,10-bis[4-(2,2-diphenyl-ethenyl)phenyl]anthracene, 9,10-diphenylanthracene, 9,10-bis(phenyl-ethynyl)anthracene and 1,4-bis(9'-ethynylanthracenyl)benzene. Preference is also given to host materials containing two anthracene units (US 2008/0193796 A1), for example 10,10'-bis[1,1', 4',1''']terphenyl-2-yl-9,9'-bisanthracenyl.

Further preferred host materials are derivatives of arylamine, styrylamine, fluorescein, perynone, phthaloperynone, naphthaloperynone, diphenyl-butadiene, tetraphenylbutadiene, cyclopentadienes, tetraphenylcyclopentadiene, pentaphenylcyclopentadiene, coumarine, oxadiazole, bisbenzoxazoline, oxazone, pyridine, pyrazine, imine, benzothiazole, benzoxazole, benzimidazole (US 2007/0092753 A1), for example 2,2',2''-(1,3,5-phenylene)tris[1-phenyl-1H-benzimidazole], aldazines, stilbene, styrylarylene derivatives, for example 9,10-bis[4-(2,2-diphenylethenyl)-phenyl]anthracene, and distyrylarylene derivatives (U.S. Pat. No. 5,121,029), diphenylethylene, vinylanthracene, diaminocarbazole, pyran, thiopyran, diketopyrrolopyrrole, polymethine, mellocyanine, acridone, quinacridone, and cinnamic acid esters.

Particular preference is given to derivatives of arylamine and styrylamine, for example 4,4'-bis[N-(1-naphthyl)-N-(2-naphthyl)amino]biphenyl (TNB).

Preferred compounds with oligoarylene as hosts preferably for fluorescent emitter compounds are compounds as disclosed in, e.g., US 2003/0027016 A1, U.S. Pat. No. 7,326,371 B2, US 2006/043858 A, U.S. Pat. No. 7,326,371 B2, US 2003/0027016 A1, WO 2007/114358, WO 2008/145239, JP 3148176 B2, EP 1009044, US 2004/018383, WO 2005/061656 A1, EP 0681019B1, WO 2004/013073A1, U.S. Pat. No. 5,077,142, WO 2007/065678, and US 2007/0205412 A1. Particularly preferred oligoarylene-based compounds are compounds having the formulae (46) to (52).

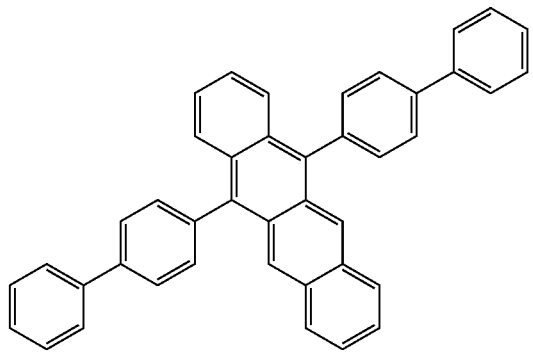

Formula (46)

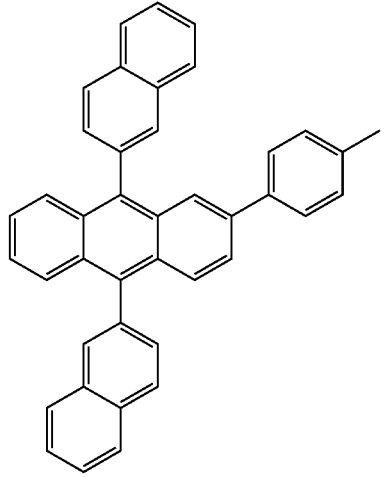

Formula (47)

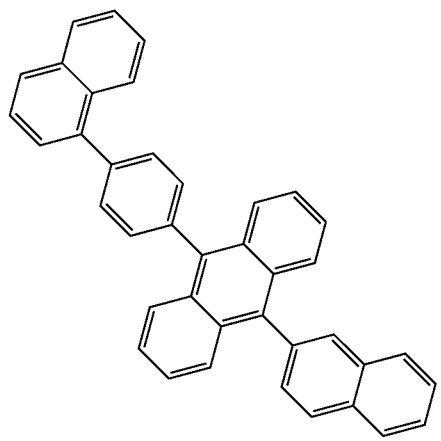

Formula (48)

Formula (49)

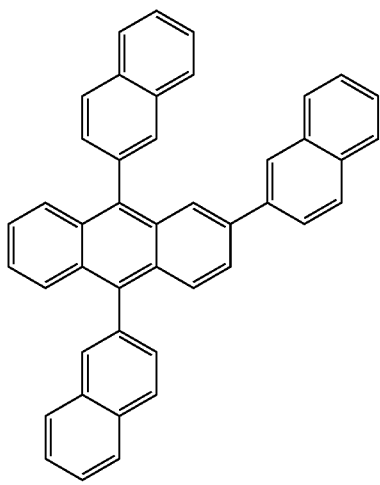

Formula (50)

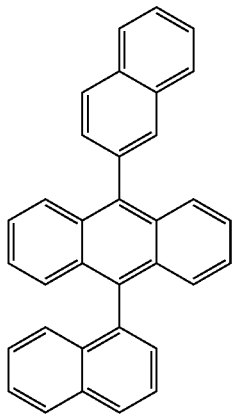

Formula (51)

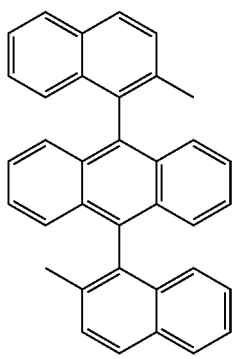

Formula (52)

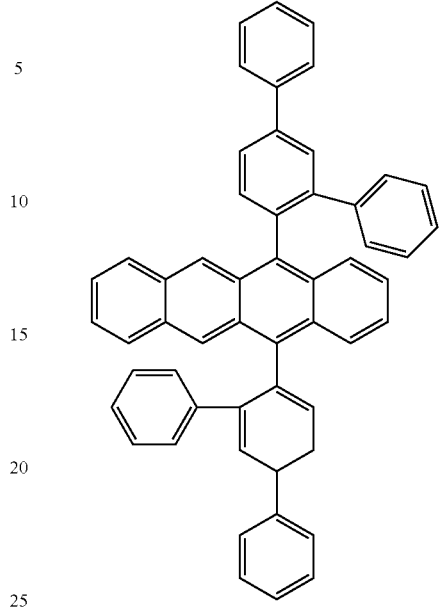

Further host materials preferably for fluorescent emitter compounds can be selected from spirobifluorene and derivates thereof, for example Spiro-DPVBi as disclosed in EP 0676461 and indenofluorene as disclosed in U.S. Pat. No. 6,562,485.

The preferred host materials suitable for phosphorescent emitter compounds, i.e. matrix materials, are selected from ketones, carbazoles, indolocarbazoles, triarylamines, indenofluorenes, fluorenes, spirobifluorenes, phenathrenes, dehydrophenanthrenes, thiophenes, triazines, imidazoles and their derivatives. Some preferred derivatives are described below in more details.

If a phosphorescent emitter compound is employed the host material must fulfil rather different characteristics as compared to host materials used for fluorescent emitter compounds. The host materials used for phosphorescent emitter compounds are required to have a triplet level which is higher in energy as compared to the triplet level of the emitter. The host material can either transport electrons or holes or both of them. In addition, the emitter is supposed to have large spin-orbital coupling constants in order to facilitate singlet-triplet mixing sufficiently. This can be enabled by using metal complexes.

Further examples for triplet matrix materials are N,N-biscarbazolylbiphenyl (CBP), carbazole derivatives (for example in accordance with WO 2005/039246, US 2005/0069729, JP 2004/288381, EP 1205527 or DE 102007002714), azacarbazoles (for example in accordance with EP 1617710, EP 1617711, EP 1731584, JP 2005/347160), ketones (for example in accordance with WO 2004/093207), phosphine oxides, sulfoxides and sulfones (for example in accordance with WO 2005/003253), oligophenylenes, aromatic amines (for example in accordance with US 2005/0069729), bipolar matrix materials (for example in accordance with WO 2007/137725), silanes (for example in accordance with WO 2005/111172), 9,9-diarylfluorene derivatives (e.g. in accordance with DE 102008017591), azaboroles or boronic esters (for example in accordance with WO 2006/117052), triazole derivatives, oxazoles and oxazole derivatives, imidazole derivatives, pyrazoline derivatives, pyrazolone derivatives, distyrylpyrazine derivatives, thiopyran dioxide derivatives, phenylenediamine derivatives, tertiary aromatic amines, styrylamines, indoles, anthrone derivatives, fluorenone derivatives, fluorenylidenemethane derivatives, hydrazone derivatives, silazane derivatives, aromatic dimethylidene compounds, porphyrin compounds, carbodiimide derivatives, diphenylquinone derivatives, phthalocyanine derivatives, metal complexes of 8 hydroxyquinoline derivatives, such as, for example, Alq$_3$, the 8 hydroxyquinoline complexes may also contain triarylaminophenol ligands (US 2007/0134514 A1), thiophene oligomers.

Particularly preferred matrix materials are selected from compounds comprising indolocarbazoles and their derivatives (e.g. formulae (53) to (59)), as disclosed for examples in DE 102009023155.2, EP 0906947B1, EP 0908787B1, EP 906948B1, WO 2008/056746A1, WO 2007/063754A1, WO 2008/146839A1, and WO 2008/149691A1.

Formula (53)

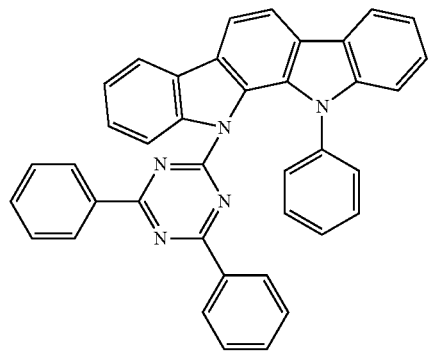

Formula (54)

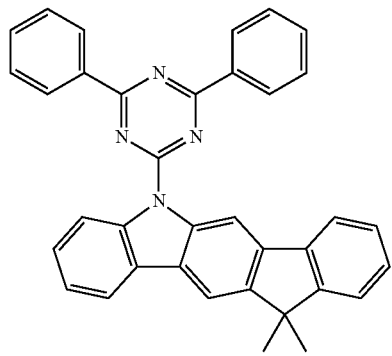

Formula (55)

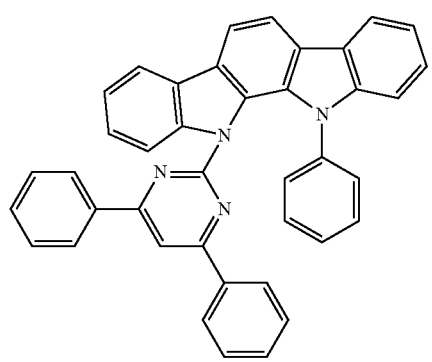

Formula (56)

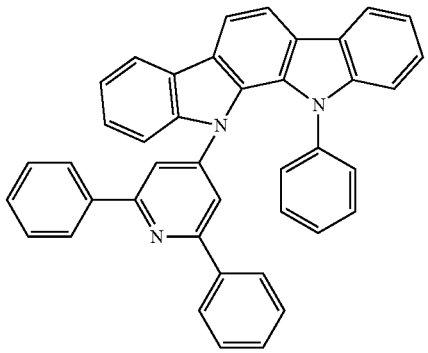

Formula (57)

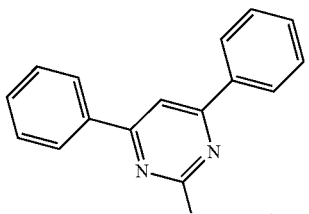

Formula (58)

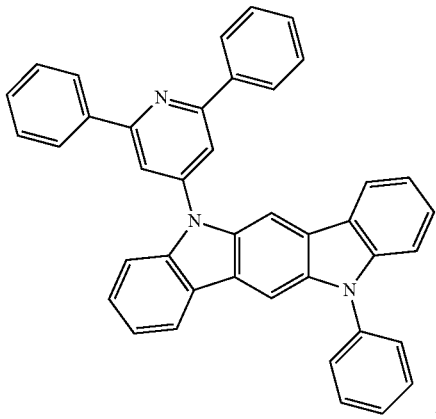

Formula (59)

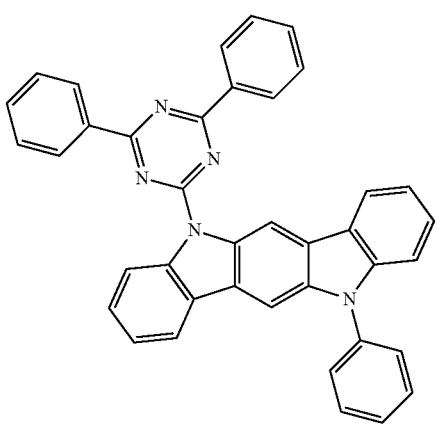

Examples of preferred carbazole derivatives are, 1,3-N,N-dicarbazole-benzene (=9,9'-(1,3-phenylene)bis-9H-carbazole) (mCP), 9,9'-(2,2'-dimethyl[1,1'-biphenyl]-4,4'-diyl)bis-9H-carbazole (CDBP), 1,3-bis(N,N'-dicarbazole)benzene (=1,3-bis(carbazol-9-yl)benzene), 3,5-di(9H-carbazol-9-yl)biphenyl and compounds of the formulae (60) to (64).

Formula (60)

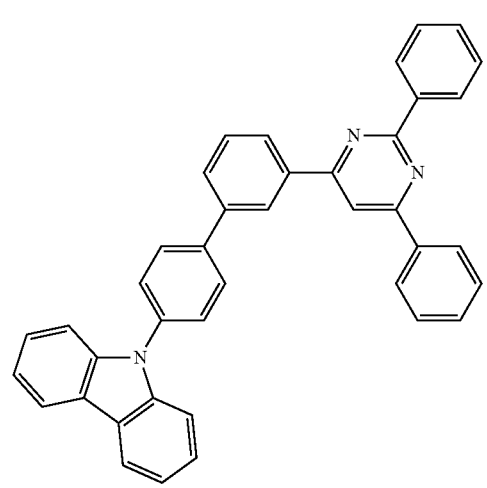

Formula (61)

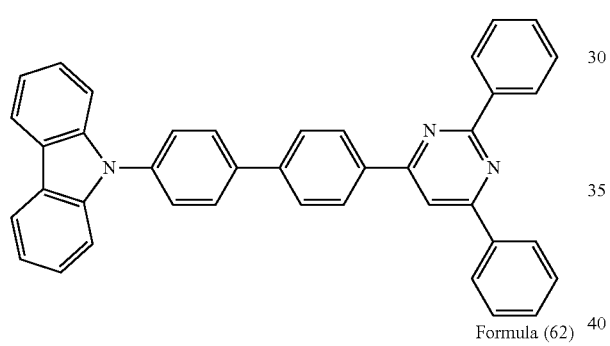

Formula (62)

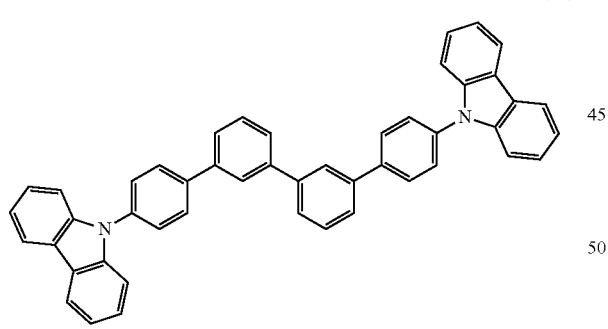

Formula (63)

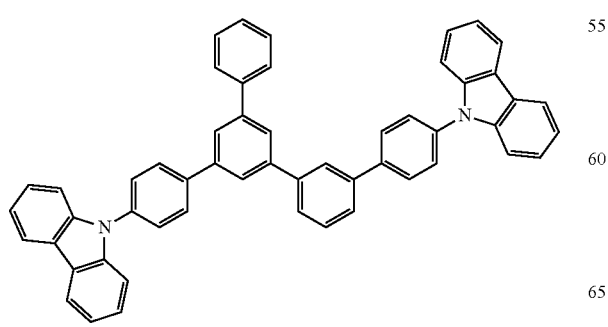

Formula (64)

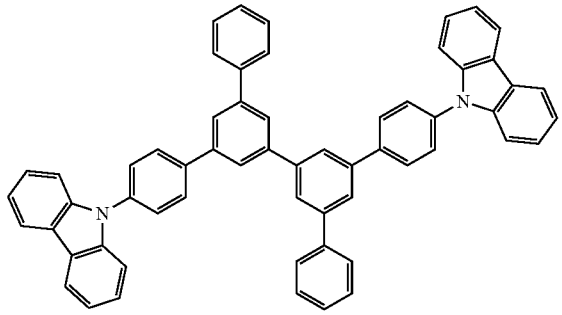

Further preferred compounds are, for example, (US 2004/0209115, US 2004/0209116, US 2007/0087219 A1, US 2007/0087219 A1) the Si tetraaryl compounds of the formulae (65) to (70) as a matrix forming material.

Formula (65)

Formula (66)

Formula (67)

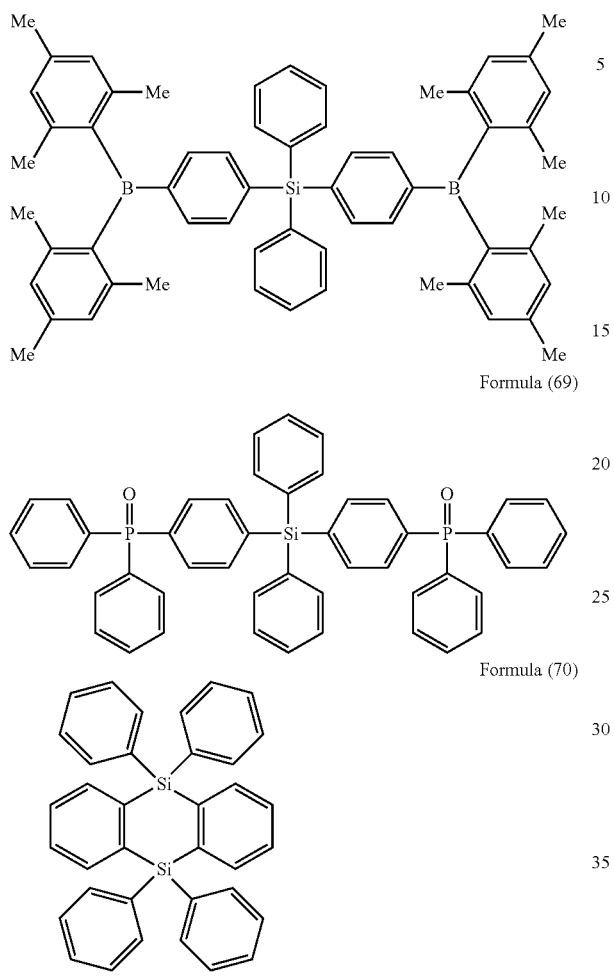

Formula (68)

Formula (69)

Formula (70)

In case the host material serves as matrix for a emitter compound the emitter compound is required to have a smaller band gap as compared to the host compound. In general, smaller band gaps can be achieved by extending the π-electron system of conjugated molecular systems. Emitter compounds tend, therefore, to have more extended conjugated π-electron systems than host molecules. Many examples have been published, e.g. styrylamine derivatives as disclosed in JP 2913116 B and WO 2001/021729 A1, and indenofluorene derivatives as disclosed in WO 2008/006449 and WO 2007/140847.

In case the above mentioned examples of host/matrix compounds are ionic compounds they may act as the multi-charged organic cation or anion M itself. In this case M is consisting of the functional organic group.

In case the above mentioned examples of host/matrix compounds are non-ionic compounds they are part of the multi-charged organic cation or anion M. In this case the host/matrix compounds are the above-mentioned functional organic group comprised in the multi-charged organic cation or anion M and are bound to the charged part of M in that at least two hydrogen atoms are not present in the above mentioned compounds and the compounds are connected to the charged part of M via the positions where the hydrogen atoms are not present.

Examples for suitable multicharged cation or anion comprising a matrix or host group are listed as follows. Further suitable examples can be readily made by the combination of the host groups as described above and the anion and cation groups as described below.

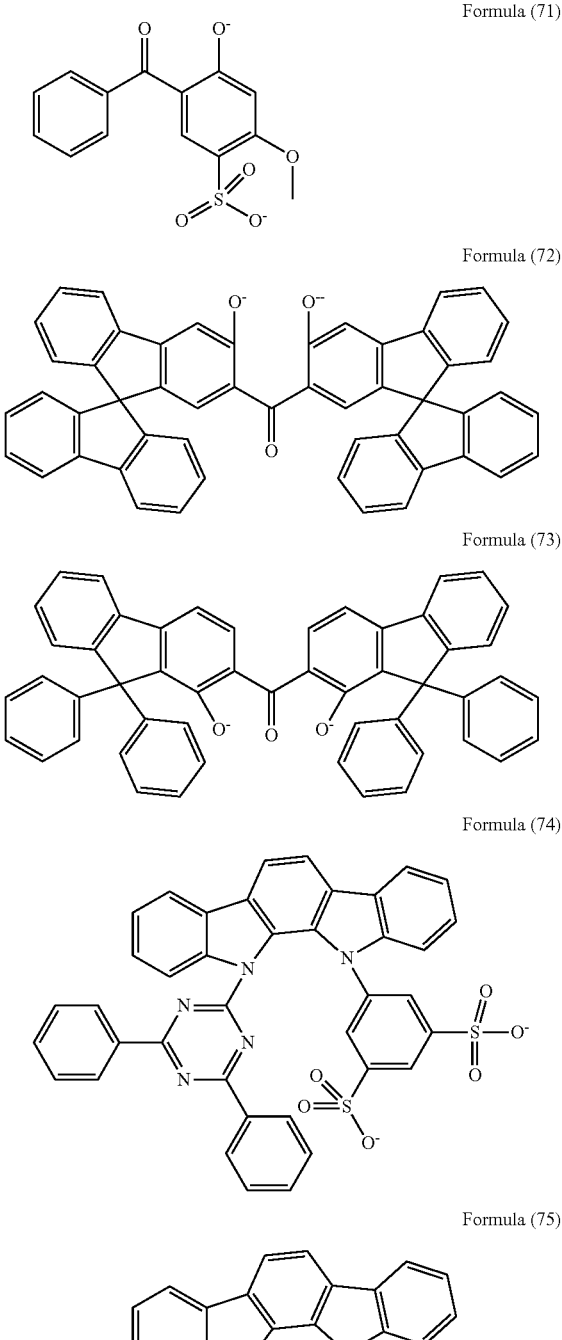

Formula (71)

Formula (72)

Formula (73)

Formula (74)

Formula (75)

Formula (76)
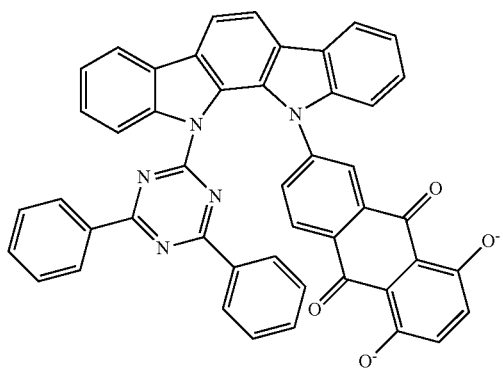
Formula (77)
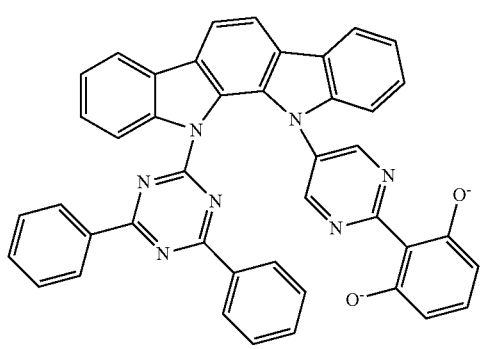
Formula (78)
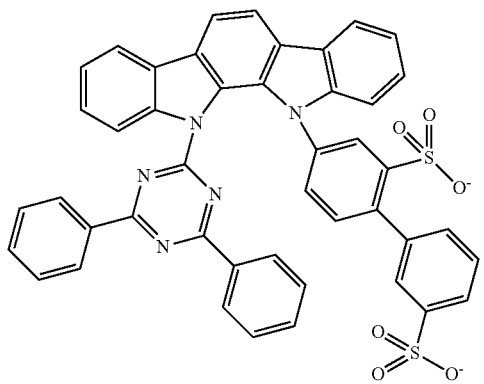
Formula (79)
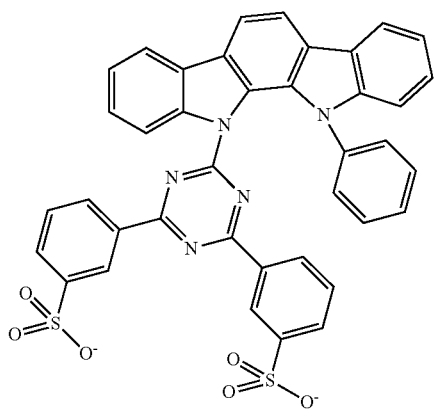
Formula (80)
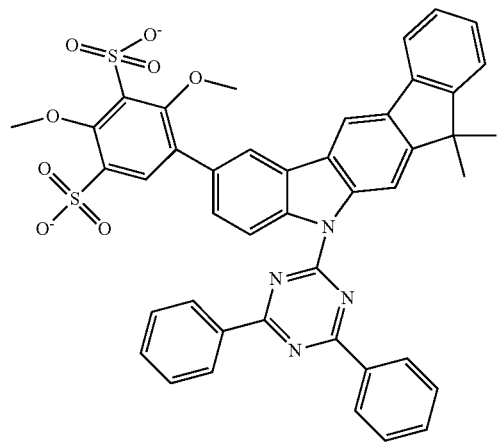
Formula (81)
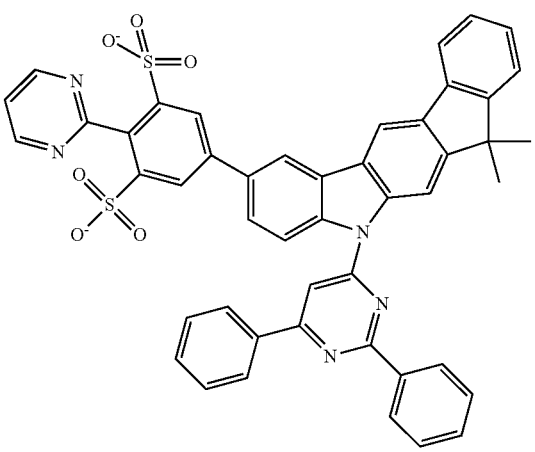
Formula (82)
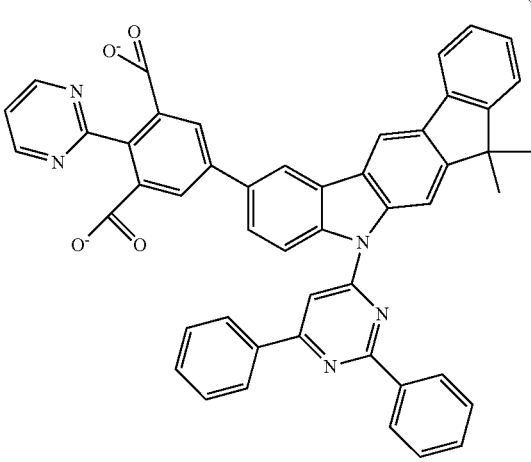

-continued
Formula (83)
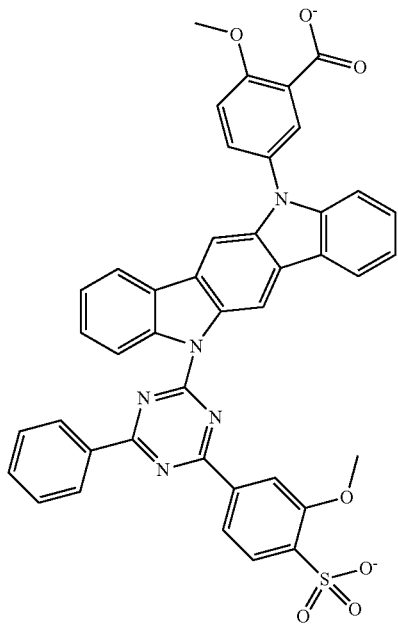
Formula (84)
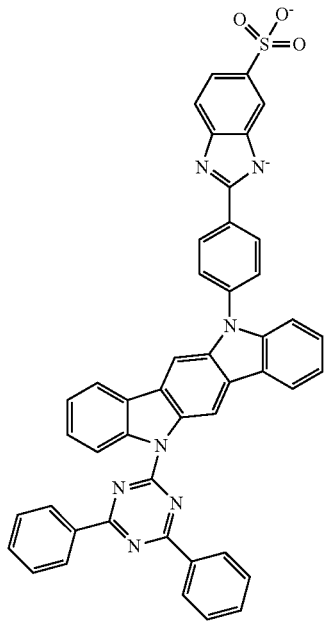
Formula (85)
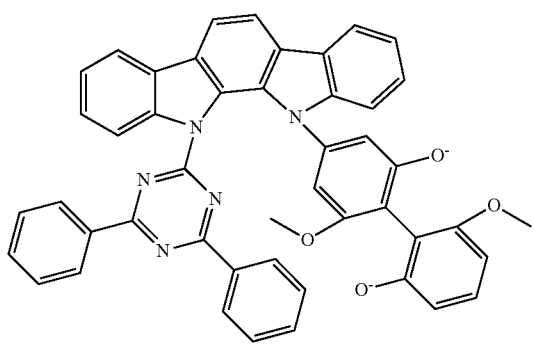
-continued
Formula (86)
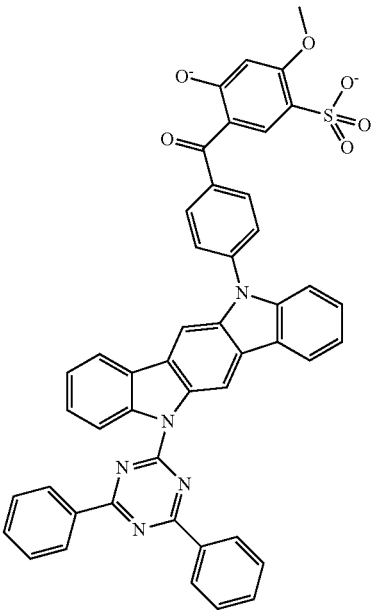
Formula (87)
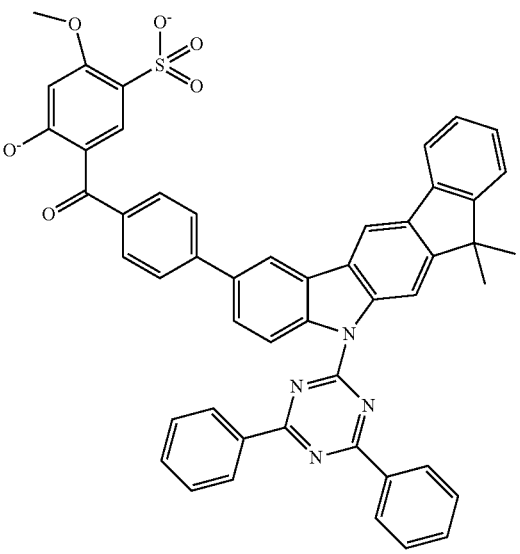
Formula (88)
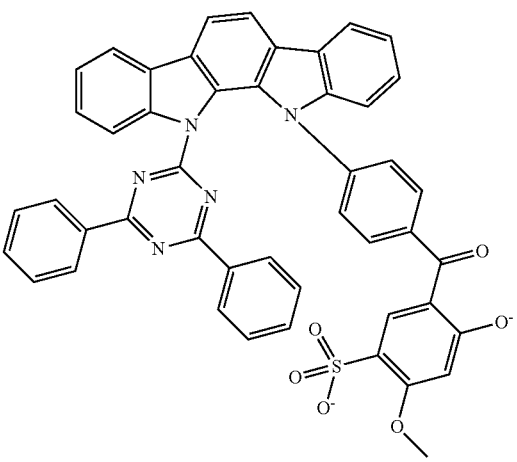

Formula (89)
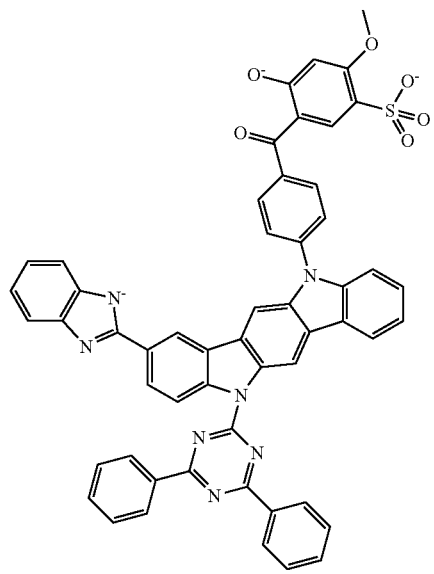
Formula (90)
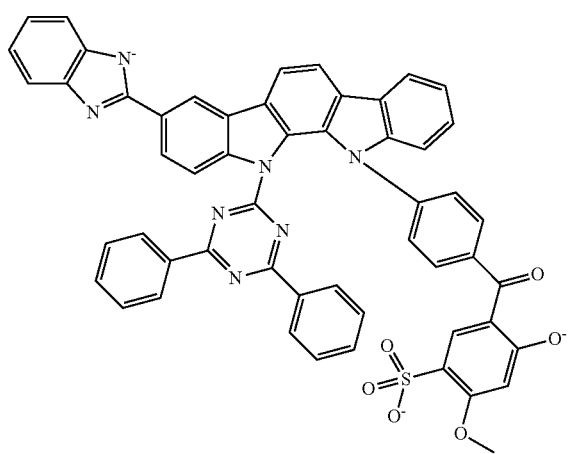
Formula (91)
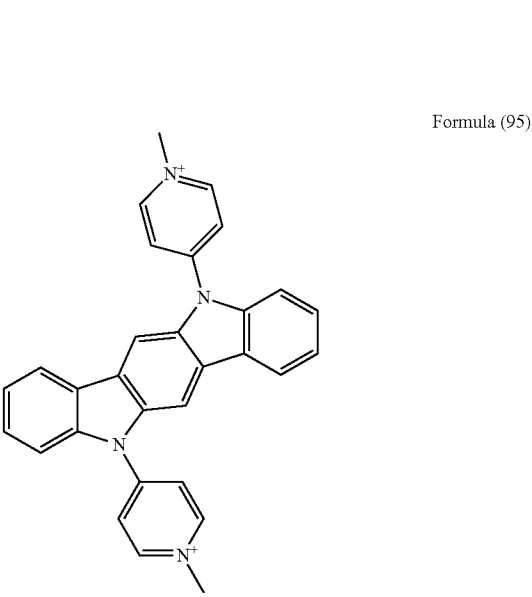
Formula (92)
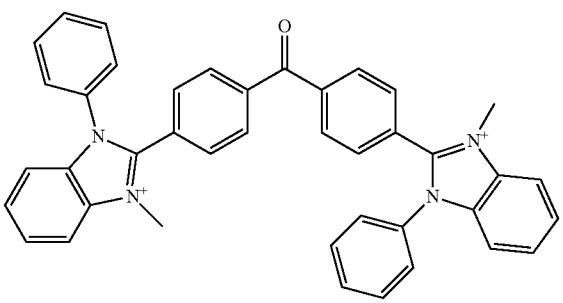
Formula (93)
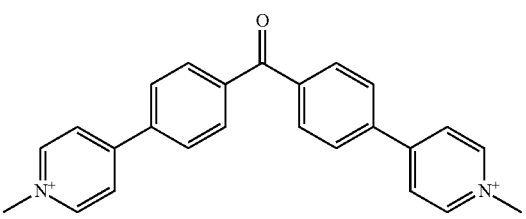
Formula (94)
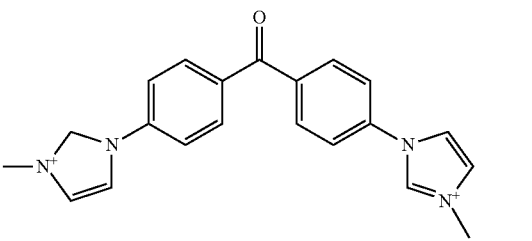
Formula (95)

Formula (96)
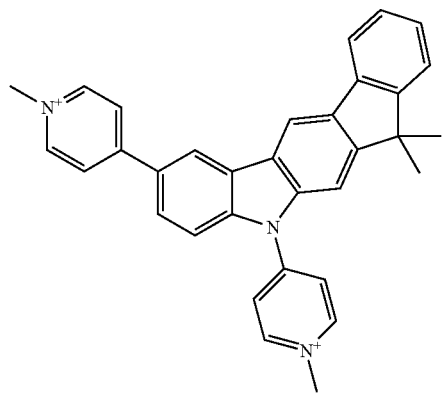
Formula (97)
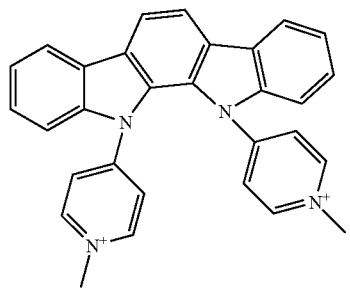
Formula (98)
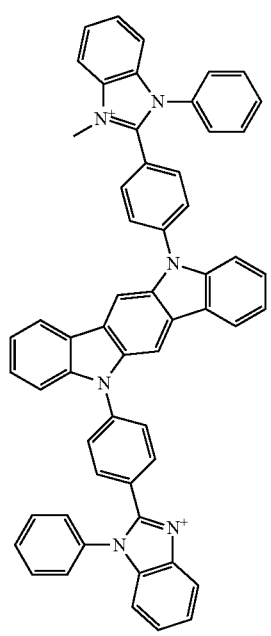
Formula (99)
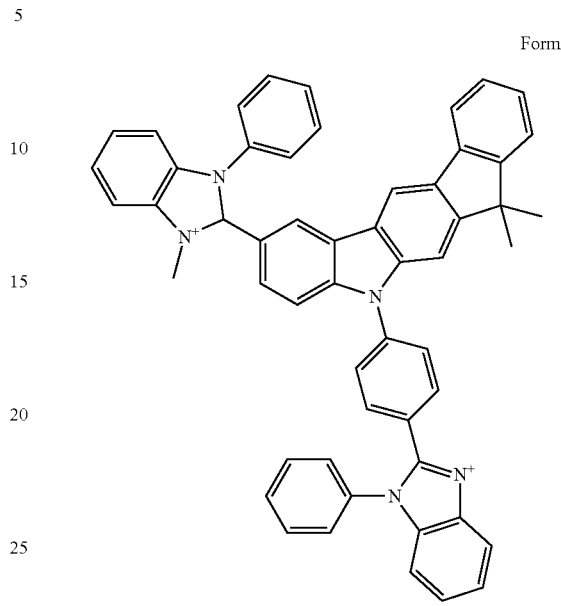
Formula (100)
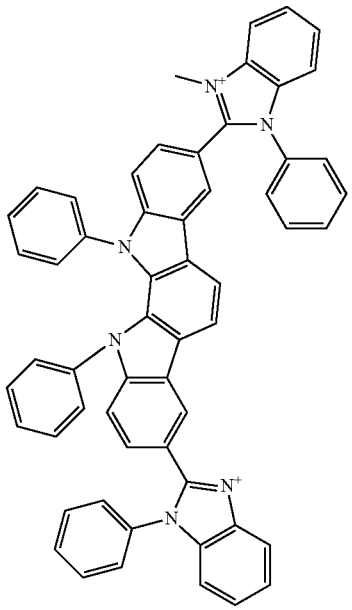

Formula (101)
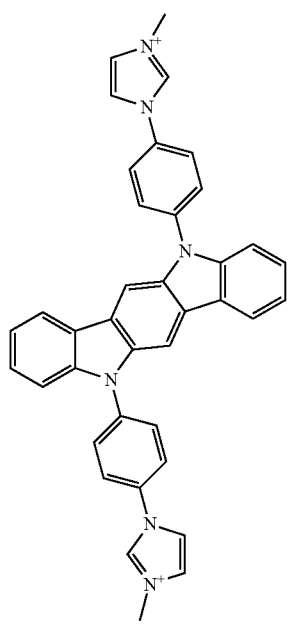
Formula (104)
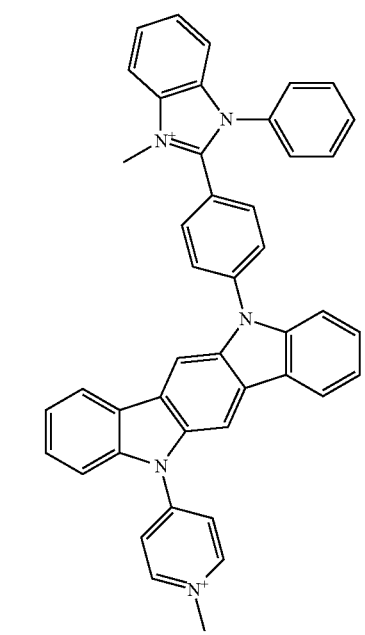
Formula (102)
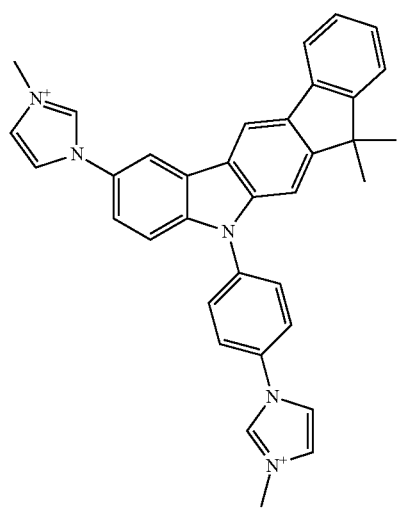
Formula (105)
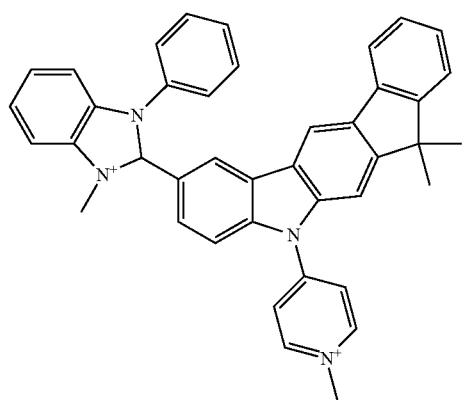
Formula (103)
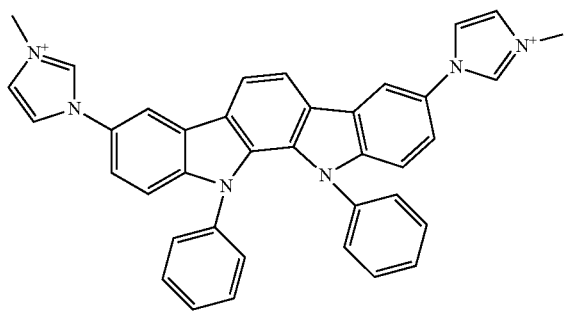
Formula (106)
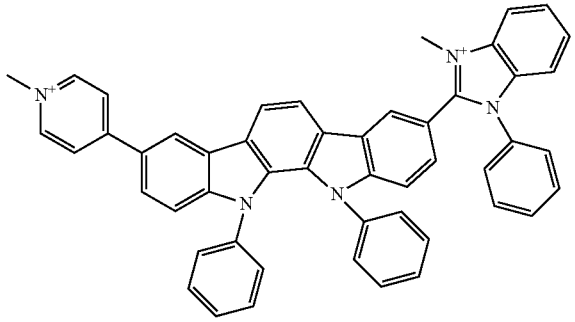

Formula (107)
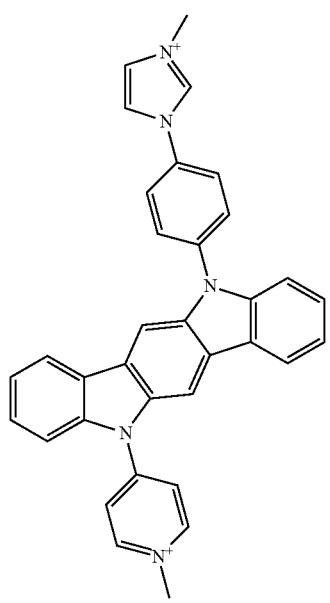
Formula (108)
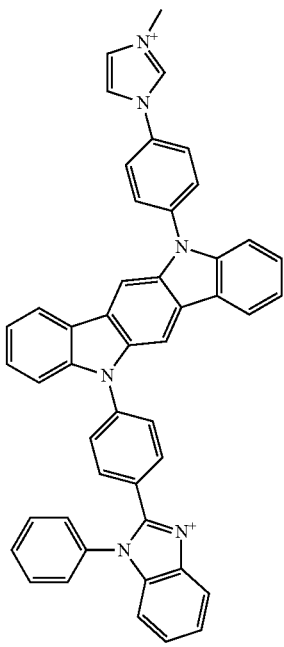
Formula (109)
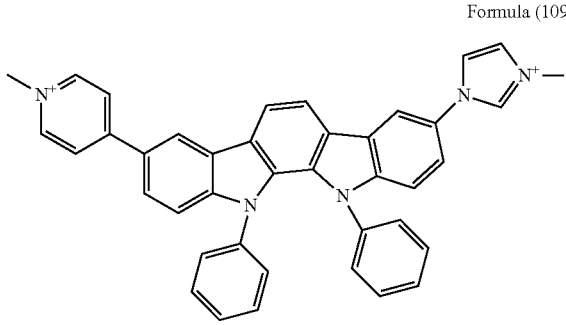
Formula (110)
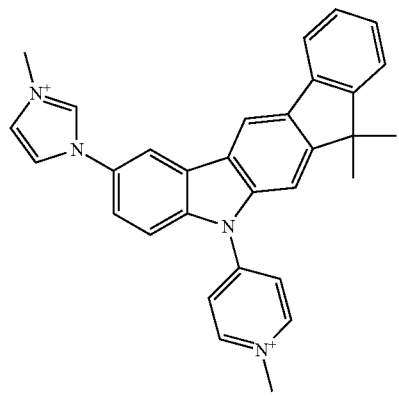
Formula (111)
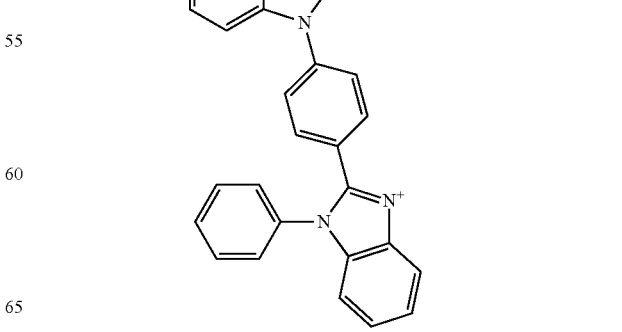

Formula (112)
Formula (113)
Formula (114)
Formula (115)
Formula (116)
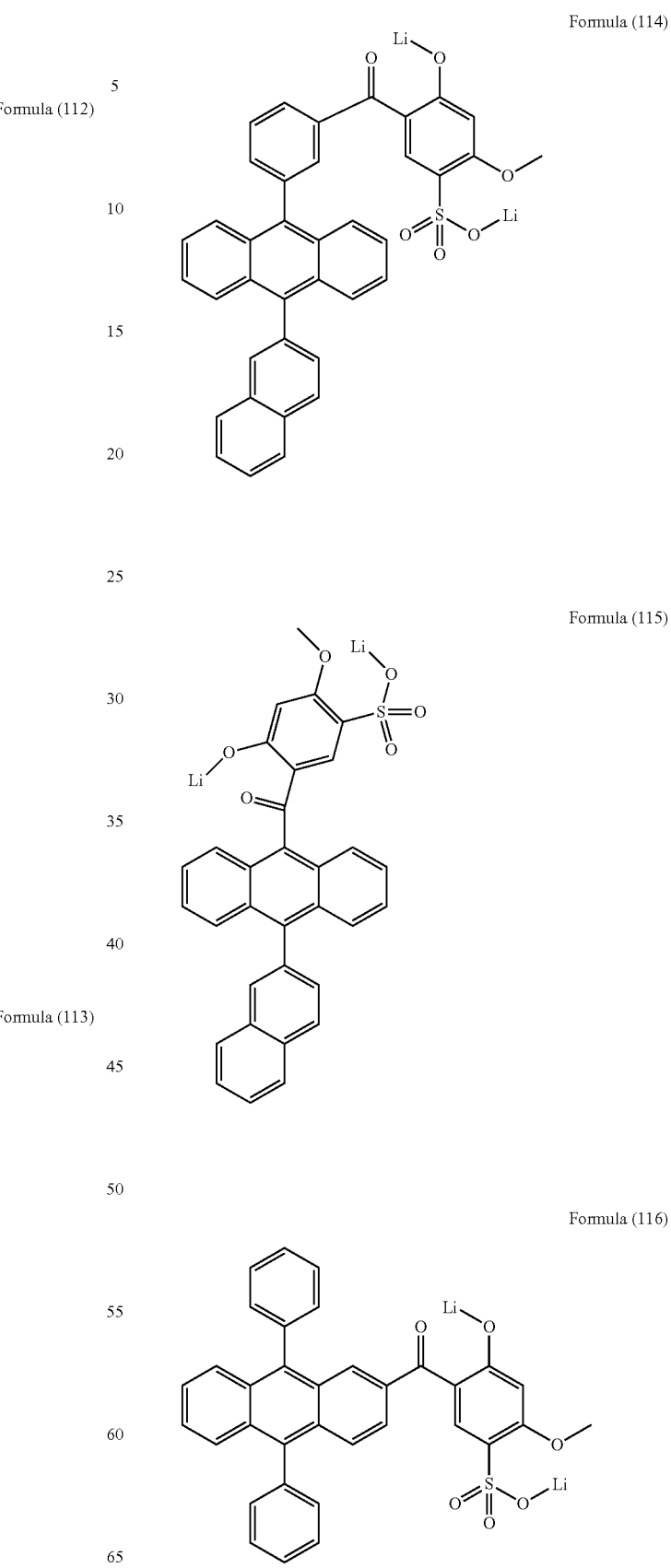

Formula (117)
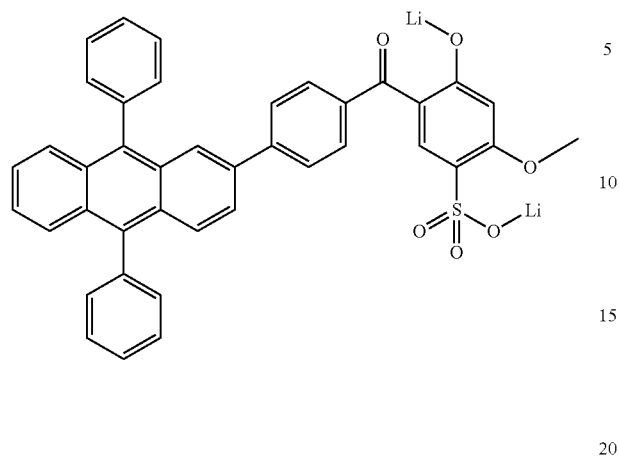
Formula (120)
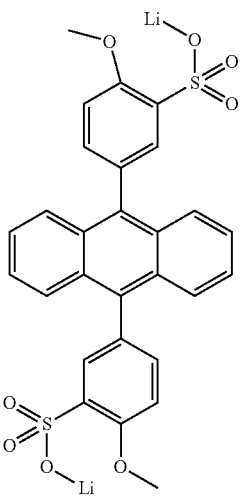
Formula (118)
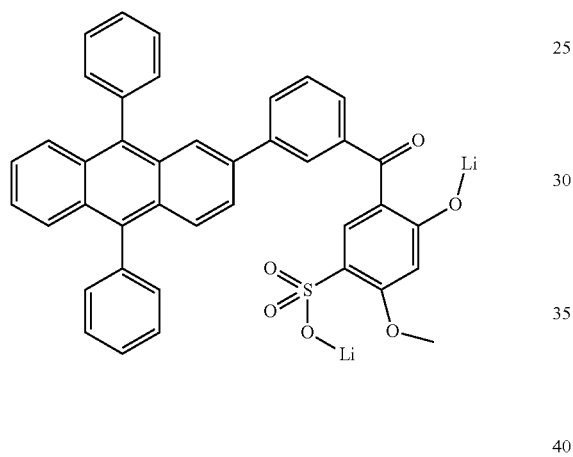
Formula (121)
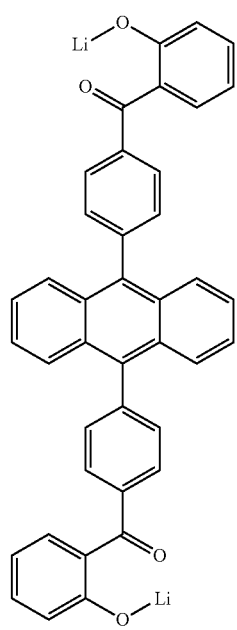
Formula (119)
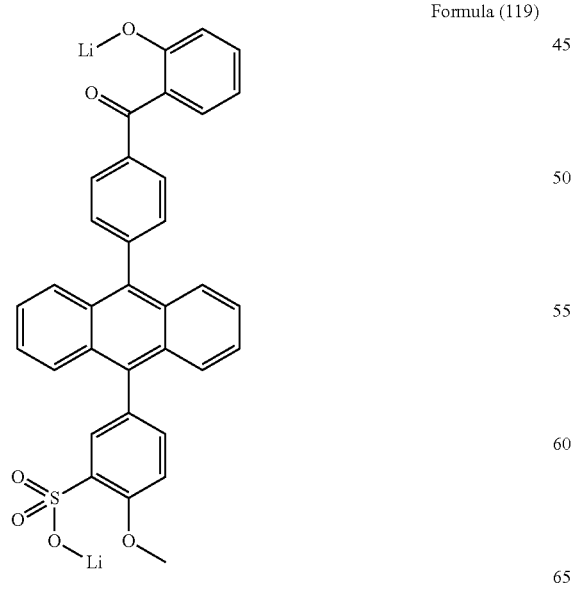
Formula (122)
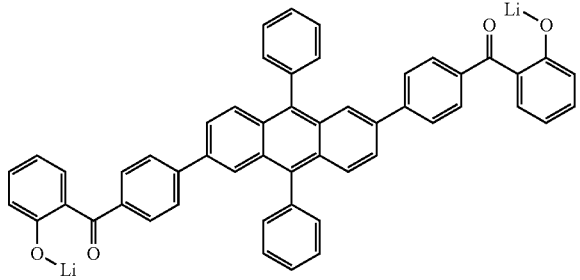

Formula (123)
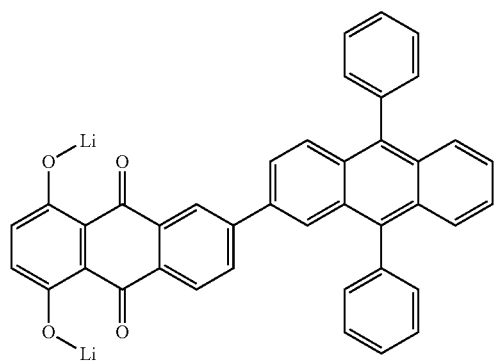
Formula (124)
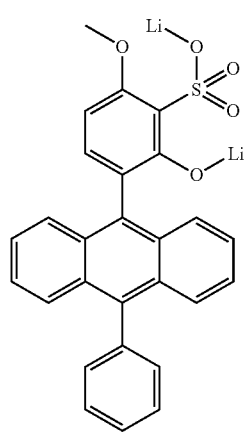
Formula (125)
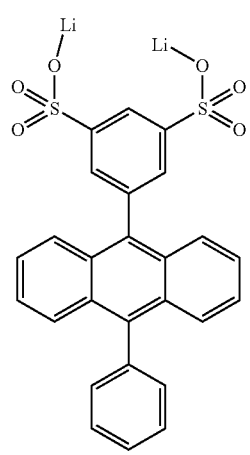
Formula (126)
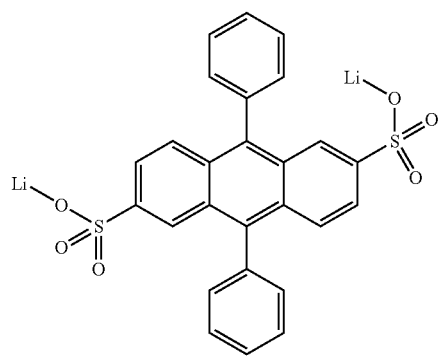
Formula (127)
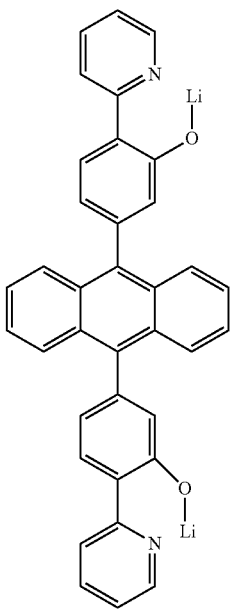
Formula (128)
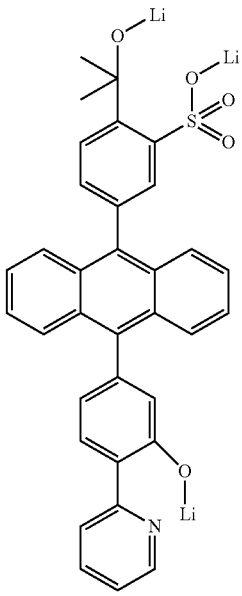
Formula (129)
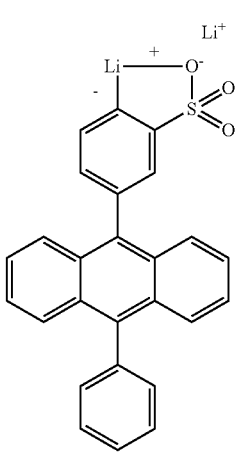

-continued

Formula (130)

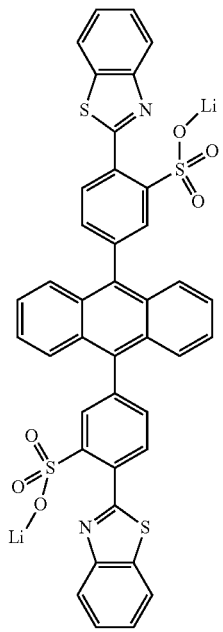

Formula (131)

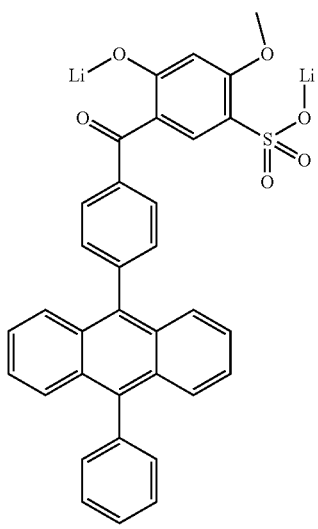

Formula (132)

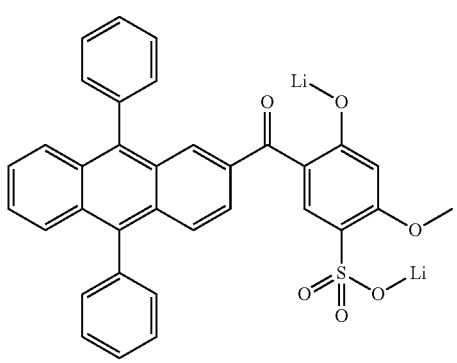

A general synthesis route for obtaining such compounds is provided below.

In another embodiment of the present invention the multi-charged cation or anion M in the compound of formula (1) comprises a hole injection group or hole transport group. In this case the multi-charged organic cation or anion M may act as hole injection material (HIM) or hole transport material (HTM). That is, the hole injection group or the hole transport group gives the organic ionic compound of formula (1) the ability to inject or transport holes (positive charges) within the organic ionic compound. A HTM is characterized in that it is a material or unit capable of transporting holes (i.e. positive charges) injected from a hole injecting material or an anode. In many cases, HIM can function also as HTM, depending on the adjacent layer.

In principle any HTM or HIM known to the skilled one in the art of OLED or electroluminescent devices can be included as hole injection group or hole transport group in M of formula (1) or can be used as non-ionic organic functional material for compositions according to the present invention in an electronic device. Suitable hole injection groups/materials or hole transport groups/materials are preferably selected from aromatic amines, triarylamines, tetraaryl para-phenylene diamine, thiophenes, benzothiophene, dibenzothiophene, carbazoles, indolocarbazole, indenofluorenes, phthalocyanines, porphyrines, pyrrole, thianthrene, phenoxazine phenothiazine, dihydrophenazine, isomers and derivatives thereof. Preferably, the hole injection group/material or hole transport group/material in their non-ionic form has a HOMO at an energy level of more than −5.8 eV, compared to the energy level in vacuum.

Suitable HTMs or HIMs, which can be used according to the present invention are for example phenylenediamine derivatives (U.S. Pat. No. 3,615,404), arylamine derivatives (U.S. Pat. No. 3,567,450), amino-substituted chalcone derivatives (U.S. Pat. No. 3,526,501), styrylanthracene derivatives (JP A 56-46234), fluorenone derivatives (JP A 54-110837), hydrazone derivatives (U.S. Pat. No. 3,717,462), stilbene derivatives (JP A 61-210363), silazane derivatives (U.S. Pat. No. 4,950,950), thiophene oligomers, porphyrin compounds (JP A 63-2956965), aromatic dimethylidene-type compounds, carbazole compounds, such as, for example, CDBP, CSP, mCP, aromatic tertiary amine and styrylamine compounds (U.S. Pat. No. 4,127,412), and monomeric triarylamines (U.S. Pat. No. 3,180,730). Even more triarylamino groups may also be present in the molecule.

Preference is given to aromatic tertiary amines containing at least two tertiary amine units (U.S. Pat. No. 4,720,432 and U.S. Pat. No. 5,061,569), such as, for example, 4,4'-bis[N-(1-naphthyl)-N-phenylamino]biphenyl (NPD) (U.S. Pat. No. 5,061,569) or MTDATA (JP A 4-308688), N,N,N',N'-tetra(4-biphenyl)diaminobiphenylene (TBDB), 1,1-bis(4-di-p-tolylaminophenyl)cyclohexane (TAPC), 1,1-bis(4-di-p-tolylaminophenyl)-3-phenylpropane (TAPPP), 1,4-bis[2-[4-[N,N-di(p-tolyl)amino]phenyl]vinyl]benzene (BDTAPVB), N,N,N',N'-tetra-p-tolyl-4,4'-diaminobiphenyl (TTB), TPD, N,N,N',N'-tetraphenyl-4,4'''-diamino-1,1':4',1'':4'',1'''-quaterphenyl, likewise tertiary amines containing carbazole units, such as, for example, 4 (9H-carbazol-9-yl)-N,N-bis[4-(9H-carbazol-9-yl)phenyl]benzeneamine (TCTA). Preference is likewise given to hexaazatriphenylene compounds in accordance with US 2007/0092755 A1.

Particular preference is given to the following triarylamine compounds of the formulae (133) to (138), which may also be substituted, and as disclosed in EP 1162193 A1, EP 650955 A1, Synth. Metals 1997, 91(1-3), 209, DE 19646119 A1, WO 2006/122630 A1, EP 1860097 A1, EP 1834945 A1, JP 08053397 A, U.S. Pat. No. 6,251,531 B1, and WO 2009/041635.

Formula (133)

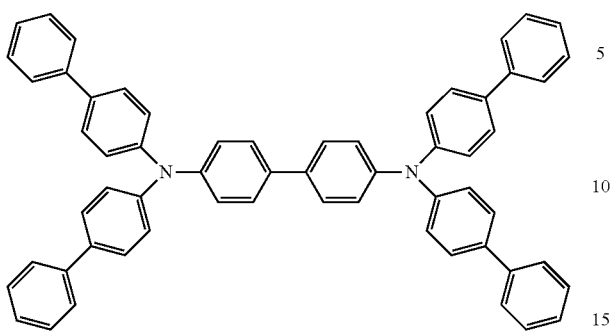

Formula (137)

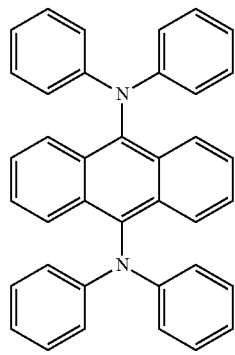

Formula (134)

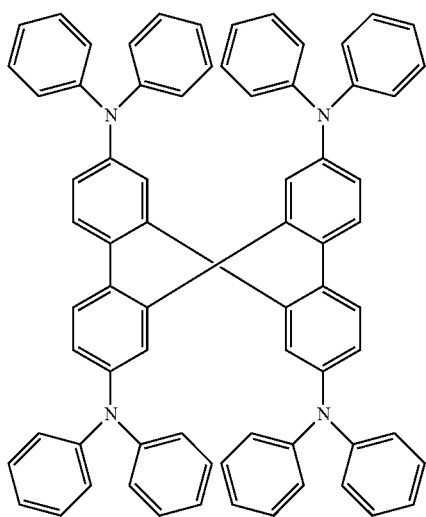

Formula (138)

Formula (135)

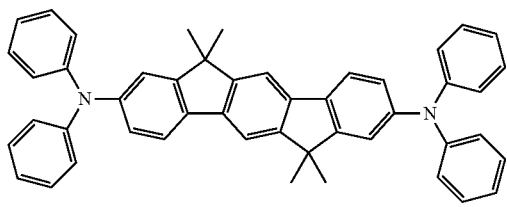

Formula (136)

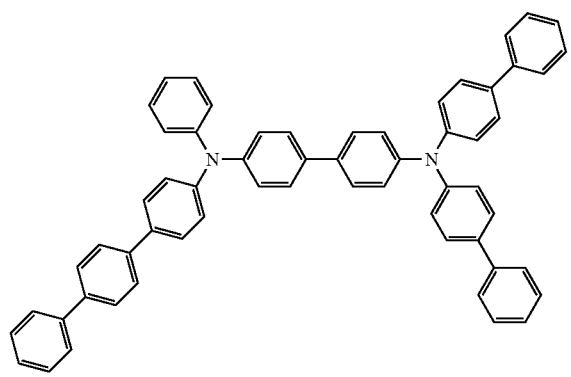

Further to HIMs mentioned elsewhere herein, suitable HIMs are phenylenediamine derivatives (U.S. Pat. No. 3,615,404), arylamine derivatives (U.S. Pat. No. 3,567,450), amino-substituted chalcone derivatives (U.S. Pat. No. 3,526,501), styrylanthracene derivatives (JP Showa 54 (1979) 110837), hydrazone derivatives (U.S. Pat. No. 3,717,462), acylhydrazones, stilbene derivatives (JP Showa 61 (1986) 210363), silazane derivatives (U.S. Pat. No. 4,950,950), porphyrin compounds (JP Showa 63 (1988) 2956965, U.S. Pat. No. 4,720,432), aromatic tertiary amines and styrylamines (U.S. Pat. No. 4,127,412), triphenylamines of the benzidine type, triphenylamines of the styrylamine type, and triphenylamines of the diamine type. Arylamine dendrimers can also be used (JP Heisei 8 (1996) 193191), as can phthalocyanine derivatives, naphthalocyanine derivatives, or butadiene derivatives, are also suitable.

Preferably, the HIM is selected from monomeric organic compounds comprising amines, triarylamines, thiophenes, carbazoles, phthalocyanines, porphyrines and their derivatives.

Particular preference is given to the tertiary aromatic amines (US 2008/0102311 A1), for example N,N'-diphenyl-N,N'-di(3-tolyl)benzidine (=4,4'-bis[N-3-methylphenyl]-N-phenylamino)biphenyl (NPD) (U.S. Pat. No. 5,061,569), N,N'-bis(N,N'-diphenyl-4-aminophenyl)-N,N-diphenyl-4,4'-diamino-1,1'-biphenyl (TPD 232) and 4,4',4"-tris[3-methylphenyl)-phenylamino]-triphenylamine (MTDATA) (JP Heisei 4 (1992) 308688) or phthalocyanine derivatives (for example H2Pc, CuPc, CoPc, NiPc, ZnPc, PdPc, FePc, MnPc, ClAlPc, ClGaPc, ClInPc, ClSnPc, Cl2SiPc, (HO)AlPc, (HO)GaPc, VOPc, TiOPc, MoOPc, GaPc-O-GaPc).

Particular preference is given to the following triarylamine compounds of the formulae (139) (TPD 232), (140), (141) and (142), which may also be substituted, and further compounds as disclosed in U.S. Pat. No. 7,399,537 B2, US 2006/0061265 A1, EP 1661888 A1, and JP 08292586 A.

Further compounds suitable as HIM are disclosed in EP 0891121 A1 and EP 1029909 A1.

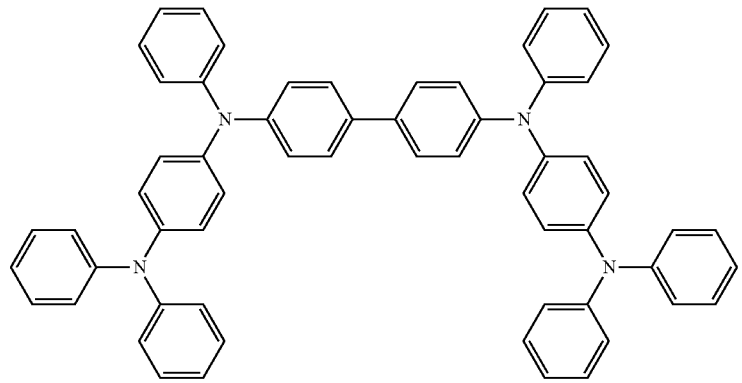

Formula (139)

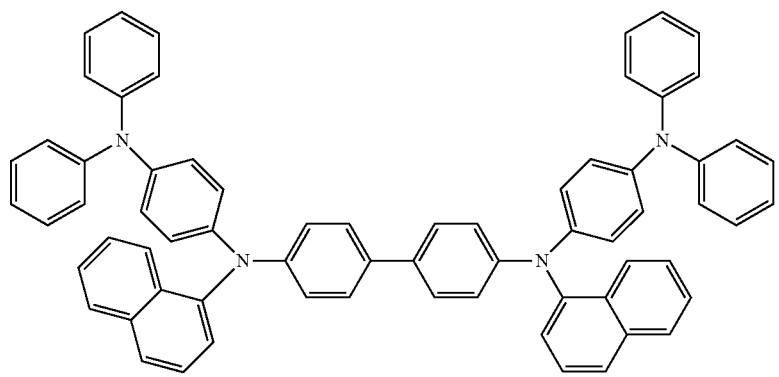

Formula (140)

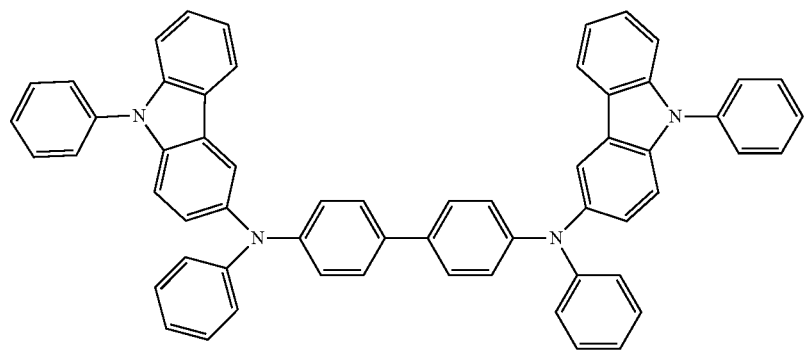

Formula (141)

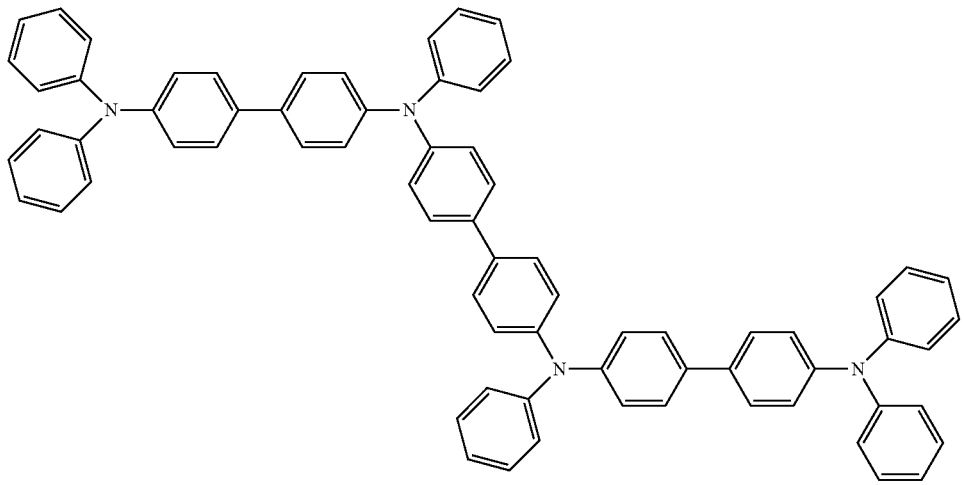

Formula (142)

In case the above mentioned examples of HTM and HIM compounds are ionic compounds they may act as the multi-charged organic cation or anion M itself. In this case M is consisting of the functional organic group.

In case the above mentioned examples of HTM and HIM compounds are non-ionic compounds they are part of the multi-charged organic cation or anion M. In this case the HTM and HIM compounds are the above-mentioned functional organic group comprised in the multi-charged organic cation or anion M and are bound to the charged part of M in that at least two hydrogen atoms are not present in the above mentioned compounds and the compounds are connected to the charged parts of M via the positions where the hydrogen atoms are not present.

Examples for suitable cation or anion comprising a HTMs or HIMs group are listed as follows. Further suitable examples can be readily made by the combination of the host groups as described above and the anion and cation groups as described below.

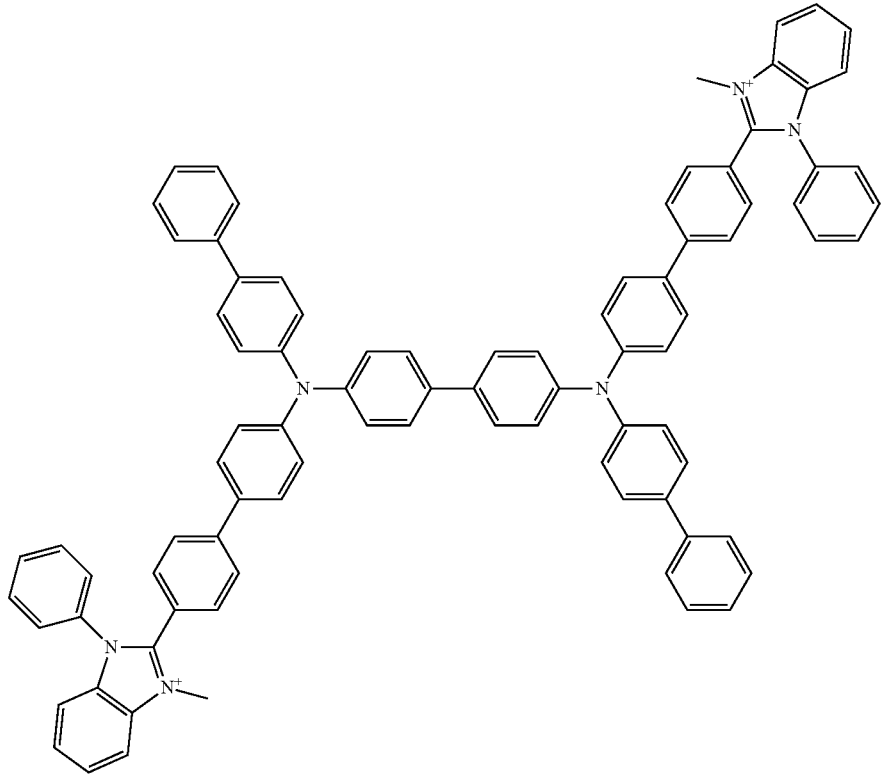

Formula (143)

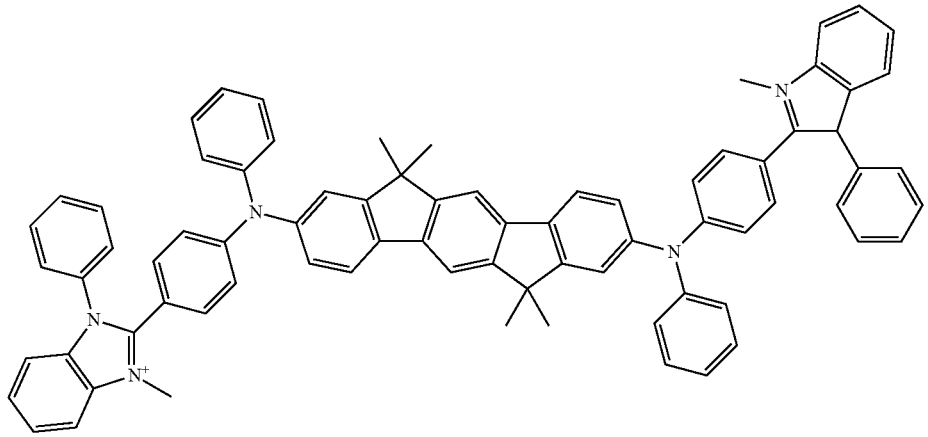
Formula (144)
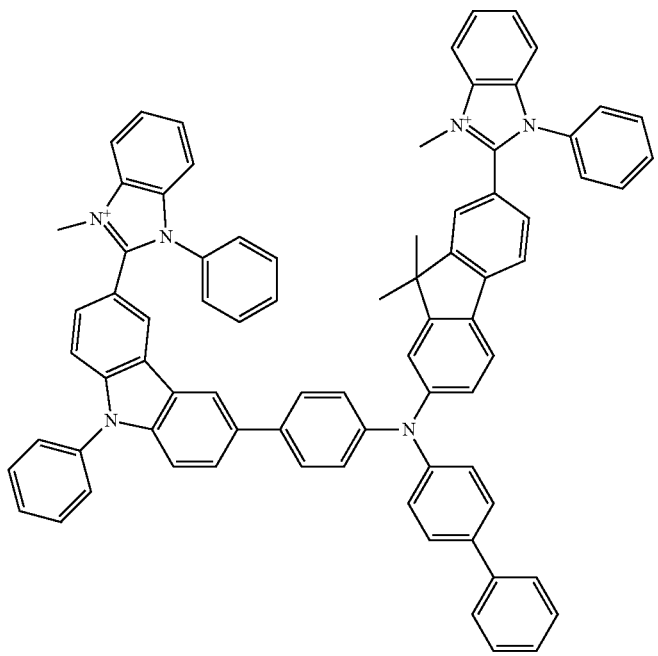
Formula (145)

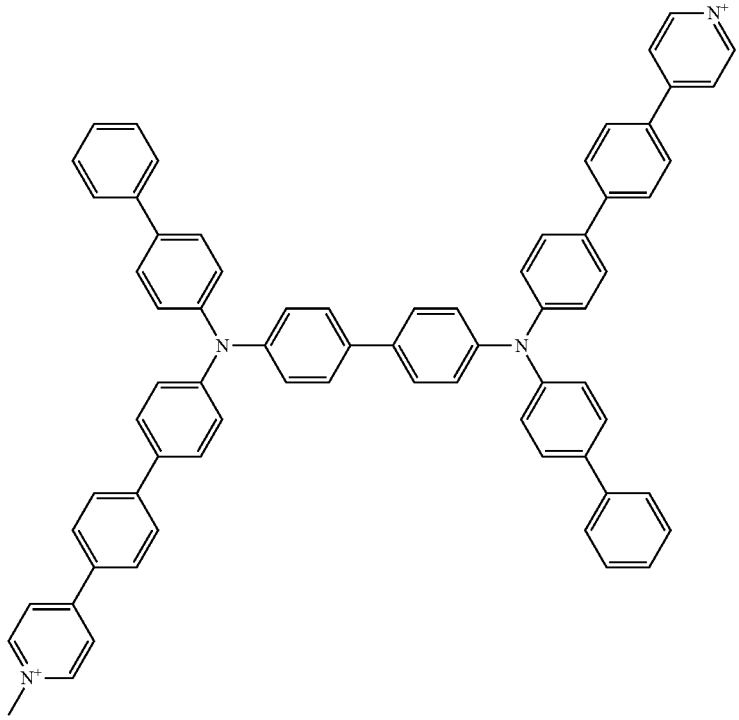
Formula (146)
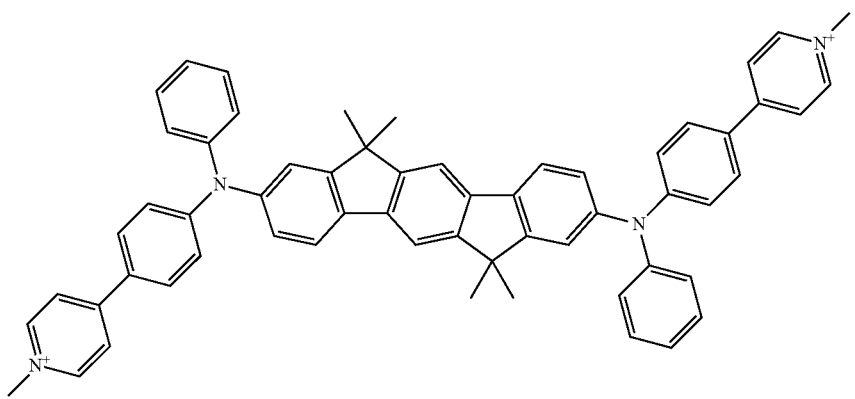
Formula (147)

-continued
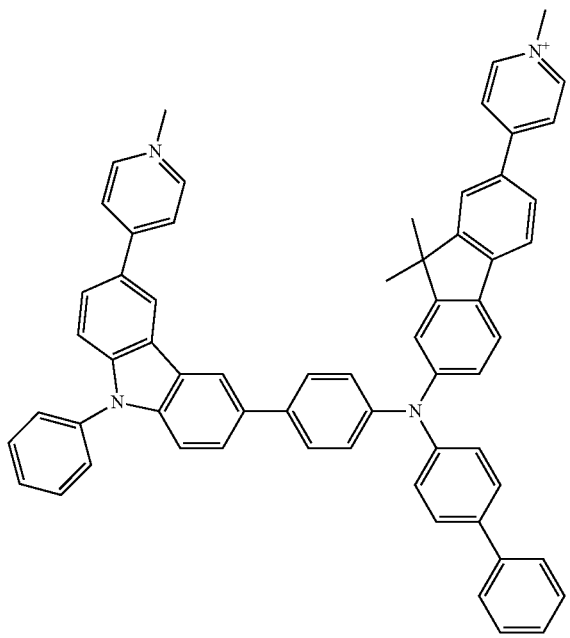
Formula (148)
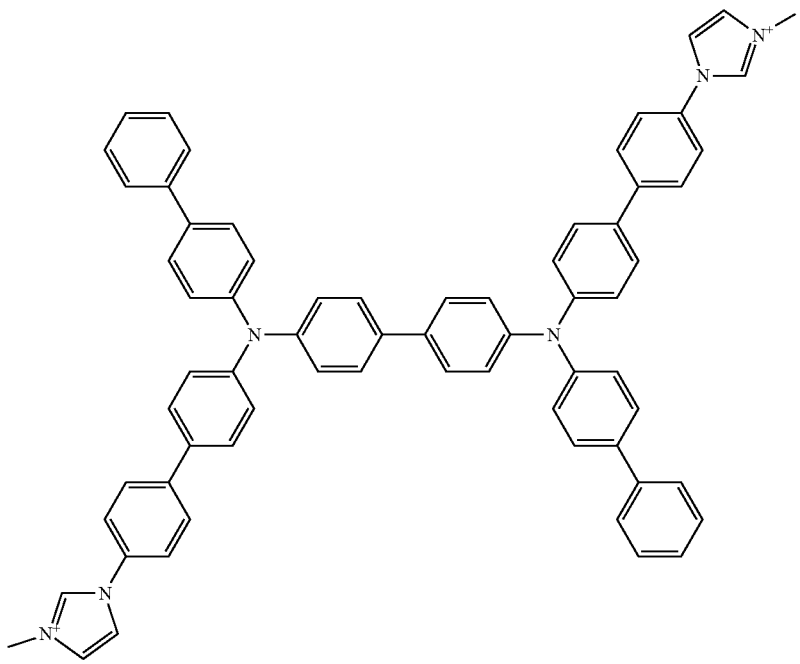
Formula (149)
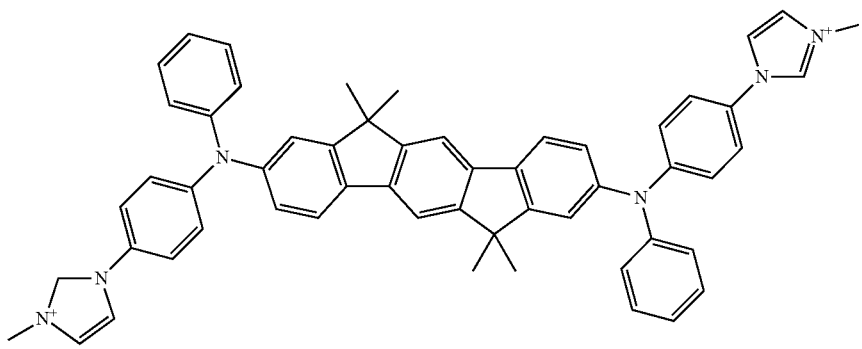
Formula (150)

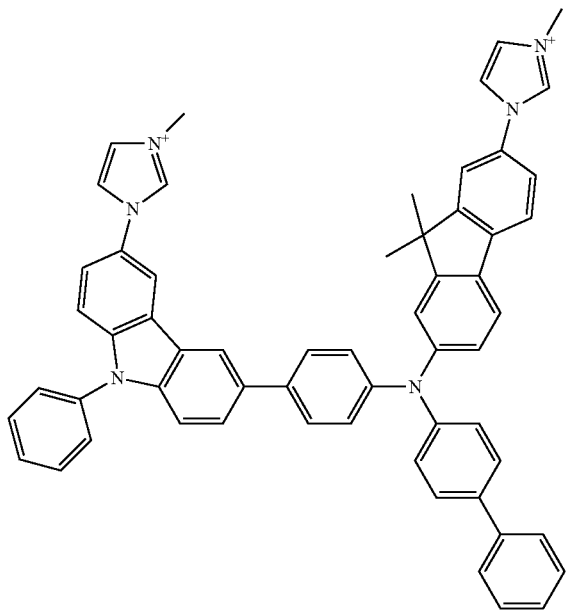
Formula (151)
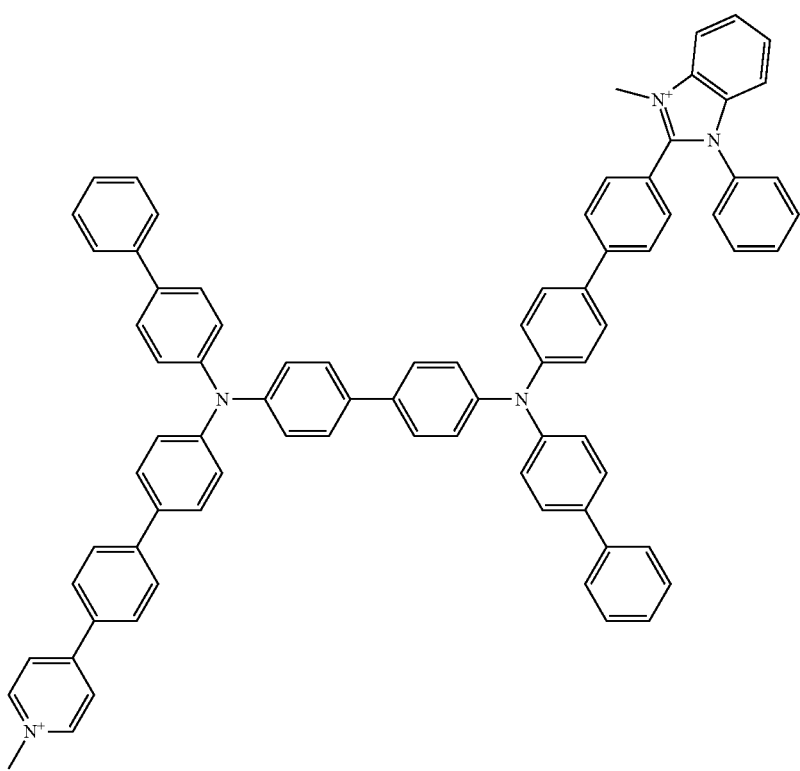
Formula (152)

-continued
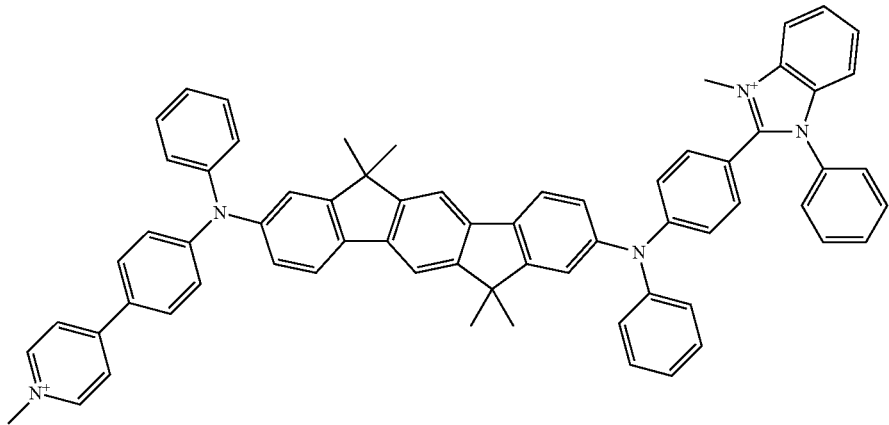
Formula (153)
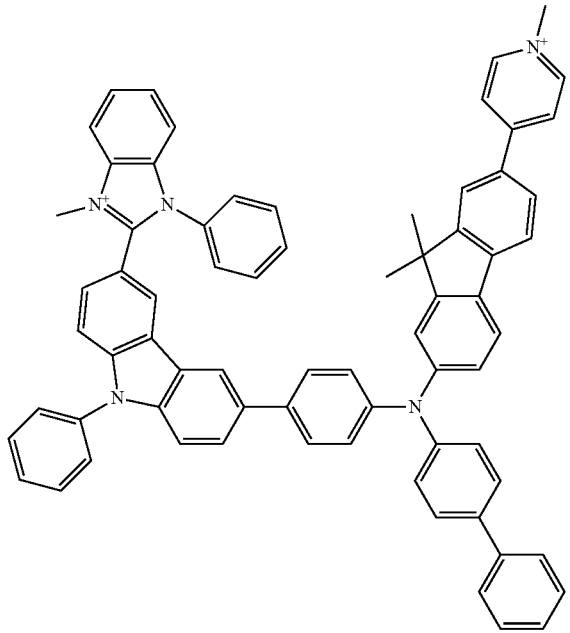
Formula (154)

Formula (155)
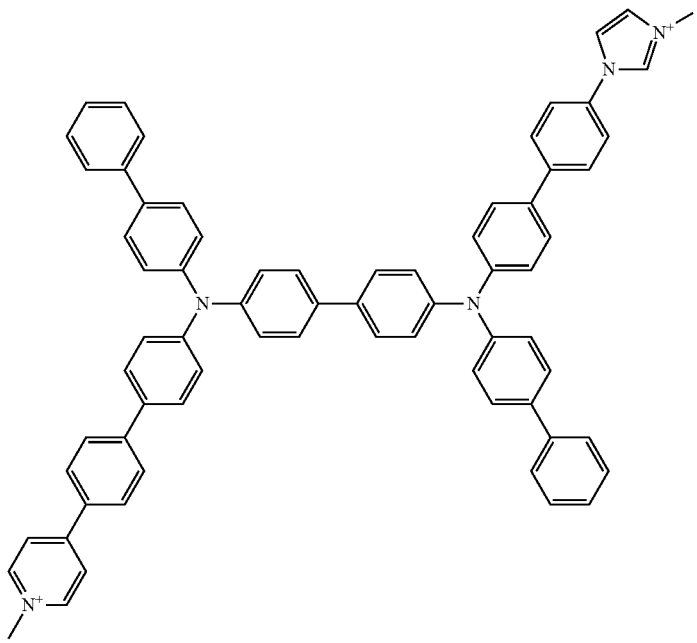
Formula (156)
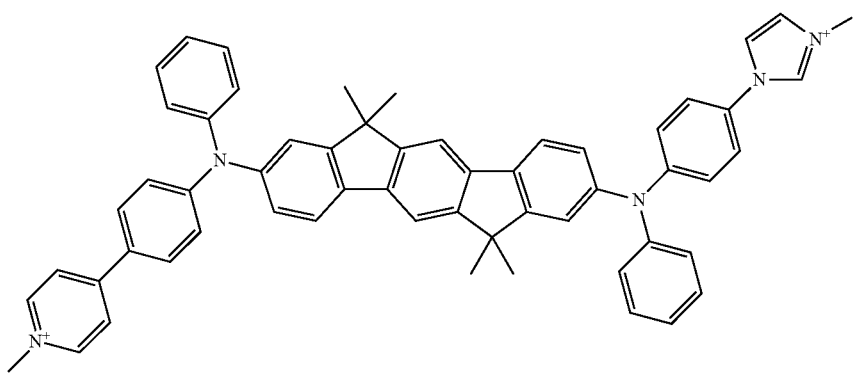
Formula (157)
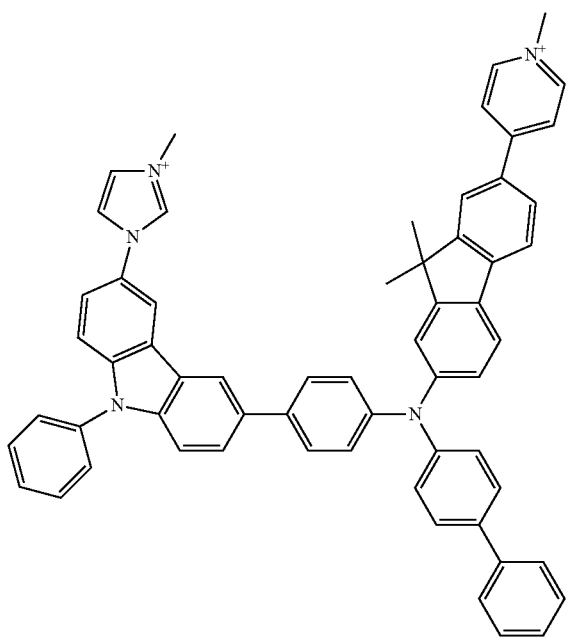

Formula (158)
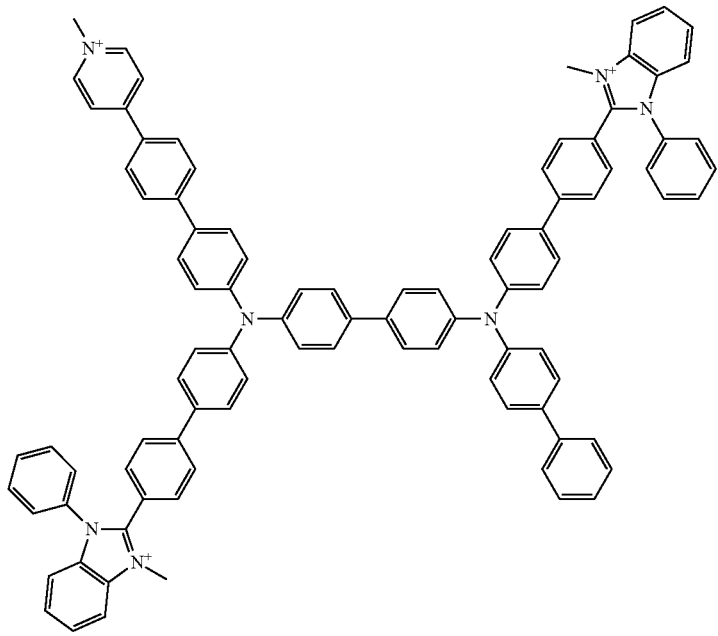
Formula (159)
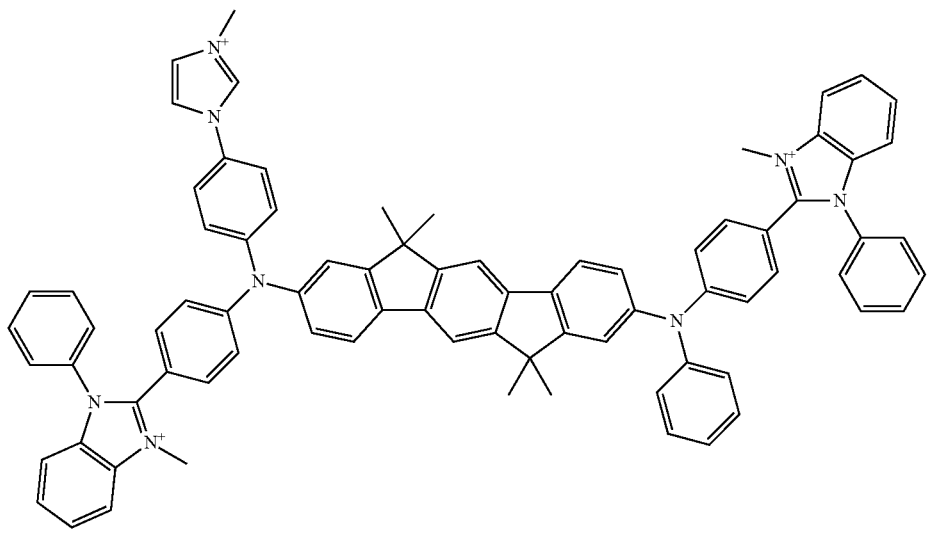

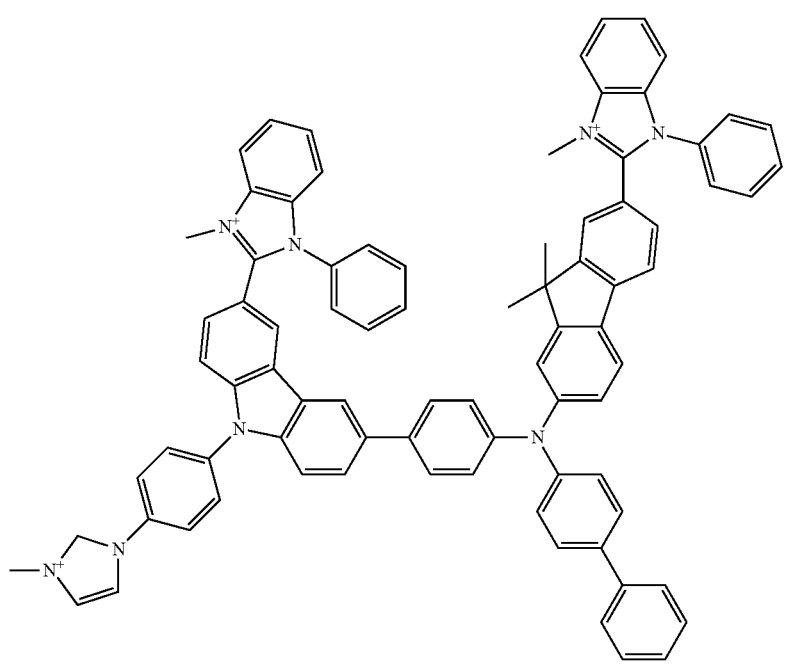
Formula (160)
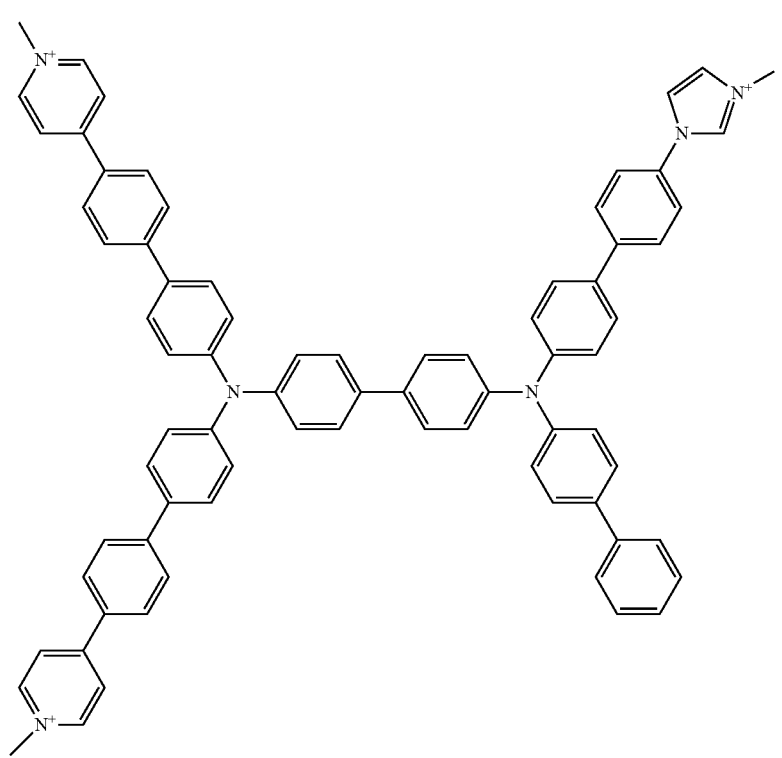
Formula (161)

Formula (162)
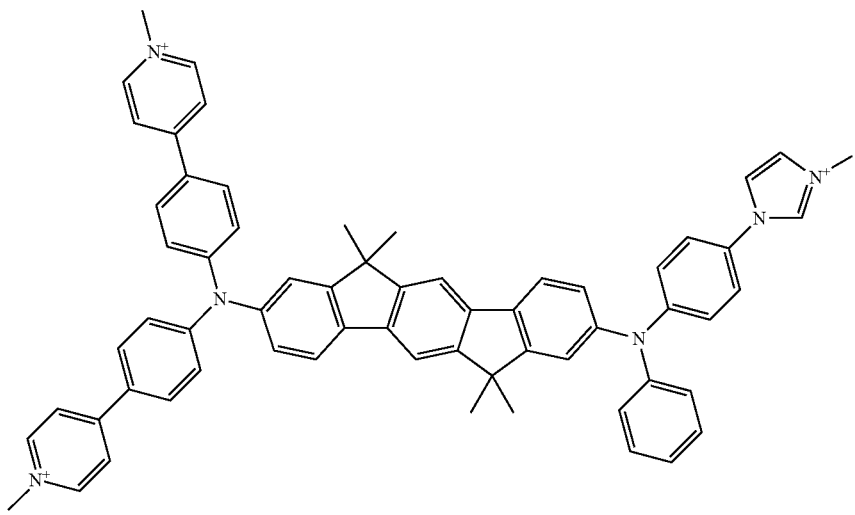
Formula (163)
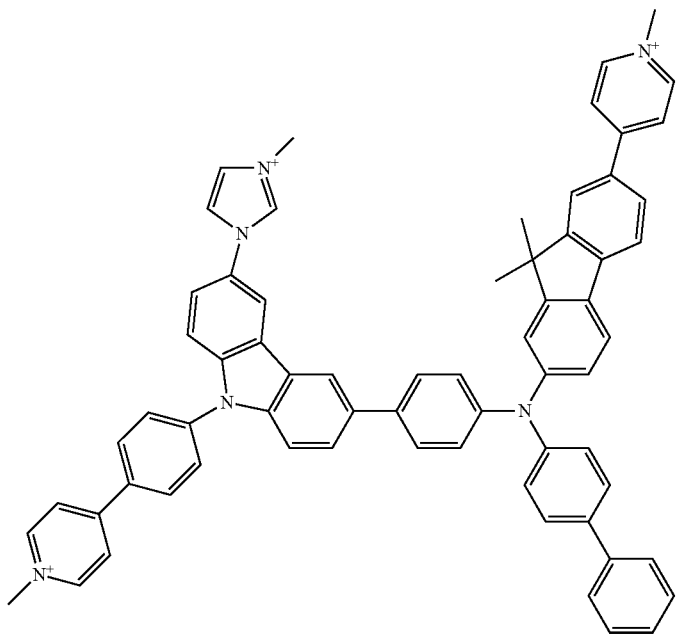
Formula (164)
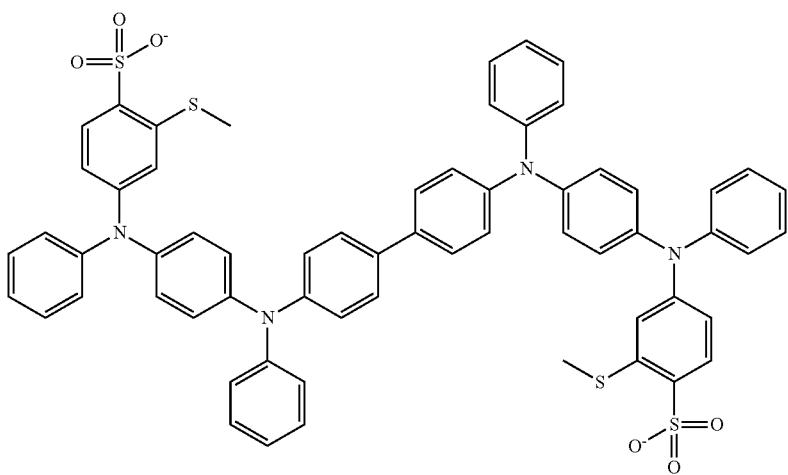

-continued
Formula (165)
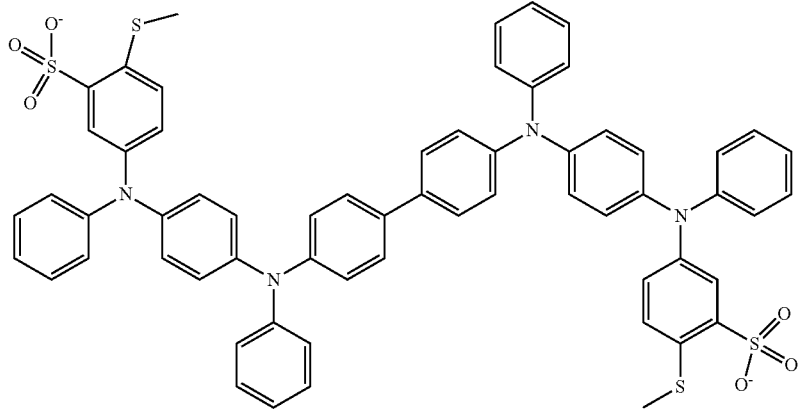
Formula (166)
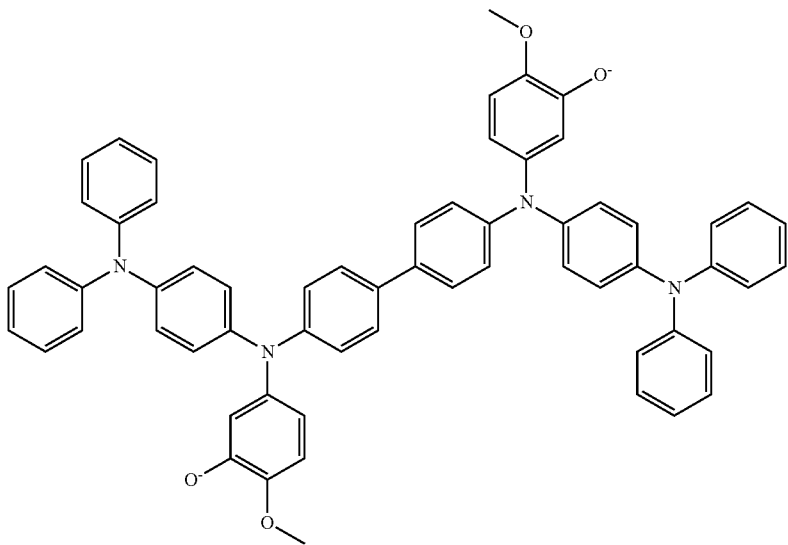
Formula (167)
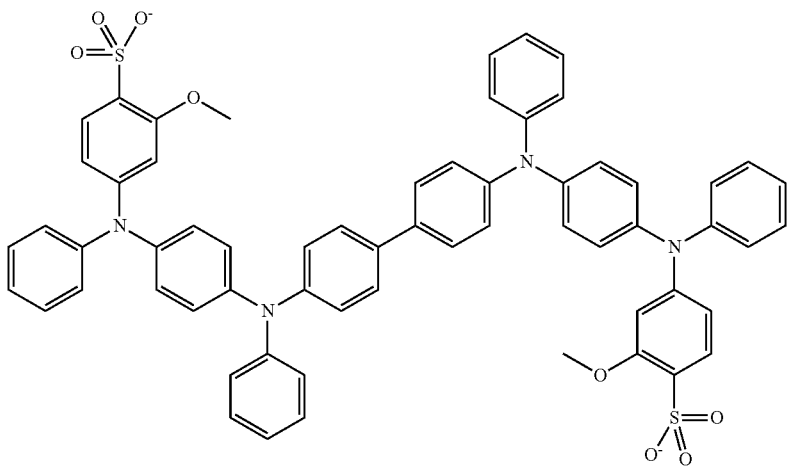

Formula (168)
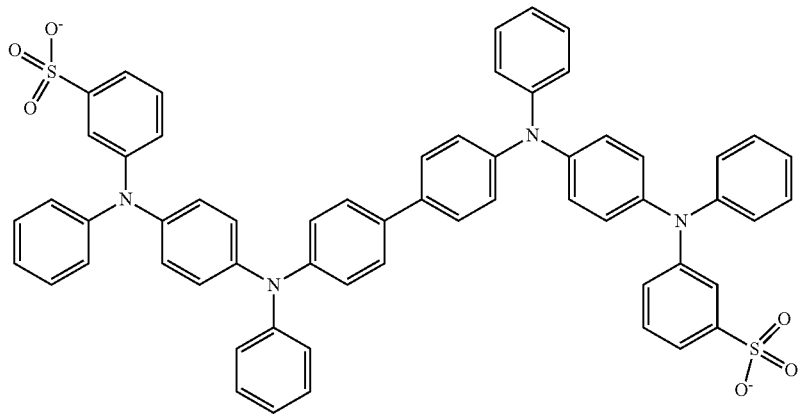
Formula (169)
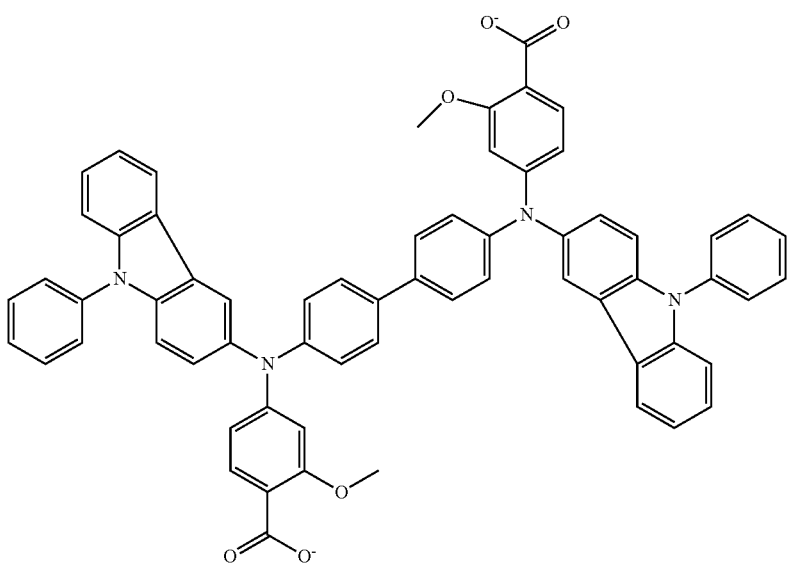
Formula (170)
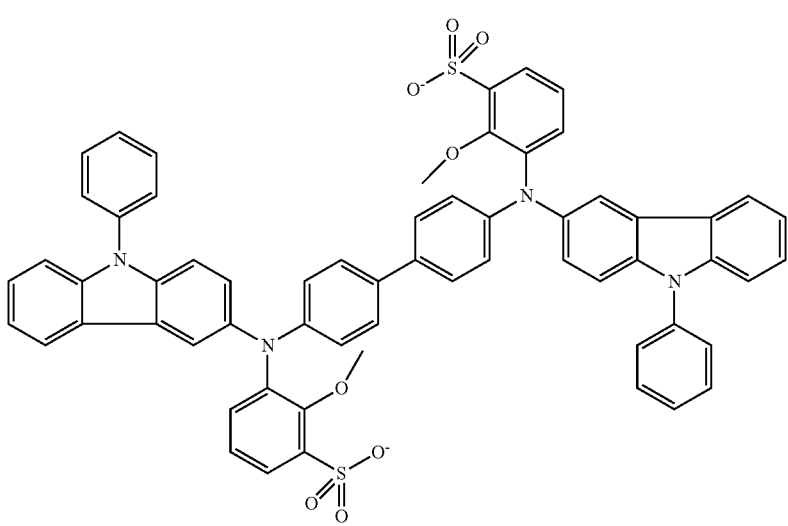

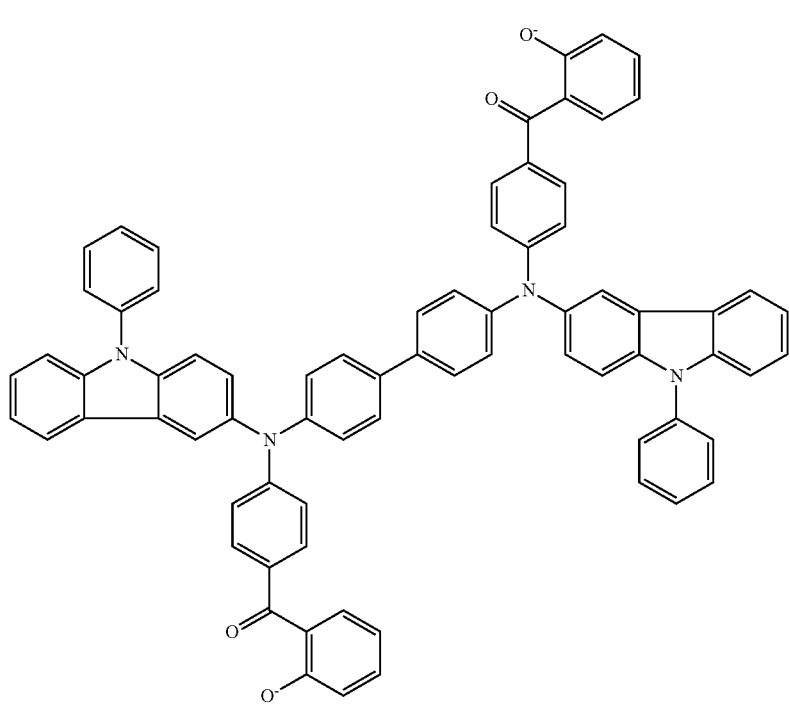
Formula (171)
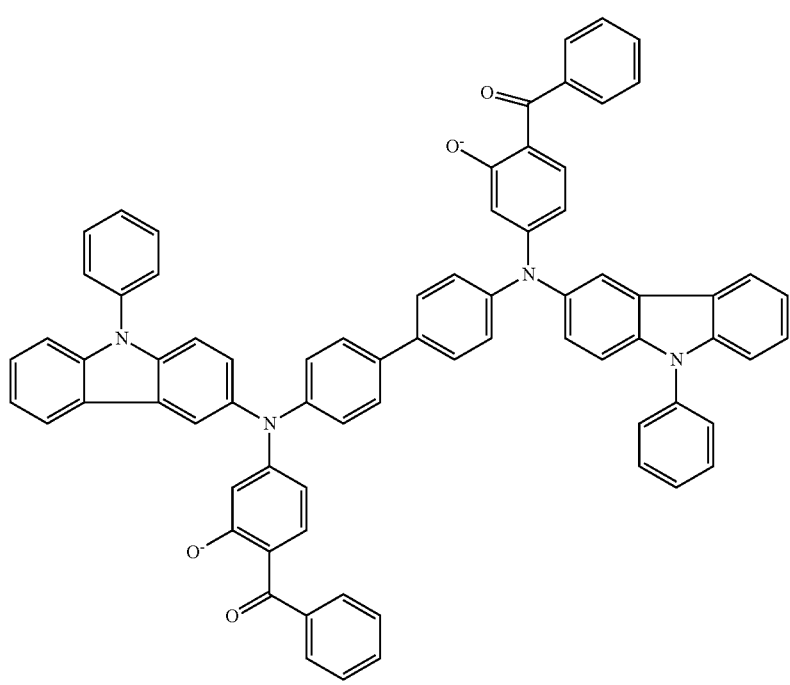
Formula (172)

Formula (173)
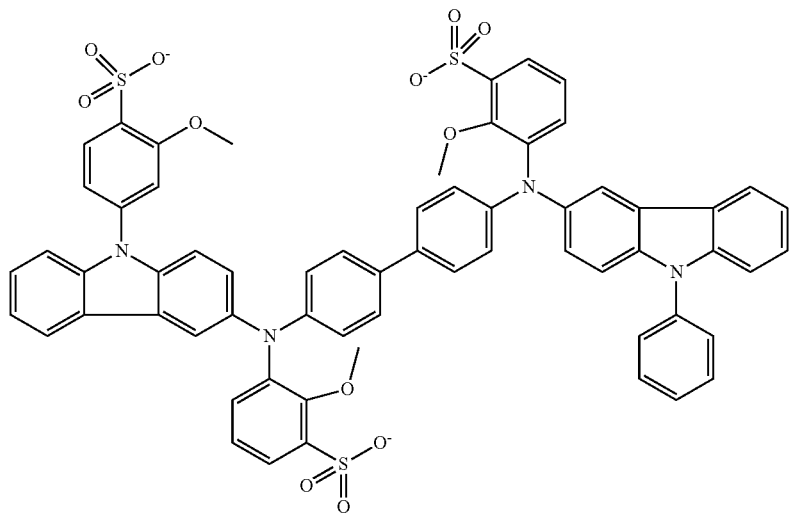
Formula (174)
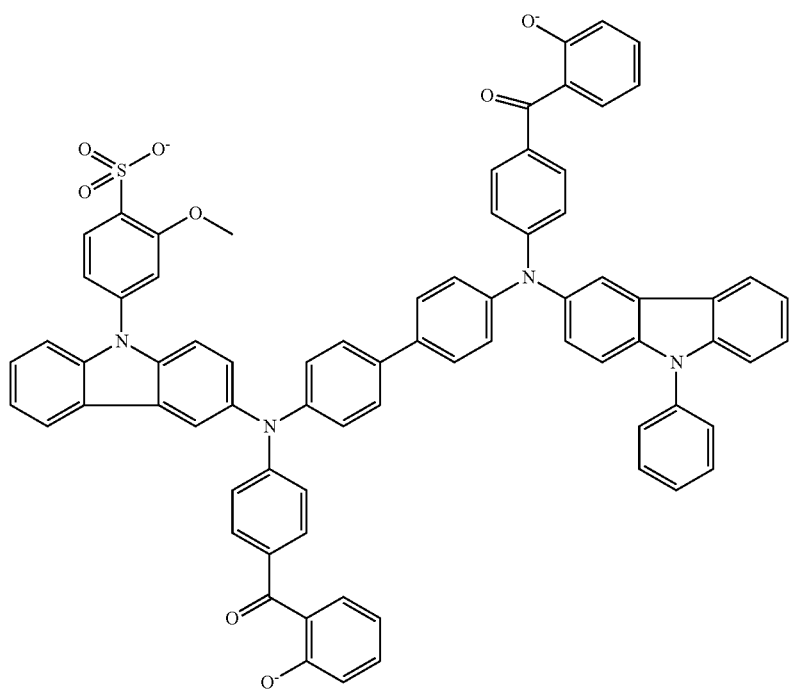

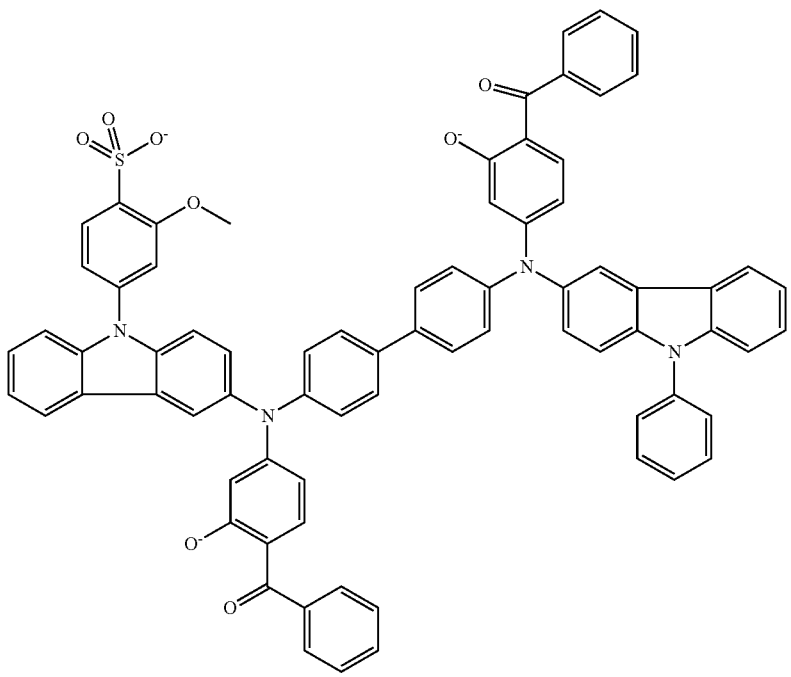

Formula (175)

A general synthesis route for obtaining such compounds is provided below.

In another embodiment of the present invention the multi-charged cation or anion M in compound of formula (1) comprises an electron injection group or electron transport group. In this case the multi-charged organic cation or anion M acts as electron injection material (EIM) or electron transport material (ETM). That is, the electron injection group or the electron transport group gives the organic ionic compound of formula (1) the ability to inject or transport electrons within the organic ionic compound. An ETM is characterized in that it is a material or unit capable of transporting electrons injected from an electron injection material or an cathode. In many cases, EIM can function also as ETM, depending on the adjacent layer.

The uncharged ETMs and EIMs listed below can also be employed as non-ionic organic functional material in the compositions according to the present invention.

In principle any ETM known to the skilled one in the art of OLED can be included as electron transport group in the M of formula (1). Further to ETM mentioned elsewhere herein, suitable ETMs are selected from imidazole, pyridine, pyrimidine, pyridazine, pyrazine, oxadiazole, chinoline, chinoxaline, anthracene, benzanthracene, pyrene, perylene, benzimidazole, triazine, ketones, phosphinoxide, phenazine, phenanthroline, triaryl borane and derivatives thereof and O-, S- or N-containing heterocycles. Preferably the ETM has a LUMO at an energy level of less than −1.9 eV, compared to the energy level in vacuum.

Further preferred suitable ETMs are selected from imidazoles, pyridines, pyrimidines, pyridazines, pyrazines, oxadiazoles, chinolines, chinoxalines, anthracenes, benzanthracenes, pyrenes, perylenes, benzimidazoles, triazines, ketones, phosphinoxides, phenazines, phenanthrolines, and triarylboranes.

Further suitable ETMs are selected from metal chelates of 8-hydroxyquinoline (q) (for example Liq, Alq$_3$, Gaq$_3$, Mgq$_2$), Balq, 4-aza-phenanthrene-5-ol/Be complexes (U.S. Pat. No. 5,529,853 A; e.g. formula (176)), butadiene derivatives (U.S. Pat. No. 4,356,429), heterocyclic optical brighteners (U.S. Pat. No. 4,539,507), benzazoles, such as, for example, 1,3,5-tris(2-N-phenylbenzimidazolyl)benzene (TPBI) (U.S. Pat. No. 5,766,779, formula (177)), 1,3,5-triazines, pyrenes, anthracenes, tetracenes, fluorenes, spirobifluorenes, dendrimers, tetracenes, for example rubrene derivatives, 1,10-phenanthroline derivatives (JP 2003/115387, JP 2004/311184, JP 2001/267080, WO 2002/043449), silacyl-cyclopentadiene derivatives (EP 1480280, EP 1478032, EP 1469533), pyridine derivatives (JP 2004/200162 Kodak), phenanthrolines, for example BCP and Bphen, also a number of phenanthrolines bonded via biphenyl or other aromatic groups (US 2007/0252517 A1) or phenanthrolines bonded to anthracene (US 2007/0122656 A1, e.g. formulae (178) and (179)), 1,3,4-oxadiazoles, for example formula (180), triazoles, for example formula (181), triarylboranes, for example also with Si, benzimidazole derivatives and other N heterocyclic compounds (cf. US 2007/0273272 A1), silacyclopentadiene derivatives, borane derivatives, Ga oxinoid complexes.

Preference is given to 2,9,10-substituted anthracenes (with 1- or 2-naphthyl and 4- or 3-biphenyl) or molecules which contain two anthracene units (US 2008/0193796 A1) (formulae (176) to (181)).

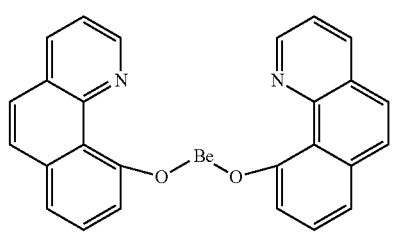

Formula (176)

Formula (177)
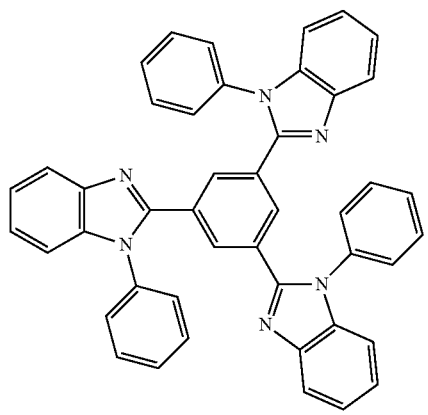
Formula (182)
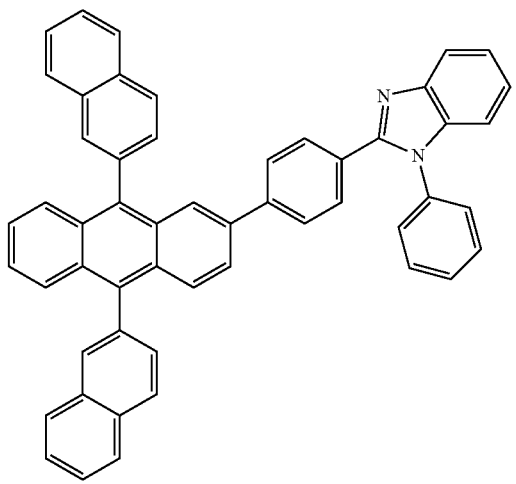
Formula (178)
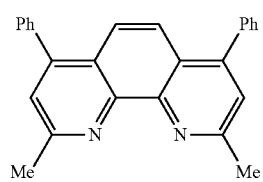
Formula (179)
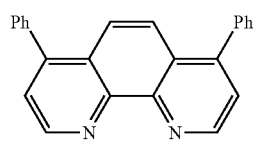
Formula (183)
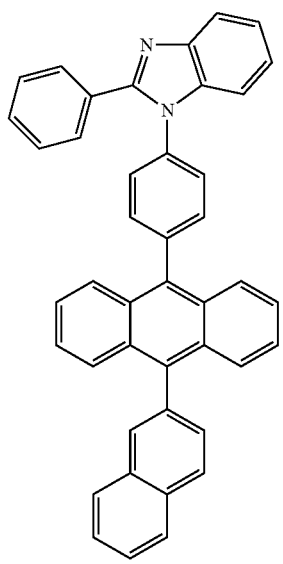
Formula (180)
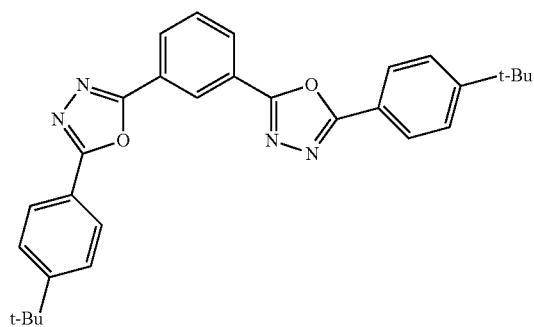
Formula (181)
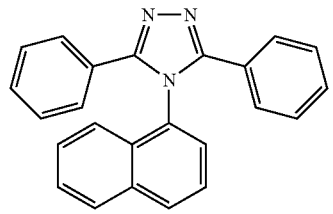
Formula (184)
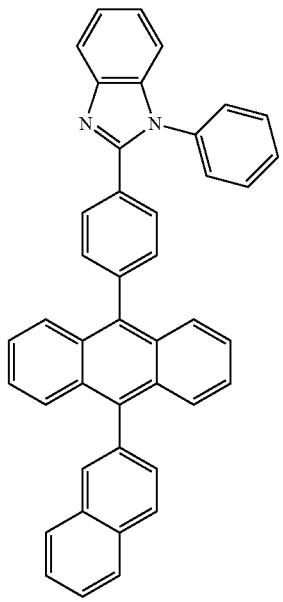
Preference is likewise given to anthracene-benzimidazole derivatives, such as, for example, the compounds of formulae (182) to (184), and as disclosed in, e.g., U.S. Pat. No. 6,878,469 B2, US 2006/147747 A, and EP 1551206 A1.

In principle any EIM known to one skilled in the art of OLED can be included as electron injection group in the M of formula (1). Further to EIM mentioned elsewhere herein, suitable EIM comprises at least one organic compound selected from metal complexes of 8-hydroxyquinoline, heterocyclic organic compounds, fluorenones, fluorenylidene methane, perylenetetracarboxylic acid, anthraquinone dimethanes, diphenoquinones, anthrones, anthraquinonediethylene-diamines, isomers and derivates thereof can be used according to the invention.

Non-transition-metal complexes of 8-hydroxyquinoline, such as, for example, Alq$_3$ and Gaq$_3$, can be used as EIM for the functional organic group in the organic ionic compound according to the present invention.

Heterocyclic organic compounds, such as, for example, 1,10-phenanthroline derivatives, benzimidazoles, thiopyran dioxides, oxazoles, triazoles, imidazoles or oxadiazoles, are likewise suitable. Examples of suitable five-membered rings containing nitrogen are oxazoles, thiazoles, oxadiazoles, thiadiazoles, triazoles, and compounds which are disclosed in US 2008/0102311 A1.

Preferred EIMs are selected from compounds with the formulae (185) to (187), which may be substituted or unsubstituted.

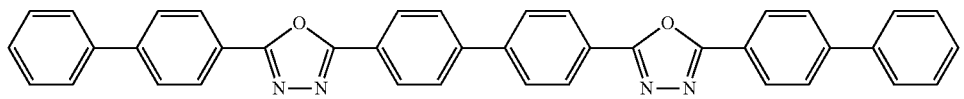
Formula (185)

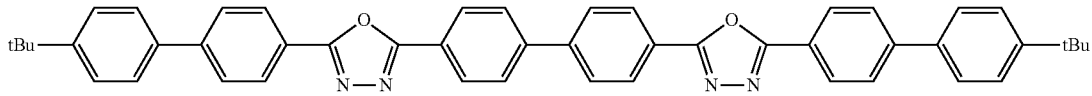
Formula (186)

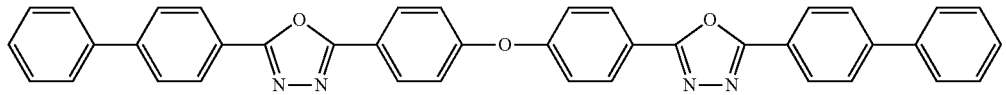
Formula (187)

Organic compounds, such as fluorenones, fluorenylidene methane, perylenetetracarboxylic acid, anthraquinone dimethanes, diphenoquinones, anthrones and anthraquinonediethylenediamines, can also be employed, for example as ETM or EIM (formulae (188) and (189)).

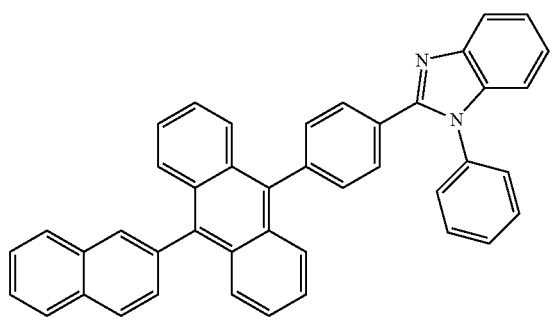
Formula (188)

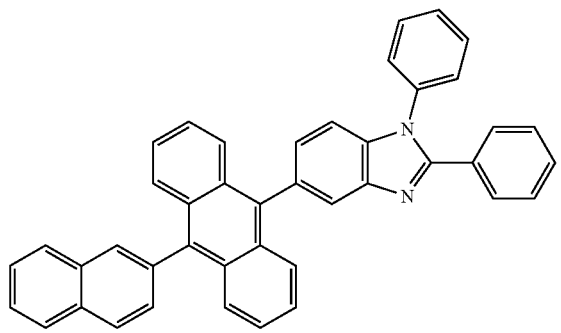
Formula (189)

In case the above mentioned examples of ETM and EIM compounds are ionic compounds they may act as the multi-charged organic cation or anion M itself. In this case M is consisting of the functional organic group and the functional organic group itself is M.

In case the above mentioned examples of ETM and EIM compounds are non-ionic compounds they are part of the multi-charged organic cation or anion M. In this case the ETM and EIM compounds are the above-mentioned functional organic group comprised in the multi-charged organic cation or anion M and are bound to the charged part of M in that at least two hydrogen atoms are not present in the above mentioned compounds and the compounds are connected to the charged parts of M via the positions where the hydrogen atoms are not present.

The following charged compounds are particularly preferred as multi-charged organic cation or anion M comprising an electron transport or electron injection group as functional organic group:

Examples for suitable mulitcharged cation or anion comprising an ETM or EIM group are listed as follows, wherein BF$_4^-$ and PF$_6^-$ can be replaced by other anion. Further suitable examples can be readily made by the combination of the ETM and/or EIM groups as described above and the anion and cation groups as described below.

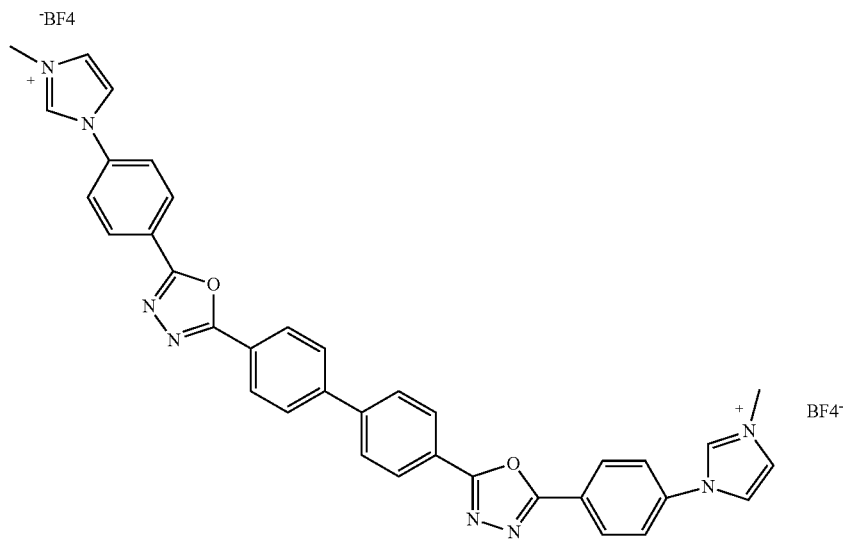
Formula (190)
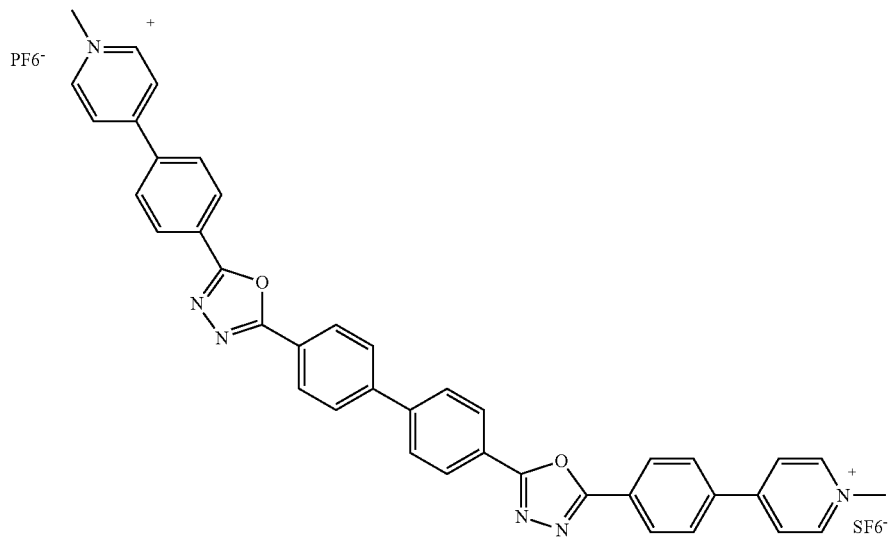
Formula (191)
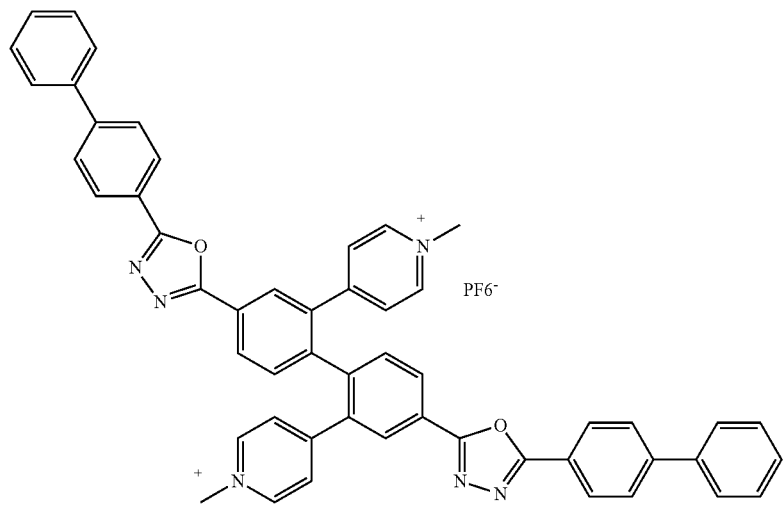
Formula (192)

Formula (193)
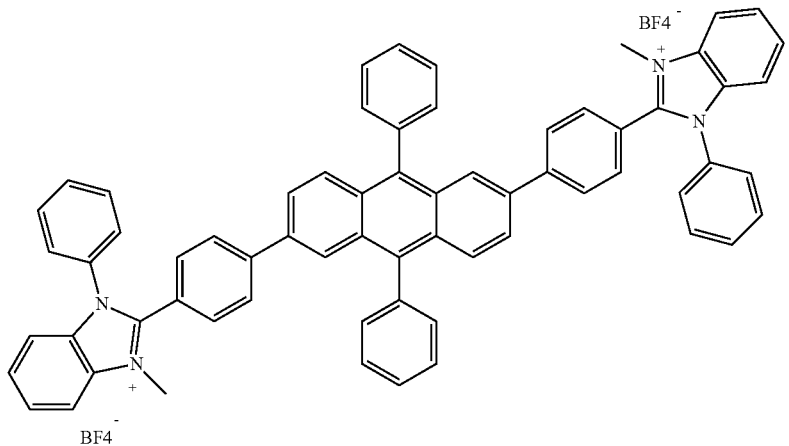
Formula (194)
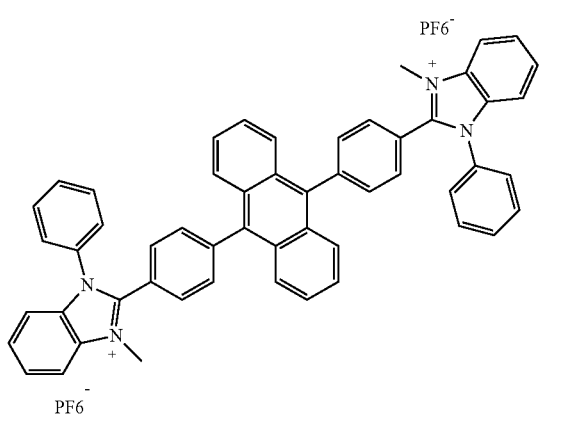
Formula (195)
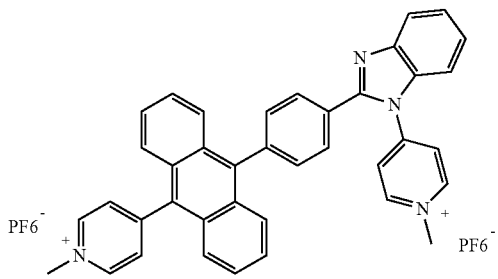
Formula (196)
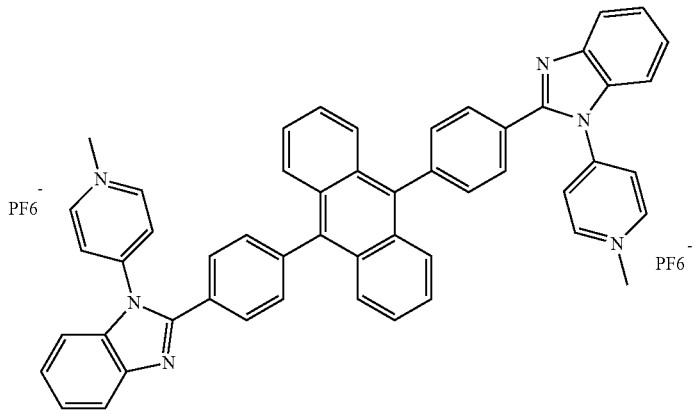

-continued
Formula (197)
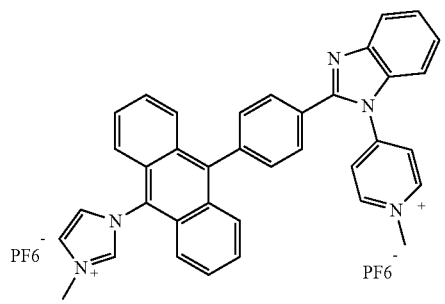
Formula (198)
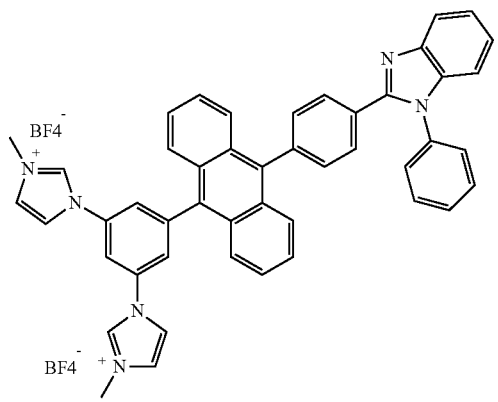
Formula (199)
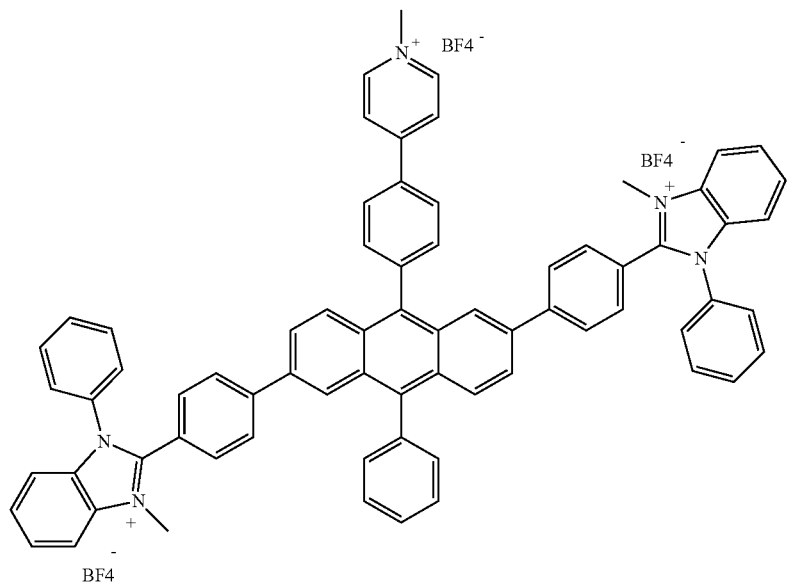
Formula (200)
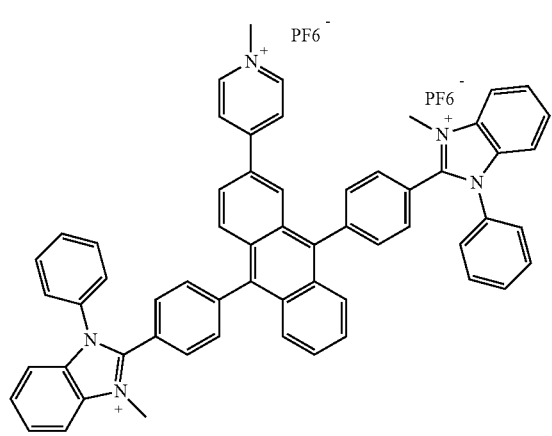
Formula (201)
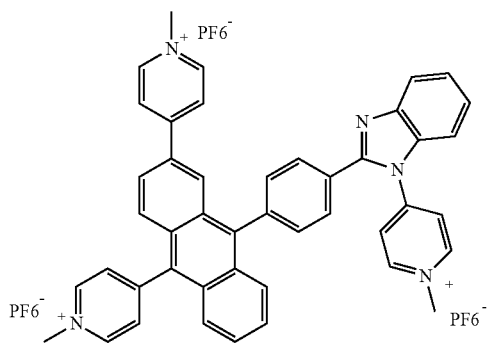

-continued
Formula (205)
Formula (206)
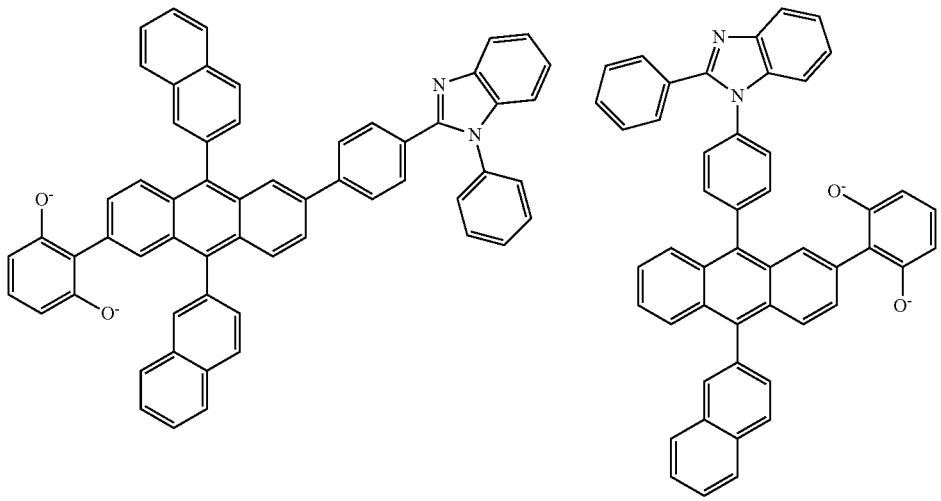
Formula (207)
Formula (208)
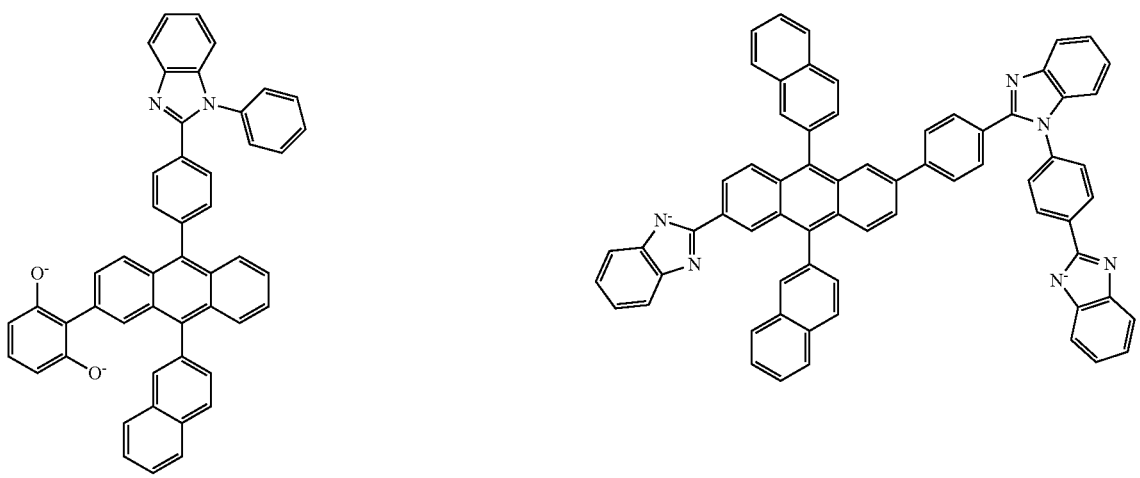
Formula (209)
Formula (210)
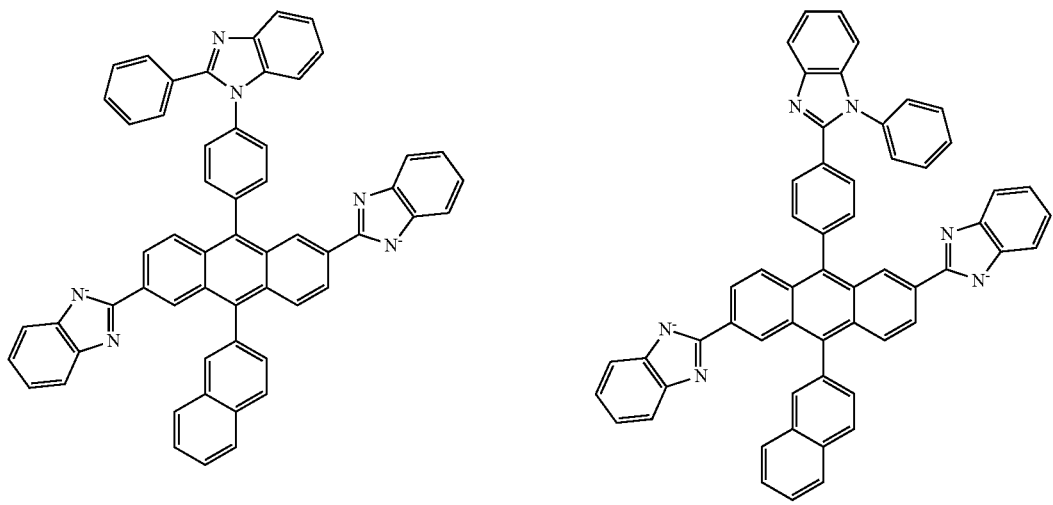

-continued
Formula (211)
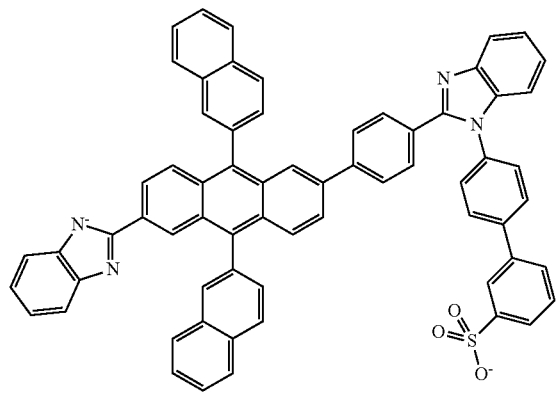
Formula (212)
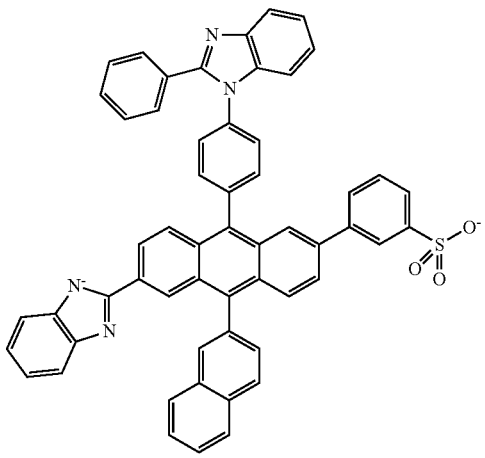
Formula (213)
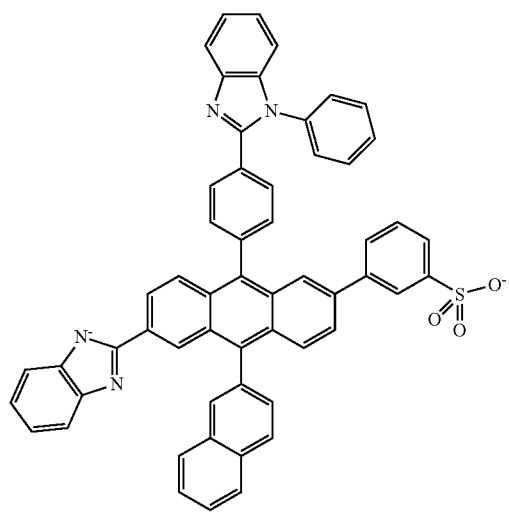
Formula (214)
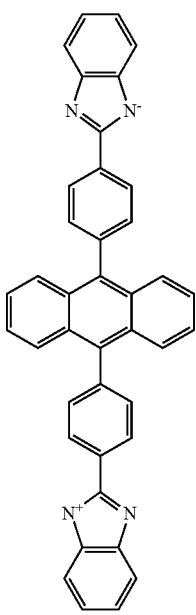

-continued
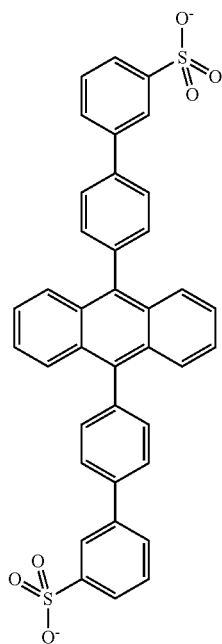
Formula (215)
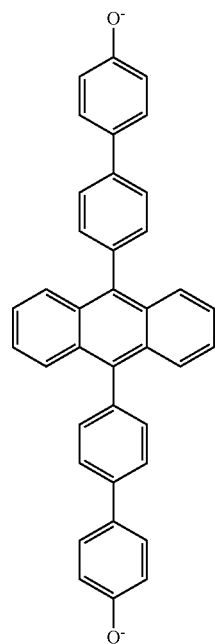
Formula (216)
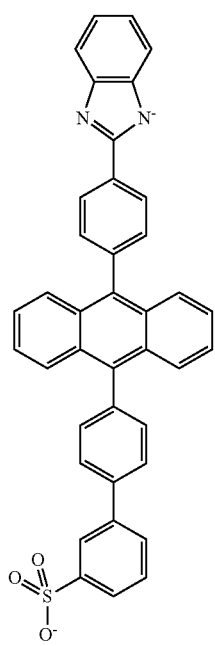
Formula (217)
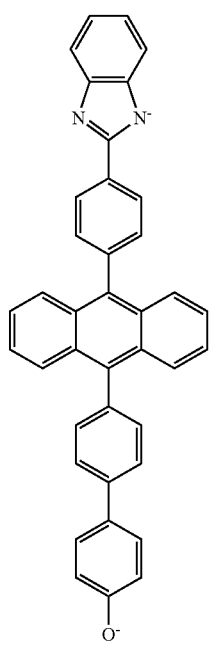
Formula (218)

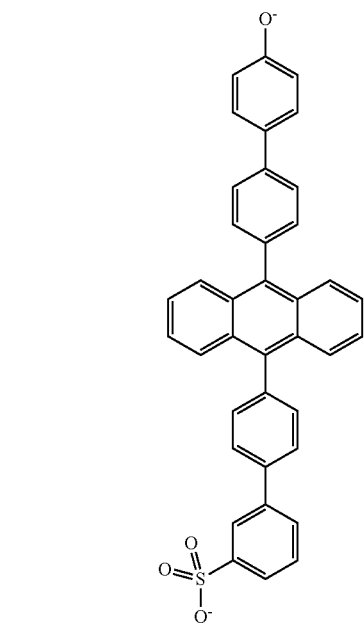

Formula (219)

A general synthesis route for obtaining such compounds is provided below.

It is further subject of the present invention that all embodiments above with regard to the definitions of the organic ion M may be combined with the definitions and preferred definitions of elements of the device and the other embodiments of the present invention other than with regard to the definition of the organic ion M.

Preference is also given to a composition, characterized in that $(M)^{m+/-}$ in compound of formula (1) is a non-functional ion, i.e. is not a fluorescence or phosphorescence emitter, not a host, not a hole injecting material, not a hole transporting material, not an electron injecting material or not an electron transporting material. As further outlined below the term non-functional also excludes the function as hole and/or electron blocking group/compound.

Particular preference is given to a composition according to the invention, characterized in that $(M)^{m+/-}$ in compound of formula (1) is a non-functional ion and wherein the composition further comprises 4, preferably 3, particularly preferably 2, and very particularly preferably 1 further non-ionic organic functional compound selected from host materials, phosphorescent emitters, fluorescent emitters, hole transporting materials (HTM), hole injecting materials (HIM), electron transporting materials (ETM), and electron injecting materials (EIM), preferably phosphorescent emitters, fluorescent emitters and host materials.

In a particularly preferred embodiment of the present invention said composition comprises a compound with formula (1), characterized in that $(M)^{m+/-}$ in compound of formula (1) is a non-functional ion and wherein the composition further three further non-ionic organic functional material selected from host (matrix) materials and phosphorescent emitters, preferably two host (matrix) materials and one phosphorescent emitter.

In another particularly preferred embodiment of the present invention said composition comprises a compound with formula (1), characterized in that $(M)^{m+/-}$ in compound of formula (1) is a non-functional ion and wherein the composition further three further non-ionic organic functional material selected from host materials and fluorescent emitters, preferably two host materials and one fluorescent emitter.

In case two or more host materials are used in one composition the second and any further host material is sometimes called co-host.

In yet another further preferred embodiment $(M)^{m+/-}$ in compound of formula (1) comprises an aliphatic hydrocarbyl group, preferably selected from linear or branched or cyclic alkyl, alkoxy, thioalkoxy, or amino group with 1 to 40 carbon atoms, and/or aromatic or heteroaromatic 5- or 6-membered rings.

In one embodiment, the said non-functional group or compound consists of aliphatic group, wherein at least one of the hydrogen is replaced by one of the charged groups as described below.

The aliphatic group/compound meant herein is an acyclic or cyclic, non-aromatic carbon group/compound, optionally comprising one or more hetero-atoms for example N, O, S, P, Si, Se, As, Te or Ge.

An aliphatic group comprising a chain of 3 or more C atoms may be linear, branched and/or cyclic. Preferred aliphatic groups include alkyl, alkoxy, alkylcarbonyl, alkoxycarbonyl, alkylcarbonyloxy and alkoxycarbonyloxy, each of which is optionally substituted and has 1 to 40, preferably 1 to 25, particularly preferably 1 to 18 C atoms.

The aliphatic group may be a saturated or unsaturated acyclic group, or a saturated or unsaturated cyclic group. In certain embodiment, unsaturated acyclic or cyclic groups may be used, especially alkenyl and alkynyl groups (especially ethynyl). Where the $C_1$-$C_{40}$ aliphatic group is acyclic, the group may be linear or branched.

The $C_1$-$C_{40}$ aliphatic group includes for example: $C_1$-$C_{40}$ alkyl, $C_2$-$C_{40}$ alkenyl, $C_2$-$C_{40}$ alkynyl, $C_3$-$C_{40}$ allyl group, $C_4$-$C_{40}$ alkyldienyl, $C_4$-$C_{40}$ polyenyl, $C_6$-$C_{40}$ alkylaryloxy, $C_6$-$C_{40}$ arylalkyloxy, $C_4$-$C_{40}$ cycloalkyl, $C_4$-$C_{40}$ cycloalkenyl, and the like. Very preferred are $C_1$-$C_{20}$ alkyl, $C_2$-$C_{20}$ alkenyl, $C_2$-$C_{20}$ alkynyl, $C_3$-$C_{20}$ allyl, $C_4$-$C_{20}$ alkyldienyl.

Further preferred aliphatic groups include straight-chain, branched or cyclic alkyl with 1 to 40, preferably 1 to 25 C-atoms, which is unsubstituted, mono- or polysubstituted by F, Cl, Br, I or CN, and wherein one or more non-adjacent CH$_2$ groups are optionally replaced, in each case independently from one another, by —O—, —S—, —NH—, —NR$^0$—, —SiR$^0$R$^{00}$—, —, —CO—, —COO—, —OCO—, —O—CO—O—, —S—CO—, —CO—S—, —CO—NR$^0$—, —NR$^0$—CO—, —NR$^0$—CO—NR$^{00}$—, —CX$^1$=CX$^2$— or —C≡C— in such a manner that O and/or S atoms are not linked directly to one another, with R$^0$ and R$^{00}$ having one of the meanings given as described above and below and X$^1$ and X$^2$ being independently of each other H, F, Cl or CN. R$^0$ and R$^{00}$ are preferably selected from H, straight-chain or branched alkyl with 1 to 12 C atoms.

Halogen is F, Cl, Br or I.

Preferred alkyl groups include, without limitation, methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, 2-ethylhexyl, n-heptyl, cycloheptyl, n-octyl, cyclooctyl, dodecanyl, trifluoromethyl, perfluoro-n-butyl, 2,2,2-trifluoroethyl, perfluorooctyl, perfluorohexyl etc.

Preferred alkenyl groups include, without limitation, ethenyl, propenyl, butenyl, pentenyl, cyclopentenyl, hexenyl, cyclohexenyl, heptenyl, cycloheptenyl, octenyl, cyclooctenyl etc.

Preferred alkynyl groups include, without limitation, ethynyl, propynyl, butynyl, pentynyl, hexynyl, octynyl etc.

Preferred alkoxy groups include, without limitation, methoxy, ethoxy, 2-methoxyethoxy, n-propoxy, i-propoxy, n-butoxy, i-butoxy, s-butoxy, t-butoxy, 2-methylbutoxy, n-pentoxy, n-hexoxy, n-heptoxy, n-octoxy etc.

Preferred amino groups include, without limitation, dimethylamino, methylamino, methylphenylamino, phenylamino, etc.

In yet another preferred embodiment said aliphatic group/compound is saturated.

Usually organic functional compound or group suitable for organic electronic devices comprises a conjugated π-system which is big enough to get suitable energy levels, for example highest occupied molecular orbital (HOMO) and/or lowest unoccupied molecular orbital (LUMO). The so-called "big enough conjugated π-system" can usually be realized in a system comprising at least two aromatic or a heteroaromtic rings, wherein the said at least two rings are directly bound with each other, e.g. either by a single bond or by fusing together.

The present invention also relates to compositions comprising at least one compound according to formula (1) characterized in that the non-functional group/compound in M comprises a 5 or 6-member aromatic or heteroaromatic ring substituted by at least one aliphatic group as described above, wherein at least one of the hydrogen is replaced by one of the charged groups as described below.

The said 5 or 6 member ring can be preferably selected from:

Formula (220)

Formula (221)

Formula (222)

Formula (223)

Formula (224)

Formula (225)

Formula (226)

Formula (227)

Formula (228)

Formula (229)

Formula (230)

Formula (231)

Formula (232)

Formula (233)

Formula (234)

Examples for suitable multicharged cation or anion comprising a non-functional organic group are listed as follows. Further suitable examples can be readily made by the combination of the non-functional organic groups as described above and the anion and cation groups as described below.
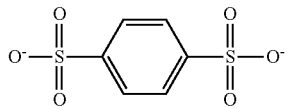
Formula (235)
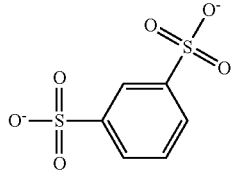
Formula (236)
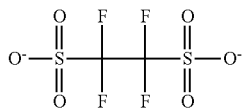
Formula (237)
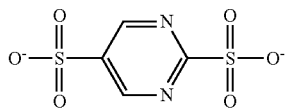
Formula (238)
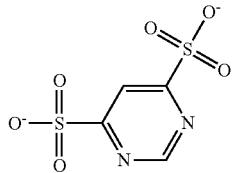
Formula (239)
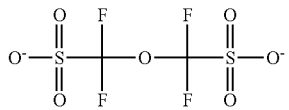
Formula (240)
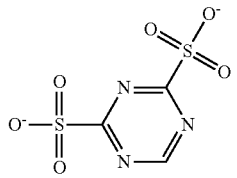
Formula (241)
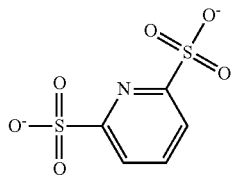
Formula (242)
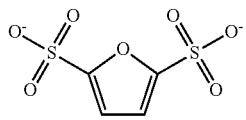
Formula (243)
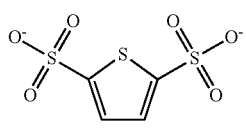
Formula (244)
-continued
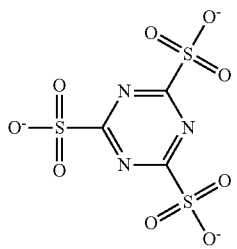
Formula (245)
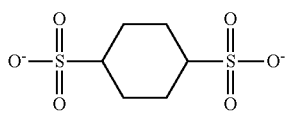
Formula (246)
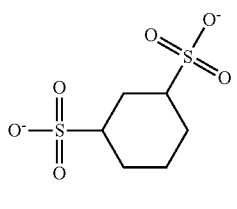
Formula (247)
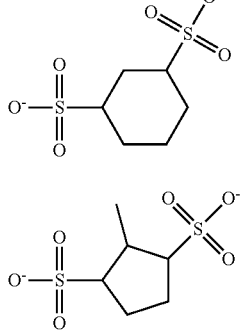
Formula (248)
Formula (249)
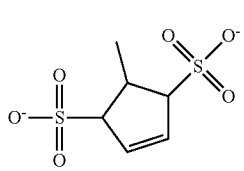
Formula (250)
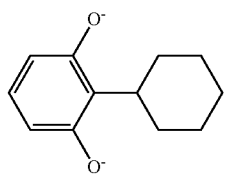
Formula (251)
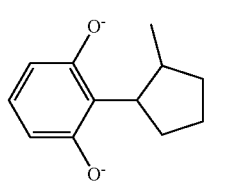
Formula (252)
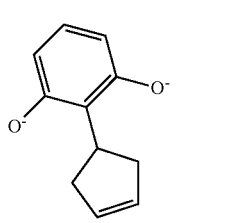
Formula (253)
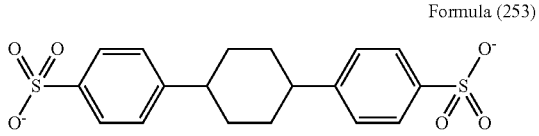

Formula (254)
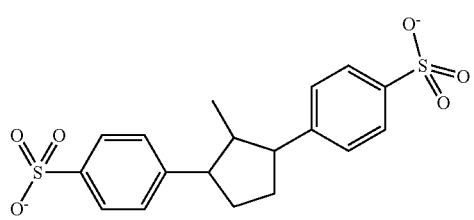
Formula (255)
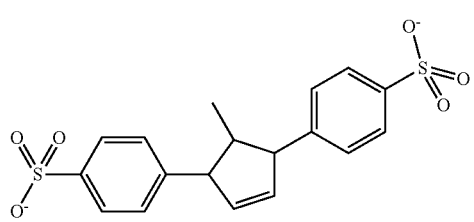
Formula (256)
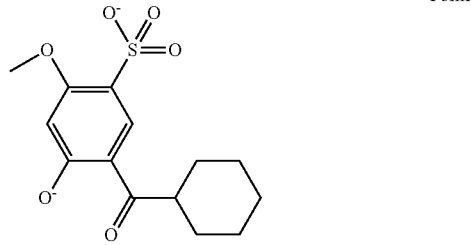
Formula (257)
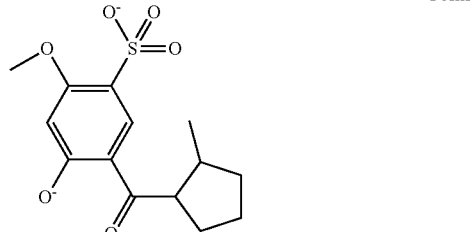
Formula (258)
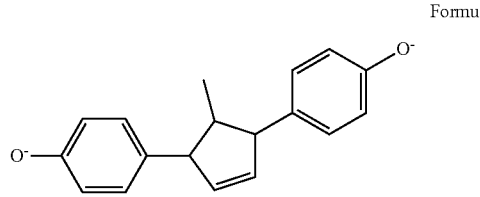
Formula (259)
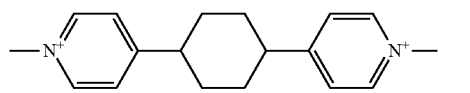
Formula (260)
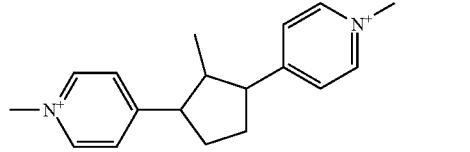
Formula (261)
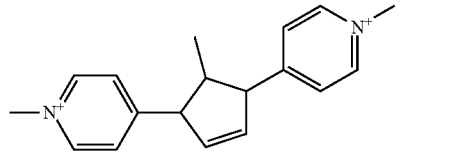
Formula (262)
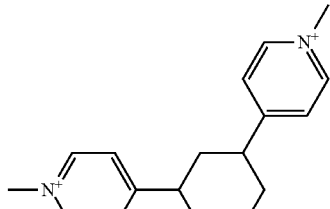
Formula (263)
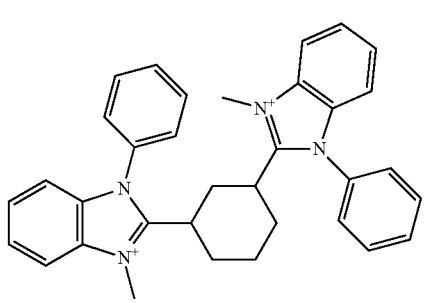
Formula (264)
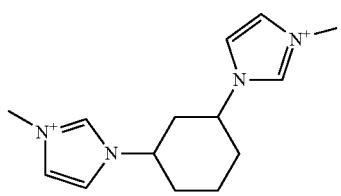
Formula (265)
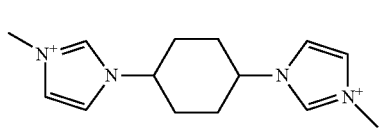
Formula (266)
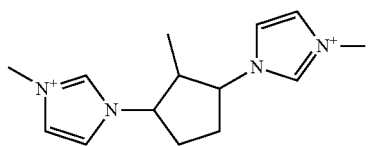
Formula (267)
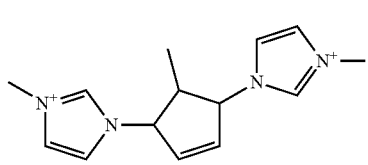
Formula (268)
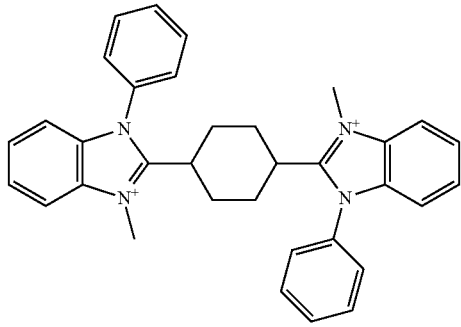

-continued

Formula (269)

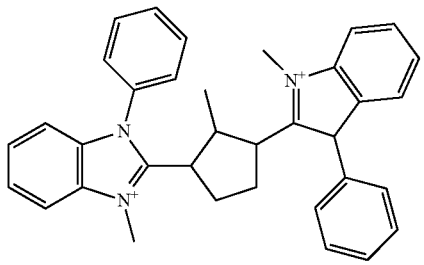

Formula (270)

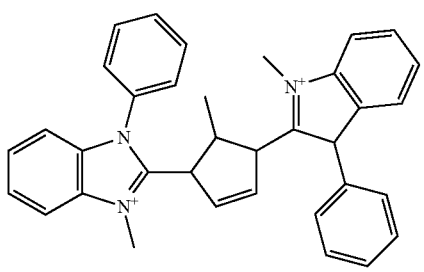

Formula (271)

Formula (272)

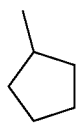

Formula (273)

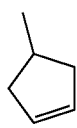

The present invention further relates to a composition, characterized in that $(M)^{m+/-}$ in formula (1) comprises a functional organic group selected from a fluorescence emitting group, preferably a fluorescent polyaromatic compound comprising amine, triarylamine, anthracene, tetracene, indenoperylene, perylene, pyrene, chrysene, decacyclene, coronene, coumarine, isomers and derivatives thereof, a host group, preferably selected from anthracenes, benzanthracenes, ketones, carbazoles, triarylamines, indolocarbazole, indenofluorenes, phenanthrenes, dihydrophenanthrenes, thiophenes, benzothiophene, dibenzothiophene, triazines, phosphine oxides, sulfoxides, sulfones, triazole, oxazole, imidazole isomers and derivatives thereof, a hole injecting or transporting group, preferably selected from aromatic amines, triarylamines, thiophenes, benzothiophene, dibenzothiophene, carbazoles, indolocarbazole, indenofluorenes, phthalocyanines, porphyrines, isomers and derivatives thereof, and an electron injecting or transporting group, preferably selected from imidazole, pyridine, pyrimidine, pyridazine, pyrazine, oxadiazole, chinoline, chinoxaline, anthracene, benzanthracene, pyrene, perylene, benzimidazole, triazine, ketones, phosphinoxide, phenazine, phenanthroline, triaryl borane and derivatives thereof.

In a preferred embodiment, M and N are different in size.

Preference is given to said compositions, characterized in that $(M)^{m+/-}$ in formula (1) has a molecular weight in the range from 6 to 1000 g/mol, preferably in the range from 6 to 800 g/mol, particularly preferably in the range from 6 to 700 g/mol, and very particularly preferably in the range from 6 to 600 g/mol.

Preferably, M is bigger than N. Furthermore, the organic or inorganic cation or anion N is preferably one having a molecular weight in the range from 6 to 1000 g/mol, particularly preferably in the rang from 6 to 800 g/mol and very particularly preferably in the range from 6 to 600 g/mol. In a further embodiment, the upper limit of the range of the molecular weight of N should not be exceeded, preferably if the organic ionic compound according to the invention is to be used in OLECs or solar cells, since molecules with a lower molecular weight may act as mobile ions in layers of an OLEC as charge transporting compounds.

Preferably, the organic ionic compound of formula (1) is solid at room temperature and, particularly preferably, the said ionic material is solid at room temperature and getting softer between 30 to 40° C.

Further preference is given to said compositions, characterized in that M is a cation and N is an anion which is selected from $[HSO_4]^-$, $[SO_4]^{2-}$, $[NO_3]^-$, $[BF_4]^-$, $[(R_F)BF_3]^-$, $[(R_F)_2BF_2]^-$, $[(R_F)_3BF]^-$, $[(R_F)_4B]^-$, $[B(CN)_4]^-$, $[PO_4]^{3-}$, $[HPO_4]^{2-}$, $[H_2PO_4]^-$, $[Alkyl-OPO_3]^{2-}$, $[(Alkyl-O)_2PO_2]^-$, $[Alkyl-PO_3]^{2-}$, $[R_FPO_3]^{2-}$, $[(Alkyl)_2PO_2]^-$, $[(R_F)_2PO_2]^-$, $[R_FSO_3]^-$, $[HOSO_2(CF_2)_kSO_2O]^-$, $[OSO_2(CF_2)_kSO_2O]^{2-}$, $[Alkyl-SO_3]^-$, $[HOSO_2(CH_2)_kSO_2O]^-$, $[OSO_2(CH_2)_kSO_2O]^{2-}$, $[Alkyl-OSO_3]^-$, $[Alkyl-C(O)O]^-$, $[HO(O)C(CH_2)_kC(O)O]^-$, $[R_FC(O)O]^-$, $[HO(O)C(CF_2)_kC(O)O]^-$, $[O(O)C(CF_2)_kC(O)O]^{2-}$, $[(R_FSO_2)_2N]^-$, $[(FSO_2)_2N]^-$, $[((R_F)_2P(O))_2N]^-$, $[(R_FSO_2)_3C]^-$, $[(FSO_2)_3C]^-$, $PF_6^-$, $[PF_3(C_2F_5)_3]^-$, $[PF_3(CF_3)_3]^-$, $[B(COOCOO)_2^-$, $[(CF_3SO_2)_2N]^-$, $[(C_2F_5SO_2)_2N]^-$, $[(CF_3SO_2)(C_4F_9SO_2)N]^-$, $[(CN)_2N]^-$, $[CF_3SO_2]_3C]^-$, and $[(CN)_3C]^-$;

wherein k is an integer from 1 to 8; $R_F$ is a fluorinated aryl or alkyl-aryl or a fluorinated alkyl of formula $(C_oF_{2o-x+1}H_x)$, wherein o is an integer from 1 to 12 and x is an integer of from 0 to 7.

The alkyl-group mentioned above can be selected from linear or hyperbranched alkyl groups with 1 to 20 C-atoms, preferably with 1 to 14 C-atoms and particularly preferably with 1 to 4 C-atoms. Preferably $R_F$ means $CF_3$, $C_2F_5$, $C_3F_7$ or $C_4F_9$.

Particularly preferred ionic group is selected from $[(Alkyl)_2PO_2]^-$, $[(R_F)_4B]^-$, $[AlkylOSO_3]^-$, $[Alkyl-SO_3]^-$, $[R_FC(O)O]^-$, $[(R_F)BF_3]^-$, and $[(Alkyl-O)_2PO_2]^-$.

Examples for the suitable anionic groups are listed below:

Formula (274)

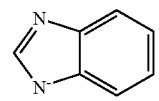

Formula (275)

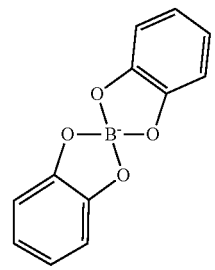

Formula (276)

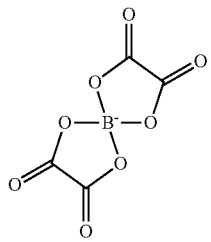

Formula (278)

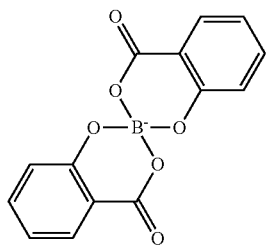

Formula (279)

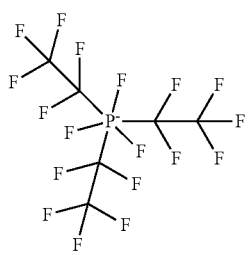

Formula (280)

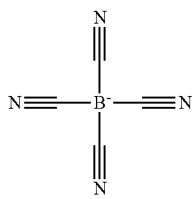

Formula (281)

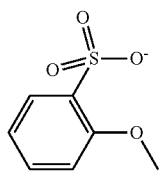

Formula (282)

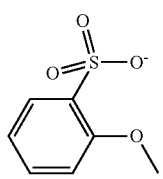

Formula (283)

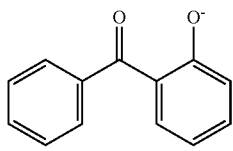

Formula (284)

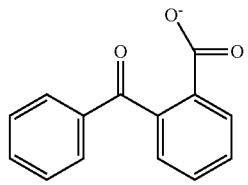

In case N is a cation it is preferably selected from the charged group consisting of alkali or alkali earth metal ions, such as $Li^+$, $Na^+$, $K^+$, $Cs^+$, $Mg^{2+}$, $Ca^{2+}$, $Sr^{2+}$, $Ba^{2+}$.

The present invention also relates to said compositions, characterized in that M is an anion and N is an anion which is selected from $K^+$, $Na^+$, $Li^+$, ammonium-, phosphonium-, thiouronium-, thioxonium-, guanidinium-cations, heterocylic cations and derivatives thereof.

In another preferred embodiment, N comprising one or more cationic groups selected from ammonium-, phosphonium-, thiouronium-, thioxonium-, guanidinium-cations, heterocylic cations and derivatives thereof, preferred examples of ammonium-, phosphonium-, thiouronium-, guanidinium cations and derivatives thereof are shown in formulae (285) to (289) and preferred examples of heterocylic cations are shown in formulae (290) to (317):

Formula (285)

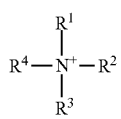

Formula (286)

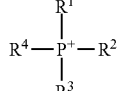

Formula (287)

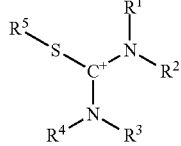

Formula (288)

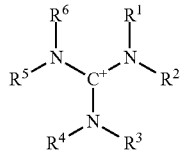

Formula (289)

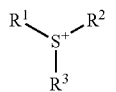

wherein $R^1$ to $R^6$ can be, independently from each other, selected from linear or hyperbranched alkyl rests with 1 to 20 C-atoms, linear or hyperbranched alkenyl rests with 2 to 20 C-atoms and one or more non-conjugated double bonds, linear or hyperbranched alkinyl rests with 2 to 20 C-atoms and one or more non-conjugated triple bond, saturated, partly saturated or completely saturated cycloalkyl with 3 to 7 C-atoms, which can further be substituted with alkyl groups having 1 to 6 C-atoms, wherein one or more substituents R may be partly or completely substituted with halogen, particularly with —F and/or —Cl, or partly substituted with —OR', —CN, —C(O)OH, —C(O)NR'$_2$, —SO$_2$NR'$_2$, —SO$_2$OH, —SO$_2$X, —NO$_2$, wherein one or two non adjacent and non α-carbon atoms of R$^1$ to R$^6$ can be substituted with groups selected from —O—, —S—, —S(O)—, —SO$_2$—, —N$^+$R'$_2$—, —C(O)NR'—, —SO$_2$NR'—, and —P(O)R'—, wherein R'=H, unsubstituted, partly or completely with —F substituted C1 to C6-alkyl, C3 to C7-cycloalkyl, unsubstituted or substituted phenyl and X=halogen.

In formula (285) R$^1$ to R$^4$ can be H, with the provision that at least one of the radicals R$^1$ to R$^4$ is not H. In formula (286) R$^1$ to R$^4$ can be H and NR'$_2$, wherein R' is defined as above. In formula (287) R$^1$ to R$^5$ can be H. In formula (288) R$^1$ to R$^6$ can be H, CN, and NR'$_2$, wherein R' is defined as above.

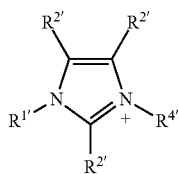

Formula (290)

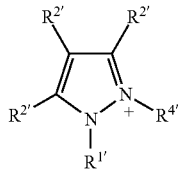

Formula (291)

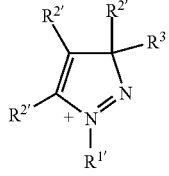

Formula (292)

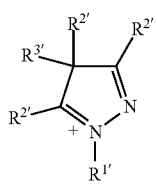

Formula (293)

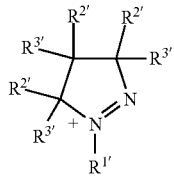

Formula (294)

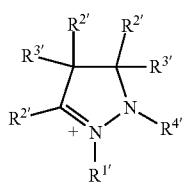

Formula (295)

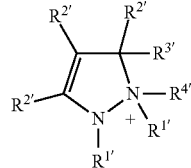

Formula (296)

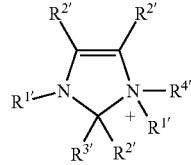

Formula (297)

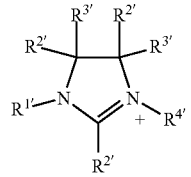

Formula (298)

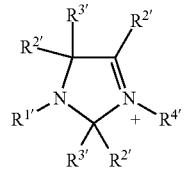

Formula (299)

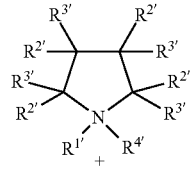

Formula (300)

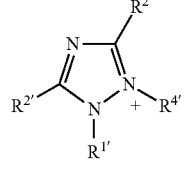

Formula (301)

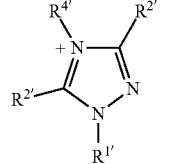

Formula (302)

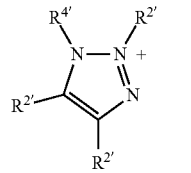

Formula (303)

-continued

Formula (304)
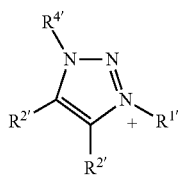

Formula (305)
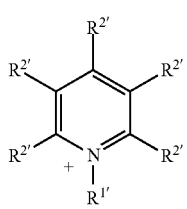

Formula (306)
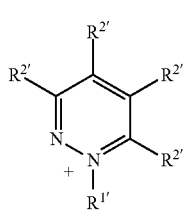

Formula (307)
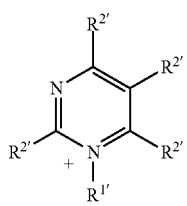

Formula (308)
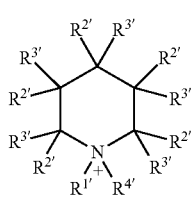

Formula (309)
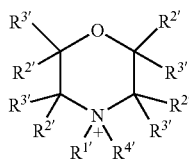

Formula (310)
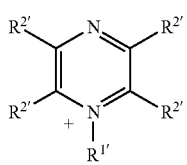

Formula (311)
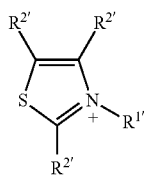

-continued

Formula (312)
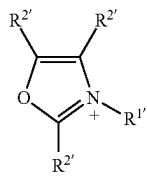

Formula (313)
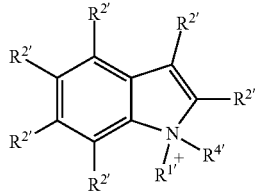

Formula (314)
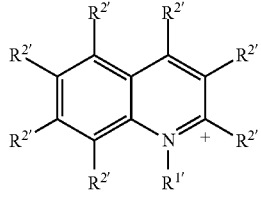

Formula (315)
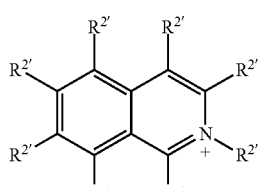

Formula (316)
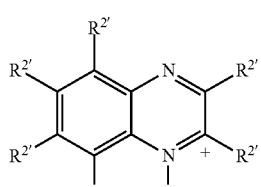

Formula (317)
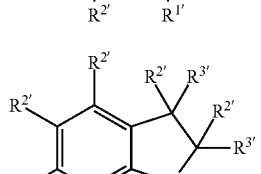

wherein the substituents $R^{1\prime}$ to $R^{4\prime}$ are independently from each other selected from H, CN, linear and branched alkyl rest with 1 to 20 C-atoms, linear or branched alkenyl radical with 2 to 20 C-atoms and one or more non conjugated double bonds, linear or branched alkinyl rest with 2 to 20 C-atoms and one or more non conjugated triple bonds, partly or completely non saturated cycloalkyl rest with 3 to 7 C-atoms which can be substituted with alkyl rests with 1 to 6 C-atoms, saturated and partly or completely non saturated heteroaryls, heteroaryl-$C_1$-$C_6$-alkyl, or alkyl-$C_1$-$C_6$-alkyl, wherein the substituents $R^{1\prime}$, $R^{2\prime}$, $R^{3\prime}$ and/or $R^{4\prime}$ together can form a ring, wherein one or more of the substituents $R^{1\prime}$ to $R^{4\prime}$ can partly or completely be substituted with halogen, particularly with —F and/or —Cl, and —OR', —CN, —C(O)OH, —C(O)NR'$_2$, —SO$_2$NR'$_2$, —C(O)X, —SO$_2$OH, —SO$_2$X, —NO$_2$, wherein the substituents $R^{1\prime}$ and R⁴' are not substituted with halogen at the same time, wherein one or two carbon atoms of the substituents R¹' and R²', which are non adjacent or bound to an heteroatom, can be substituted by a group selected from —O—, —S—, —S(O)—, —SO$_2$—, —N⁺R'$_2$—, —C(O)NR'—, —SO$_2$NR'—, and —P(O)R'— wherein R'=H, unsubstituted, partly or completely with —F substituted alkyl with 1 to 6 C-atoms, cycloalkyl with 3 to 7 C-atoms, unsubstituted or substituted phenyl and X=halogen.

Preference is given to R²' selected from —OR',—NR'$_2$, —C(O)OH, —C(O)NR'$_2$, —SO$_2$NR'$_2$)—SO$_2$OH, —SO$_2$X, and —NO$_2$.

Further preferred ions for N are disclosed in, e.g., US 2007/0262694 A1.

Further particularly preferred cations for the organic ion N have a structure represented by formula (318). They include N,N,N-trimethylbutyl ammonium ion, N-ethyl-N,N-dimethyl-propyl ammonium ion, N-ethyl-N,N-dimethylbutyl ammonium ion, N,N,-dimethyl-N-propylbutyl ammonium ion, N-(2-methoxyethyl)-N,N-dimethylethyl ammoniumion, 1-ethyl-3-methyl imidazolium ion, 1-ethyl-2,3-dimethyl imidazoliun ion, 1-ethyl-3,4-dimethyl imidazolium ion, 1-ethyl-2,3,4-trimethyl imidazolium ion, 1-ethyl-2,3,5-trimethyl imidazolium ion, N-methyl-N-propyl pyrrolidinium ion, N-butyl-N-methyl pyrrolidinium ion, N-sec-butyl-N-methylpyrrolidinium ion, N-(2-methoxyethyl)-N-methylpyrrolidinium ion, N-(2-ethoxyethyl)-N-methylpyrrolidinium ion, N-methyl-N-propyl piperidinium ion, N-butyl-N-methyl pipridinium ion, N-sec-butyl-N-methylpiperidinium ion, N-(2-methoxyethyl)-N-methyl piperidiniumion and N-(2-ethoxyethyl)-N-methyl piperidinium ion.

Formula (318)

Very particularly preferred is N-methyl-N-propyl piperidinium.

Further preferred cations N of the organic ionic compound according to the invention are selected from compounds comprising at least one of the general formulae (319) to (324):

Formula (319)

R⁴—N⁺—R²  
|  
R¹  
|  
R³

Formula (320)

R¹—S⁺—R³  
|  
R²

Formula (321)

R⁴—P⁺—R²  
|  
R¹  
|  
R³

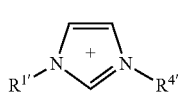

Formula (322)

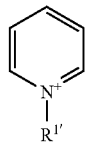

Formula (323)

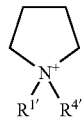

Formula (324)

wherein R¹ to R⁴ are defined as in formulae (285), (286), and (289), and R¹' and R⁴' as in formulae (290), (305), and (297).

Some examples of cationic groups suitable for the present invention are listed below:

Formula (325)

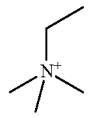

Formula (326)

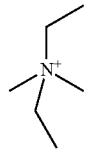

Formula (327)

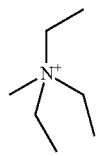

Formula (328)

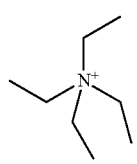

Formula (329)

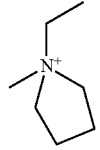

Formula (330)

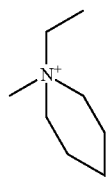

Formula (331)

Formula (332)
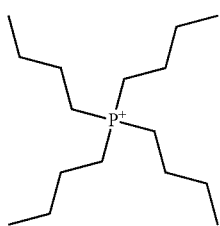

Formula (333)
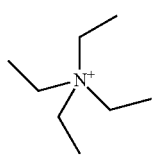

Formula (334)
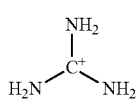

Formula (335)
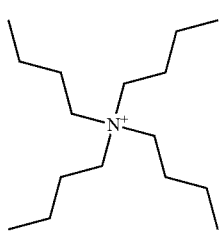

Formula (336)
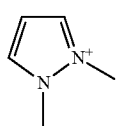

Formula (337)

Formula (338)
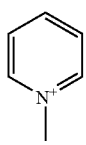

Formula (339)
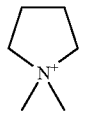

Formula (340)
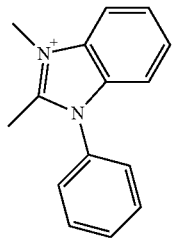

In one preferred embodiment, the N comprises further a non-functional organic group.

In another certain embodiment, the N of formula (1) comprises further a functional organic group, which can be preferably selected from groups comprising HTM, HIM, ETM, EIM, fluorescent emitter, phosphorescent emitter, host compound and dye, as described above and below.

Preference is given to a composition according to the present invention comprising a compound of formula (1), characterized in that either M or N is or comprises a functional organic group/material, preferably M with components as outlined above.

Further preference is give to a composition according to the present invention comprising a compound of formula (1), characterized in that both M and N are non-functional with components as outlined above.

Particular preference is given to compositions according to the present invention, characterized in that m in formula (1) is 2 or 3, y in formula (1) is 3 or 2 and n in formula (1) is 2 or 1.

The composition according to the present invention may also comprise at least one ion conductor compound. Preferably said composition comprises 3, particularly preferably 2, and very particularly preferably 1 ion conductor compound.

Suitable ion conductors are preferably selected from polymeric materials, such as perfluorosulfonic acid-based formulations, polybenzimidazoles, sulfonated polyetherketone, sulfonated naphthalenic polyimides, and polyethylene oxide (PEO)-based formulations. Further suitable polymers can be selected from the polymers for proton-exchange membrane for fuel cells. Such polymers are disclosed, for example, in the review by Hickner et al., "Alternative Polymer Systems for Proton Exchange Membranes (PEMs)" in Chemical Reviews, 2004, 104, 4587-4612. A very preferred ion conductor for the present invention is polyethylene oxide (PEO). The concentration of the ion conductor in the composition can be from 1 to 40 wt %, preferably from 2 to 30 wt %, particularly preferably from 5 to 25 wt %, and very particularly preferably from 8 to 20 wt %.

Furthermore, said composition may also comprise at least one dye, preferably 3, particularly preferably 2, and very particularly preferably 1 dye.

Dyes are of particular importance, if said compositions are used in photovoltaic devices. Suitable dyes can be selected from any dye know to the skilled person in the field of organic solar cells and/or dye-sensitized solar cells.

Suitable dyes can be metal complex dyes selected from polypyridyl complexes of transition metals, preferably ruthenium, osmium and copper. In a preferred embodiment, the metal complex dye has the general structure $ML_2(X)_2$, where L is preferably selected from 2,2'-bipyridyl-4,4'-dicarboxylic acid, M is a transition metal preferably selected from Ru, Os, Fe, V and Cu, and X selected from groups comprising a halide, cyanide, thiocyanate, acetyl acetonate, thiacarbamate or water substituent. Such metal-complex dyes are disclosed for example in the Journal of Physical Chemistry C 2009, 113, 2966-2973, US 2009/000658, WO 2009/107100, WO 2009/098643, U.S. Pat. No. 6,245,988, WO 2010/055471, JP 2010084003, EP 1622178, WO 98/50393, WO 95/29924, WO 94/04497, WO 92/14741 and WO 91/16719. The disclosures of each of the foregoing listed patent documents are hereby incorporated herein by reference in their entireties.

Further suitable dyes are selected from organic compounds containing fused ring system, for example anthracene, pentacene and tetracence derivatives, AZO, phthalocaynine, including metal-free phthalocaynines, donor or accepotor doped metal-free phthalocaynines and metal phthalocyanines, porphyrins, squaraine, perylene-diimide, perylene pigments as summarized as charge generation materials (CGM) by Paul M. Borsenberger; David S. Weiss Organic Photorecptors for Xerography; Marcel Dekker, Inc., 1998, Chapter 6, and K. Y. Law, Chem. Rev. Vol 93, 449-486 (1993), and a polymeric materials comprising one or more dyes.

In a very preferred embodiment, the dye is a perylene derivate, in small molecular form or in polymer form as disclosed for example in Angew. Chem. Int. Ed. 2006, 45, 3364-3368.

For photovoltaic application it is preferred to have a composition comprising ionic compounds of formula (1) and a further dye as described above. the concentration of the dye in the composition can be from 1 to 50 wt %, preferably from 5 to 40 wt %, and particularly preferably from 10 to 30 wt %, and very particularly preferably from 15 to 30 wt %.

The present invention further relates to a non-polymeric functional ionic organic compound selected from host materials, phosphorescent emitters, fluorescent emitters, hole transporting materials (HTM), hole injecting materials (HIM), electron transporting materials (ETM), and electron injecting materials (EIM) having the following formula (1):

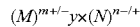

$(M)^{m+/-}{}_y \times (N)^{n-/+}$   Formula (1);

wherein N, m, y and n are defined as above in formula (1) in conjunction with said compositions and wherein M is defined as above in formula (1) in conjunction with said compositions and wherein the molecular weight of the compound of formula (1) is below 1000 g/mol, preferably below 800 g/mol, particularly preferably below 600 g/mol and very particularly preferably below 500 g/mol; and wherein the net charge of the compound of Formula (1) is zero.

Preferably said compound does not consist of or comprise an organic transition metal complex.

Particularly preferably said compound does not consist of or comprise an organic metal complex.

The remaining structural and molecular component of the compound of formula (1) are the same as outlined above for the compound of formula (1) in the compositions according to the present invention.

Formulation, preferably a solution, dispersion or mini-emulsion, comprising the said composition or said compound of formula (1) and at least one solvent is also subject of the present invention.

Examples of suitable and preferred organic solvents include, without limitation, dichloromethane, trichloromethane, chloroform, mono-chlorobenzene, o-dichlorobenzene, tetrahydrofuran, anisole, morpholine, toluene, o-xylene, m-xylene, p-xylene, 1,4-dioxane, acetone, methyl-ethylketone, 1,2-dichloroethane, 1,1,1-trichloroethane, 1,1,2,2-tetra-chloroethane, ethyl acetate, n-butyl acetate, dimethylformamide, dimethyl-acetamide, dimethylsulfoxide, tetralin, decalin, indane and/or mixtures thereof.

The formulation or solution of the present invention preferably comprises 0.1 to 10 wt % of the composition or the organic ionic compound according to the invention, particularly preferably 0.5 to 5 wt %, based on the content of the whole solution. Optionally, the solution may also comprises one or more binders to adjust the rheological properties, as described in WO 2005/055248 A1.

After the appropriate mixing and ageing, formulations or solutions according to the invention are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., Journal of Paint Technology, 38, No 496, 296 (1966)". Solvent blends may also be used and can be identified as described in "Solvents, W. H. Ellis, Federation of Societies for Coatings Technology, 9-10, 1986". Such a procedure may lead to a blend of 'non' solvents that will dissolve the composition, although it is desirable to have at least one true solvent in a blend.

Another preferred form of a formulation according to the present invention is an emulsion, and very preferably a mini-emulsion, which are specially formulated heterophase systems in which stable nanodroplets of one phase are dispersed in a second, continuous phase. The present invention preferably relates to a mini-emulsion, wherein the different components of the composition are located either in the same phase or in different phases. A preferred distribution is that the majority or all of organic functional compounds (ETM, EIM, HTM HIM, fluorescent and phosphorescent emitter compound, dye) are in nanodroplets (discontinuous phase), and the majority or all of organic ionic compounds are in the continuous phase. The preferred form of the formulation of the present invention is a mini-emulsion. To increase the kinetic stability of the emulsion, surfactant(s) could be added. The selection of solvents for two phase and surfactants, and the processing to make a stable mini-emulsion is well known to one skilled in the art, or are referred to various publications, for example, Landfester et al. (Annu. Rev. Mater. Res. 2006, 36, 231).

The device according to the present invention is produced in that the active layer is formed by depositing the mixture or a solution/formulation of it of the present invention by any suitable method. Liquid coating of devices such as light emitting device is more desirable than vacuum deposition techniques. Solution deposition methods are particularly preferred. Preferred deposition techniques include, without limitation, dip coating, spin coating, ink jet printing, letterpress printing, screen printing, doctor blade coating, roller printing, reverse-roller printing, offset lithography printing, flexographic printing, web printing, spray coating, brush coating or pad printing, slot-die coating. Ink-jet printing is particularly preferred as it allows high resolution displays to be prepared.

Selected solutions of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the composition of the present invention should be first dissolved in a suitable solvent. Solvents must fulfill the requirements stated above and must not have any detrimental effect on the chosen print head. Additionally, solvents should have boiling points >100° C., preferably >140° C. and more preferably >150° C. in order to prevent operability problems caused by the solution drying out inside the print head. Apart from the solvents mentioned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing compositions of the present invention by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the polymer, which reduces or prevents clogging of the jets and separation of the components during spraying. The solvent(s) may include those selected from the following list of examples: dodecylbenzene, 1-methyl-4-tert-butylbenzene, terpineol limonene, isodurene, terpinolene, cymene, diethylbenzene. The solvent may be a solvent mixture, that is a combination of two or more solvents, each solvent preferably having a boiling point >100° C., more preferably >140° C. Such solvent(s) also enhance film formation in the layer deposited and reduce defects in the layer.

The ink jet fluid (that is mixture of solvent, binder and the composition) preferably has a viscosity at 20° C. of 1 to 100 mPa·s, particularly preferably 1 to 50 mPa·s and very particularly preferably 1 to 30 mPa·s.

The composition or a solution/formulation of them according to the present invention can additionally comprise one or more further components like for example surface-active compounds, lubricating agents, wetting agents, dispersing agents, hydrophobing agents, adhesive agents, flow improvers, de-foaming agents, deaerators, diluents which may be reactive or non-reactive, auxiliaries, colorants, dyes or pigments, sensitizers, stabilizers, or inhibitors.

The compositions and compounds according to the present invention can be used in electronic devices. Thus, the present invention also relates to an electronic device comprising at least one composition according to the present invention or at least one compound according to the present invention.

Further, the present invention relates to said device, characterized in that the device is an organic electroluminescent device, or an organic sensor, or an organic solar cell.

Preferably, said device comprises at least two electrodes. The electronic devices can generally spoken individually tailored in any form that is required for their use.

A typical sequence of layers comprised in the electronic device of the invention are for example:
optionally a first substrate,
a first electrode layer (anode),
optionally a hole injection layer (HIL),
optionally a hole transport layer (HTL) and/or an electron blocking layer (EBL),
an active layer, which upon electrical or optical exciation, produces excitons,
optionally an electron transport layer (ETL) and/or a hole blocking layer (HBL),
optionally an electron injection layer (EIL),
a second electrode layer (cathode),
optionally a second substrate.

The electronic device comprises at least in one layer composition according to the present invention or a compound according to the present invention as described above. The sequence of the given layer structure is exemplary. Other sequences are possible. Depending on the active layers in the above mentioned device, different opto-electronic devices can be obtained. In a first preferred embodiment, the active layer generates excitons upon electronic excitation through applying voltage between anode and cathode, and further emits light on radiative decay of the excitons. In general, this is called electroluminescent device, for example OLED, PLED or OLEC. In another preferred embodiment, the active layer generates exciton through absorbing light, and further produces free charge carrier through exciton dissociation. In general, this is called photovoltaic or solar cell.

In another preferred embodiment of the present invention the device according to the invention comprises one or more further organic compounds selected from the group consisting of a matrix compound, a fluorescent or phosphorescent emitter compound, a dye compound, a hole injection compound, a hole transport compound, an electron injection compound and an electron transporting compound, wherein these compounds can be taken from the list defined above.

Preferably, the ionic compound in the composition or the compound according to formula (1) have a different function than that of the additional organic functional material. It is, however, conceivable that both have the same function.

In a certain embodiment, the said electronic device comprises an EIL and/or ETL comprising an organic ionic compound of formula (1) and a further non-ionic EIM and/or ETM, wherein the organic ionic compound has a concentration from 1 to 99 wt %, preferably from 10 to 90 wt %, particularly preferably from 20 to 80 wt %, and very particularly preferably from 30 to 70 wt %. The said further non-ionic EIM and/or ETM can be selected from the EIM and/or EIM as described above.

In another certain embodiment, the said electronic device comprises an HIL and/or HTL comprising an organic ionic compound of formula (1) and a further non-ionic HIM and/or HTM, wherein the ionic compound has a concentration from 1 to 99 wt %, preferably from 10 to 90 wt %, and very preferably from 20 to 80 wt %, and particularly preferably from 30 to 70 wt %. The said further non-ionic EIM and/or ETM can be selected from the EIM and/or EIM as described above In a preferred embodiment, the said electronic device is an electroluminescent device, comprising 1) an EIL, comprising at least one composition or compound of formula (1), wherein the M comprising an electron injection group; and/or 2) an ETL, comprising at least one composition or compound of formula (1), wherein the M comprising an electron transport group; and/or 3) an HTL, comprising at least one composition or compound of formula (1), wherein the M comprising a hole transport group; and/or 4) an HIL, comprising at least one composition or compound of formula (1), wherein the M comprising a hole injection group;

It is also preferred that the layer comprising the composition or organic ionic compound of formula (1) further comprises a ion conductive material. It may help to improve the ion mobility, thus reduce and operation voltage, and improve the response time, efficiency and/or lifetime.

In a very preferred embodiment, the electronic device is an electroluminescent device (OLED or PLED), characterized in that in the active layer consists of non-ionic organic compound(s). The possible device structures of OLEDs or PLEDs, and the preparation of these devices can be referred to the numerous references, for example WO 2004/037887, WO 2004/084260 A2 etc.

In a particularly preferred embodiment, the electronic device is an electroluminescent electrochemical cell (generally called hereafter OLEC), characterized in that in the active layer comprises at least one composition or ionic organic compound of formula (1). In a preferred embodiment, the ionic organic compound is an fluorescent emitter, preferably comprising in M one fluorescent group. It is desired in this embodiment, that the active layer comprises at least further one non-ionic organic materials, preferably selected from the singlet host or matrix materials as described above.

In another preferred embodiment, the ionic organic compound works as host or matrix in the emissive layer of the said OLEC, preferably comprising in M one host or matrix group. It is preferred in this embodiment to comprise a further organic compound in the emissive layer preferably selected from emitter materials. In one preferred embodiment, the emitter is a fluorescent emitter, which can be preferably selected from the singlet emitter materials described above. The concentration of the said singlet emitter can be from 1 wt % to 20 wt %, preferably from 2 to 15 wt %, and particularly preferably from 3 to 10 wt %, and very particularly preferably from 3 to 8 wt %. In another more preferred embodiment, the emitter is a phosphorescent emitter. The concentration of the said phosphorescent emitter can be from 1 to 30 wt %, preferably from 2 to 25 wt %, and particularly preferably from 5 to 20 wt %, and very particularly preferably from 10 to 20 wt %. Suitable and preferred phosphorescent emitters are the ones discussed in the present invention.

Sometime, it is advantageous to use 2 or more host materials in the same emissive layer in the said electronic device, to tune the charge balance, and therefore to improve the efficiency and for lifetime. Preferably in the said OLEC, the ionic compound is used as co-host with at least further one host material, with a concentration from 1 to 99 wt %, preferably from 10 to 90 wt %, and particularly preferably from 20 to 80 wt %, and very particularly preferably from 30 to 70 wt %.

In a simple form, the said OLEC has a device structure of anode/EML/cathode. Preferably, the OLEC further comprises a HIL, also called as buffer layer. Also preferably, the OLEO further comprises an interlayer between HIL and EML. The Interlayer has a function of hole transport and electron blocking functions. The example for interlayer materials and device structure can be referred to WO 2004/084260 A2.

The two electrodes of the device are preferably a cathode and an anode. Both electrodes are preferably connected through the above mentioned organic active layer.

In comparison to OLED or PLED, OLEC don't need a reactive metal as cathode. Therefore, in principle all conductive materials, both organic and inorganic, including conductive polymers, metal, metal oxide and mixture thereof can be as anode and cathode in OLEC. The anode and cathode of the OLEC can be of the same or different materials.

Preferred materials for the electrodes used in OLECs are selected from metals, particularly preferably selected from Al, Cu, Au, Ag, Mg, Fe, Co, Ni, Mn, Zn, Cr, V, Pd, Pt, Ga, In and their alloys, conductive oxide, for example ITO, AZO, ZnO, and conductive organic thin films comprising such as poly(ethylenedioxythiophene)-polystyrene sulfonate (PEDOT:PSSH), Polyaniline (PANI). Further suitable conducting polymers could be found for example in the reviews edited by Michael S. Freund & Bhavana Deore, in "Self-Doped Conducting Polymers", John Willey & Sons, Ltd., 2007.

Preferably, the devices according to the invention, preferably OLECs, are prepared on a flexible substrate. The suitable substrate is preferably selected from films or foils based on polymers or plastics. The main selection criteria for polymers or plastics are 1) hygienic property and 2) glass transition temperature. The glass temperature ($T_g$) of the polymers can be found in a common handbooks, e.g. in "Polymer Handbook", Eds. J. Brandrup, E. H. Immergut, and E. A. Grulke, John Willey & Sons, Inc., 1999, VI/193-VI/276. Preferably, the $T_g$ of the polymer is above 100° C., very preferably above 150° C., and particularly preferably above 180° C., and most preferably above 200° C. Very preferred substrates are for example, poly(ethylene terephthalate) (PET) and poly(ethylene 2,6-naphthalate) (PEN).

To avoid degradations caused by oxygen and moisture, and also to prevent active materials in the devices, an appropriate encapsulation for the said device is a prerequisite.

There are many technologies suitable for encapsulation of the devices according to the present invent. In general, all encapsulation techniques, which are developed for organic light emitting diodes (OLEDs), organic solar cells, organic dye-sensitized solar cells, organic field-effect transistor (OFETs), thin film batteries, microelectromechanical systems (MEMS) and electronic papers, can be applied in order to encapsulate the devices according to the present invention.

In a preferred embodiment, the device of the present invention is encapsulated using a thin film encapsulation. Typically, a thin film encapsulation consists of alternating multilayers of an inorganic/organic stack, wherein inorganic layers are used to achieve adequate barrier performance and organic layers to eliminate inevitable defects of the inorganic layers. The materials used for inorganic layers can be selected from metals, metal oxides or mixed oxides, for example Ag, $SiO_x$, $SiN_x$, $AlO_x$, $ZrO_x$, $ZnO_x$, $HfO_x$, $TiO_x$ and indium tin oxide and so on. Some examples are alternating multilayers of vacuum-deposited acrylate polymers/$AlO_x$ as reported by Graff, G. L. et al. (J. Appl. Phys. 2004, 96, 1840), $Al_2O_3$/polyurea layers as reported by Young Gu Lee et al. (Org. Electron. 2009, 10, 1352 and in Dig. Tech. Pap.-Soc. Inf. Disp. Int. Symp. 2008, 39, 2011), $SiON/SiO_2$/parylene on PET substrate as reported by Han, Jin Woo, et al. (Jpn. J. Appl. Phys., Part 1 2006, 45, 9203), and polyacrylate (20 µm)-Ag (200 nm) as reported by Wang, Li Duo et al. (Chin. Phys. Lett. 2005, 22, 2684).

By using advanced deposition techniques, for example atomic layer deposition (ALD), plasma assisted pulsed laser deposition (PAPLD) and plasma enhanced chemical vapor deposition (PECVD), the defects in inorganic layer can be significantly reduced so that all inorganic layers can be used, for example $Al_2O_3/HfO_2$ nanolaminated films by ALD as reported by Chang, Chih Yu et al. (Org. Electron. 2009, 10, 1300), and SiNx/SiOx layers as reported by Li, C. Y. et al. (IEEE Electron. Compon. Technol. Conf. 2008, 58th, 1819), (PECVD SiO)/poly-benzo-oxazole (PBO) by Shimooka, Y. et al. (IEEE Electron. Compon. Technol. Conf. 2008, 58th, 824), nanolaminated alternating layers of $Al_2O_3/ZrO_2$ by Meyer, J. et al. (Appl. Phys. Lett. 2009, 94, 233305/1), and nanolaminates of $Al_2O_3/ZrO_2$ by PAPLD as reported by Gorrn, Patrick et al. (J. Phys. Chem. 2009, 113, 11126), and SiC layers by PECVD as reported by Weidner, W. K. et al. (Annu. Tech. Conf. Proc—Soc. Vac. Coaters 2005, 48th, 158), multilayer stack of silicon nitride-silicon oxide-silicon nitride silicon oxide-silicon nitride (NONON) by PECVD as reported by Lifka, H., et al. (Dig. Tech. Pap.—Soc. Inf. Disp. Int. Symp. 2004, 35, 1384), and polyethersulfon (PES)/ALD $AlO_x$ as reported by Park, Sang-Hee Ko, et al. (ETRI Journal 2005, 545). A review on thin film encapsulation by CVD and ALD is provided by Stoldt, Conrad R, et al. (J. Phys. D: Appl. Phys. 2006, 39, 163).

Further single layer encapsulation was also developed. Examples of single barrier layers are a perfluorinated polymer (Cytop), which can be easily spin-coated on OLEDs, as reported by Granstrom, J. et al. (Appl. Phys. Lett. 2008, 93, 193304/1), and single layer consisting of aluminum oxynitride ($AlO_xN_y$) by using a reactive radio frequency (RF) magnetron sputtering as reported by Huang, L. T. et al. (Thin Solif Films 2009, 517, 4207), single poly-SiGe layer by PECVD as reported by Rusu, Cristina et al. (J. Microelectromech. Syst. 2003, 12, 816).

Further details on materials and methods for encapsulation are disclosed, e.g., in WO 2009/089417, WO 2009/089417, WO 2009/042154, WO 2009/042052, US 2009/081356, US 2009/079328, WO 2008/140313, WO 2008/012460, EP 1868256, KR 2006/084743, KR 2005/023685, US 2005/179379, US 2005/023974, KR 2003/089749, US 2004/170927, US 2004/024105, WO 2003/070625, and WO 2001/082390.

In another preferred embodiment, the device of the present invention is encapsulated by using a curable resin together with a cap, wherein the cap covers at least the light emitting area, and the curable resin is applied between the substrate and the cap. The cap materials can be selected from metals and plastics in form of a plate or foil, and glass cap. Preferably, the cap is flexible, which is preferably selected from metal foils, plastic foils or metallised plastic foils. The metal can be selected from Al, Cu, Fe, Ag, Au Ni, whereby Al is particularly preferred. The selection criteria for plastics are 1) hygienic aspects 2) the glass transition temperature ($T_g$), which is supposed to be high enough. $T_g$ of polymers can be found in a suitable handbook, for example in "Polymer Handbook", Eds. J. Brandrup, E. H. Immergut, and E. A. Grulke, John Willey & Sons, Inc., 1999, VI/193-VI/276. Preferably, the polymer suitable for cap material has a $T_g$ above 60° C., preferably above 70° C., particularly preferably above 100° C., and very particularly preferably above 120° C. The cap used in the present invention is poly (ethylene 2,6-naphthalate) (PEN).

The suitable resin can be thermally cured or UV-curable. Preferably, the resin is UV-curable, optionally supported or facilitated by heating. A typical resin is the epoxy-based resin, which is commercially available at for example Nagase & Co., LTD. and DELO Industrie Klebstoffe. The resin can be applied on full-area of the emitting area or just on the edge, where no light emitting area is underneath.

Devices can generally spoken individually tailored in any form that is required for their use.

In a further preferred embodiment the device of the present invention has an extent between 0.5 cm² and 100000 cm², particularly preferably between 0.5 cm² and 50000 cm².

The device according to claim 14 or 15, characterized in that the device is selected from organic light emitting diodes (OLED), polymer light emitting diodes (PLED), organic light emitting transistors (OLET), organic light emitting electrochemical cells (OLEC), organic light emitting electrochemical transistors (OLEETs), organic field effect transistors (OFET), thin film transistors (TFT), organic solar cells (O-SC), organic laser diodes (G-laser), organic integrated circuits (O-IC), radio frequency identification (RFID) tags, photodetector, sensors, logic circuits, memory elements, capacitor, charge injection layers, Schottky diodes, planarising layers, antistatic films, conducting substrates or patterns, photoconductors, electrophotographic elements, organic solar concentrator, organic spintronic devices, and an organic plasmon emitting devices (OPEDs), preferably the device is an OLED, OLEC or an O-SC, particularly preferably an OLEC or O-SC.

The device structure of the above mentioned electronic device should be clear for the expert in the field. Nevertheless, the inventors would like to give some reference on some detailed device structures for clarity.

Organic Plasmon emitting device is preferably referred to the device as reported by Koller et al., in Nature Photonics (08), 2, pp 684-687. The OPED is very similar as OLED as described above, except that at least one of anode and cathode should be capable to couple surface Plasmon from the emissive layer. It is preferred that an OPED comprises one Compound as described above and below.

Organic light emitting transistor (OLET) has a very similar structure of organic field effect transistor, but with a bipolar material as active layer between the source and the drain. The most recent development on OLET can be referred to the paper by Muccini et al., in Nature Materials 9, 496-503 (2010). It is preferred that an OLET comprises one Compound as described above and below.

Organic light emitting electrochemical transistors (OLEETs), as reported by Sariciftci et al., in Appl. Phys. Lett. 97, 033302 (2010), has a very similar structure of organic field effect transistor, but with a mixture of an emissive polymer and a ionic compound as active layer between the source and the drain.

Electrophtotographic element comprises a substrate, an electrode, and a charge transport layer above the electrode, optionally a charge generation layer between electrode and the charge transport layer. For device details and variations and the materials use therein please refer to the book "Organic Photoreceptors for Xerography" Marcell Dekker, Inc., Ed. by Paul M. Borsenberger & D. S. Weiss (1998). It is preferred that such device comprises one Compound as described above and below, especially in charge transport layer.

One preferred organic spintronic device is a spin-valve device, as reported by Z. H. Xiong et al., in Nature 2004 Vol 427 pp 821, comprising two ferromagnetic electrodes and an organic layer between the two ferromagnetic electrodes, wherein at least one of the organic layers comprising a compound according the present invention and the ferromagnetic electrode is composed of Co, Ni, Fe, or alloys thereof, or $ReMnO_3$ or $CrO_2$, wherein Re is rare earth element.

organic light emitting electrochemical cells (OLECs) comprises two electrodes, and a mixture or blends of electrolyte and fluorescent species in between, as firstly reported by Pei & Heeger in Science (1995), 269, pp 1086-1088. It is desired that one Compound as described above and below could be used in such device.

Dye-sensitized solar cells (DSSCs) comprises, in the sequence, an electrode/dye-sensitized $TiO_2$ porous thim film/electrolyte/counter electrode, as firstly reported by O'Regan & Grätzel in Nature (1991), 353, pp 737-740. The liquid electrolyte can be replaced by a solid hoel transport layer, as reported in Nature (98), 395, pp 583-585.

Organic solar concentrator (OSC) could be referred to the report by Baldo et al., in Science 321, 226 (2008). An OSC consist of a thin film of organic dyes deposited on high-refractive-index glass substrates. The dyes absorb incident solar radiation and reemit it at a lower energy. The majority of the reemitted photons are trapped within the waveguide by total internal reflection for ultimate collection by a photovoltaic device mounted on the substrate edges The device according to the present invention may have any form or shape suitable for a specific application, preferably the device architecture is flat or has the form of a fiber.

Flexible fiber electroluminescent light sources are known in the art, as set forth, for example in U.S. Pat. No. 6,074,071, U.S. Pat. No. 5,485,355 and U.S. Pat. No. 5,876,863. Chemiluminescent fiber light sources are also known. These devices emit light when they are twisted to combine two chemicals contained in the fiber. The chemical reaction between the chemicals produces light while the chemical reaction proceeds for a few hours. However, these prior art chemiluminescent fiber light sources lack sufficient brightness, and are unable to achieve sufficient requirements for the medical or cosmetic use.

OLED fibers have been described recently in U.S. Pat. No. 6,538,375 B1, US 2003/0099858, and by Brenndan O'Connor et al. (Adv. Mater. 2007, 19, 3897-3900). Single OLED fibers and their use in lightening is described. Further details on OLED and/or OLEC fiber are disclosed in PCT/EP2011/000707 and PCT/EP2011/000705, respectively. The disclosures of each of the foregoing listed patents and otherwise published documents are hereby incorporated herein by reference in their entireties.

The compounds, compositions, devices, and formulations according to the present invention can be used for the treatment and/or prophylaxis and/or diagnosis of medical diseases and/or in the field of cosmetic/aesthetic applications. This treatment, prophylaxis and/or diagnosis can be accomplished by the use of a phototherapeutic device comprising the compounds, compositions and/or formulations according to the present invention.

Thus, the present invention further relates to the use of the compounds and/or compositions and/or formulations according to the invention and devices comprising the compounds and/or compositions and/or formulations for the treatment, prophylaxis and/or diagnosis of diseases. The present invention still furthermore relates to the use of the compounds and/or compositions and/or formulations according to the invention and devices comprising them for the treatment and prophylaxis of cosmetic conditions.

Particularly, the present invention relates to said composition or said compound or said formulation for the use in phototherapy of medical diseases and/or cosmetic conditions.

The present invention furthermore relates to the use of the compounds and/or compositions and/or formulations according to the invention for the production of devices for the therapy, prophylaxis and/or diagnosis of therapeutic diseases.

Phototherapy or light therapy is used in many medical and/or cosmetic areas. The compounds and/or compositions and/or formulations according to the invention and the devices comprising them can therefore be employed for the therapy and/or prophylaxis and/or diagnosis of all diseases and/or in cosmetic applications for which the person skilled in the art considers the use of phototherapy. Besides irradiation, the term phototherapy also includes photodynamic therapy (PDT) and disinfection and sterilisation and conservation (e.g. conservation of foodstuffs and/or beverages and soft drinks) in general. Phototherapy or light therapy can be used for the treatment of not only humans or animals, but also any other type of living or non-living materials. These include, for example, fungi, bacteria, microbes, viruses, eukaryotes, prokaryonts, foods, drinks, water and drinking water.

The term phototherapy also includes any type of combination of light therapy and other types of therapy, such as, for example, treatment with active compounds. Many light therapies have the aim of irradiating or treating exterior parts of an object, such as the skin of humans and animals, wounds, mucous membranes, the eye, hair, nails, the nail bed, gums and the tongue. The treatment or irradiation according to the invention can in addition also be carried out inside an object in order, for example, to treat internal organs (heart, lung, etc.) or blood vessels or the breast.

The therapeutic and/or cosmetic areas of application according to the invention are preferably selected from the group of skin diseases and skin-associated diseases or changes or conditions, such as, for example, psoriasis, skin ageing, skin wrinkling, skin rejuvenation, enlarged skin pores, cellulite, oily/greasy skin, folliculitis, actinic keratosis, precancerous actinic keratosis, skin lesions, sun-damaged and sun-stressed skin, crows' feet, skin ulcers, acne, acne rosacea, scars caused by acne, acne bacteria, photomodulation of greasy/oily sebaceous glands and their surrounding tissue, jaundice, jaundice of the newborn, vitiligo, skin cancer, skin tumours, Crigler-Najjar, dermatitis, atopic dermatitis, diabetic skin ulcers and desensitisation of the skin.

Particular preference is given for the purposes of the invention to the treatment and/or prophylaxis of psoriasis, acne, cellulite, skin wrinkling, skin ageing, jaundice and vitiligo.

Further areas of application according to the invention for the compounds, compositions, formulations, and/or devices comprising them according to the invention are selected from the group of inflammatory diseases, rheumatoid arthritis, pain therapy, treatment of wounds, neurological diseases and conditions, oedema, Paget's disease, primary and metastasising tumours, connective-tissue diseases or changes, changes in the collagen, fibroblasts and cell level originating from fibroblasts in tissues of mammals, irradiation of the retina, neovascular and hypertrophic diseases, allergic reactions, irradiation of the respiratory tract, sweating, ocular neovascular diseases, viral infections, particularly infections caused by herpes simplex or HPV (human papillomaviruses) for the treatment of warts and genital warts.

Particular preference is given for the purposes of the invention to the treatment and/or prophylaxis of rheumatoid arthritis, viral infections and pain.

Further areas of application according to the invention for the compounds and/or devices comprising the compounds according to the invention are selected from winter depression, sleeping sickness, irradiation for improving the mood, the reduction in pain, particularly muscular pain caused by, for example, tension or joint pain, elimination of the stiffness of joints and the whitening of the teeth (bleaching).

Further areas of application according to the invention for the compounds, compositions, formulations, and/or devices comprising them according to the invention are selected from the group of disinfections. The compounds according to the invention and/or the devices according to the invention can be used for the treatment of any type of objects (non-living materials) or subjects (living materials such as, for example, humans and animals) for the purposes of disinfection. This includes, for example, the disinfection of wounds, the reduction in bacteria, the disinfection of surgical instruments or other articles, the disinfection of foods, of liquids, in particular water, drinking water and other drinks, the disinfection of mucous membranes and gums and teeth.

Disinfection here is taken to mean the reduction in the living microbiological causative agents of undesired effects, such as bacteria and germs.

For the purposes of the phototherapy mentioned above, devices comprising the devices according to the invention preferably emit light having a wavelength between 250 and 1250 nm, particularly preferably between 300 and 1000 nm and especially preferably between 400 and 850 nm.

In a particularly preferred embodiment of the present invention, the device for the use in phototherapy is an organic light-emitting diode (OLED) or an organic light-emitting electrochemical cell (OLEC). Both the OLED and the OLEC can have a planar or fibre-like structure having any desired cross section (for example round, oval, polygonal, square) with a single- or multilayered structure. These OLECs and/or OLEDs can be installed in other devices which comprise further mechanical, adhesive and/or electronic elements (for example battery and/or control unit for adjustment of the irradiation times, intensities and wavelengths). These devices comprising the OLECs and/or OLEDs according to the invention are preferably selected from the group comprising plasters, pads, tapes, bandages, cuffs, blankets, caps, sleeping bags, textiles and stents.

The use of the said devices for the said therapeutic and/or cosmetic purpose is particularly advantageous compared with the prior art, since homogeneous irradiation of lower irradiation intensity is possible at virtually any site and at any time of day with the aid of the devices according to the invention using the OLEDs and/or OLECs. The irradiation can be carried out as an inpatient, as an outpatient and/or by the patient themselves, i.e. without initiation by medical or cosmetic specialists. Thus, for example, plasters can be worn under clothing, so that irradiation is also possible during working hours, in leisure time or during sleep. Complex inpatient/outpatient treatments can in many cases be avoided or their frequency reduced. The devices according to the invention may be intended for re-use or be disposable articles, which can be disposed of after use once, twice or three times.

Further advantages over the prior art are, for example, lower evolution of heat and emotional aspects. Thus, newborn being treated owing to jaundice typically have to be irradiated blindfolded in an incubator without physical contact with the parents, which represents an emotional stress situation for parents and newborn. With the aid of a blanket according to the invention comprising the OLEDs and/or OLECs according to the invention, the emotional stress can be reduced significantly. In addition, better temperature control of the child is possible due to reduced heat production of the devices according to the invention compared with conventional irradiation equipment.

The present invention further relates to a method of treatment medical diseases and/or cosmetic conditions by employing the compounds and/or compositions and/or formulations and/or devices comprising the compounds, compositions or formulations according to the present invention. The specific indications to be treated are the same as outlined above.

Finally the present invention relates to the preparation of said compounds, compositions and formulations.

In the following, some non-limiting examples are given to the general synthesis route for the organic ionic compounds according to the present invention. In the scheme 1 to 6, $Li^+$ is taken as counter ion in the ionic compounds, and in the scheme 7 to 8, $BF_4^-$ and $PF_6^-$ as counter ion. Those are just examples. The one skilled in the art should be readily aware that any other cation or anion may be used instead of $Li^+$ or $BF_4^-$ or $PF_6^-$, where available and applicable. The Ar in the scheme 1 to 8 is an aromatic or heteroaromic system, having the same means of $Ar_4$ in formula (45), which can be preferably selected from the groups of fluorescent emitter, HIM, HTM, Host, ETM and EIM, as described above, and R has the same means as $R^1$ in formula (285) to (289).

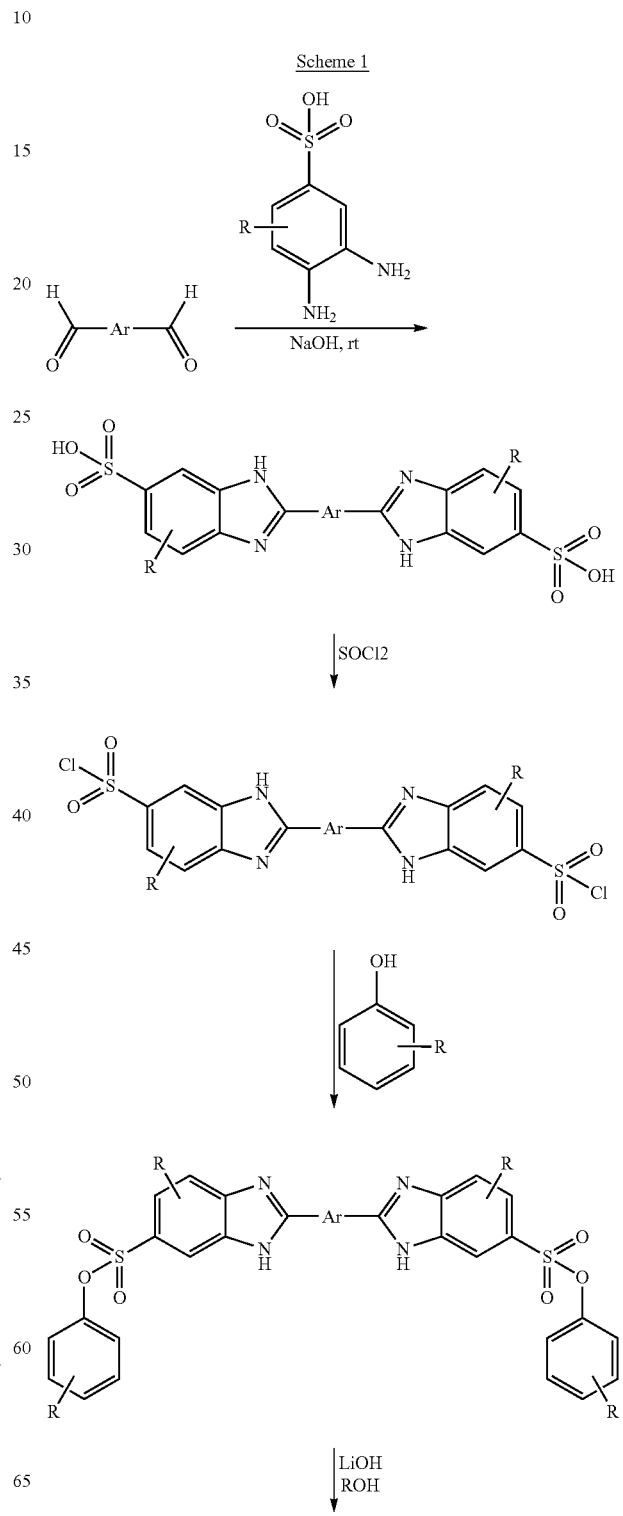

Scheme 1

137
-continued
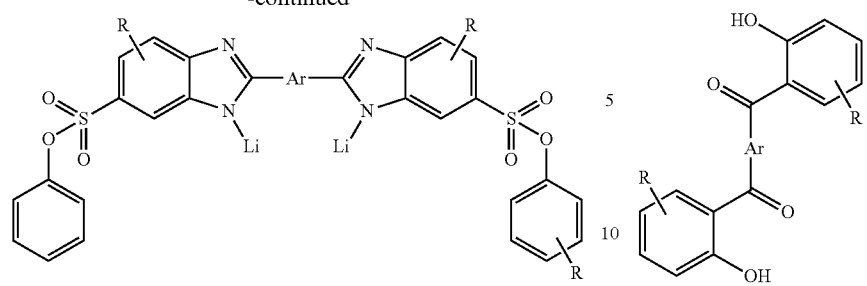
138
-continued
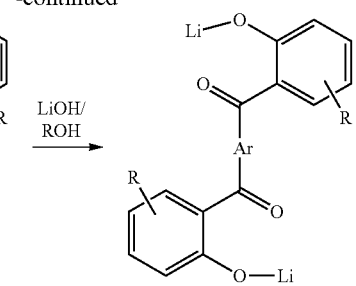
Scheme 2
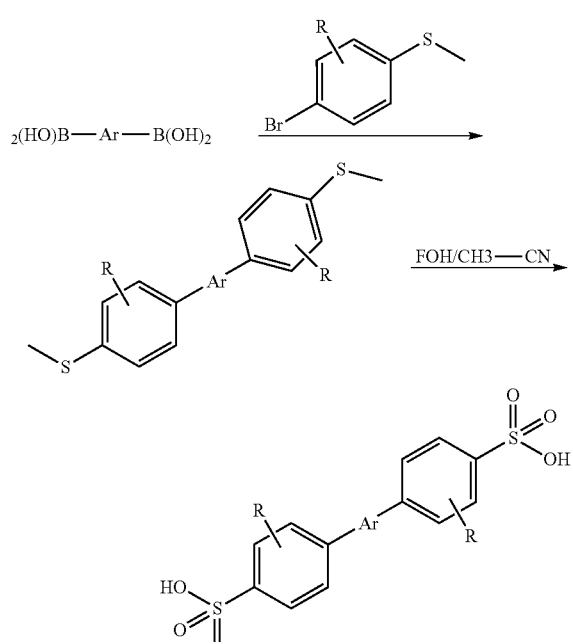
Scheme 3
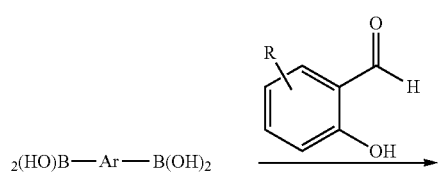
Scheme 4
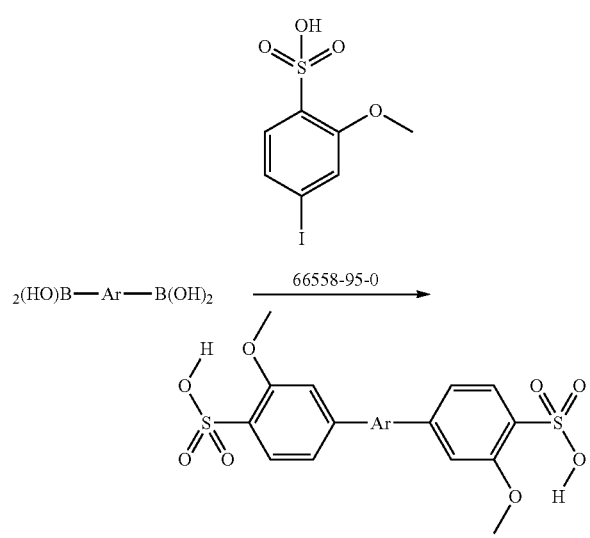
Scheme 5
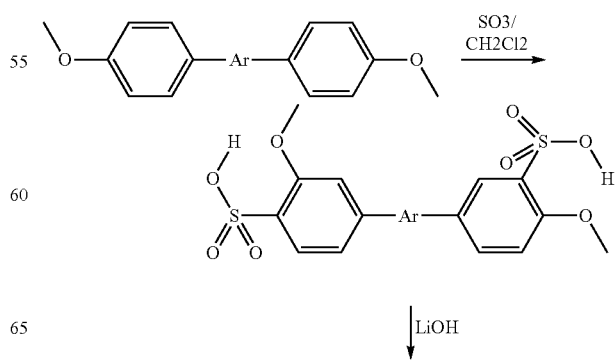

139

-continued

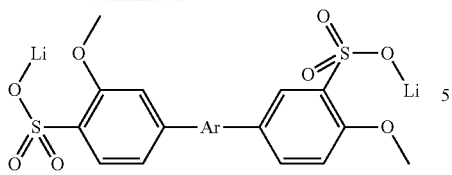

Scheme 6

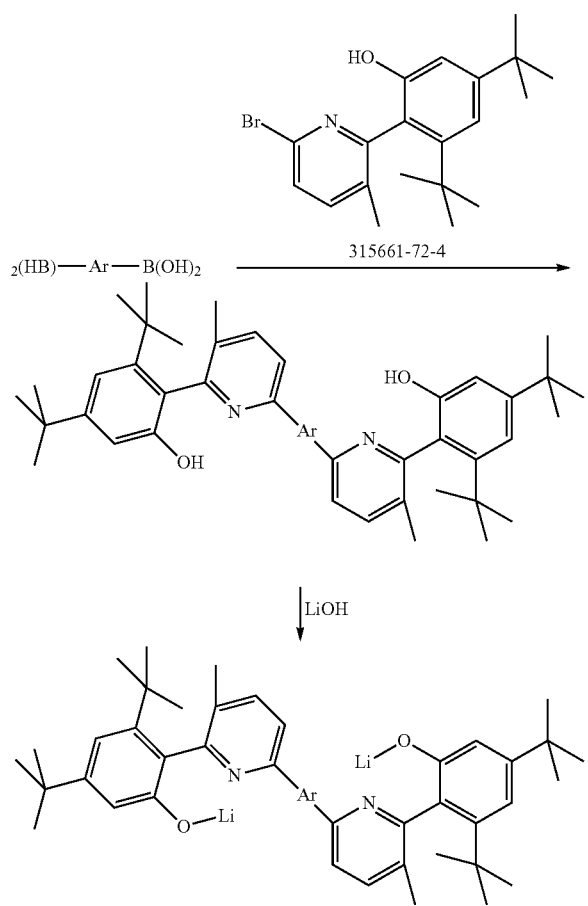

Scheme 7

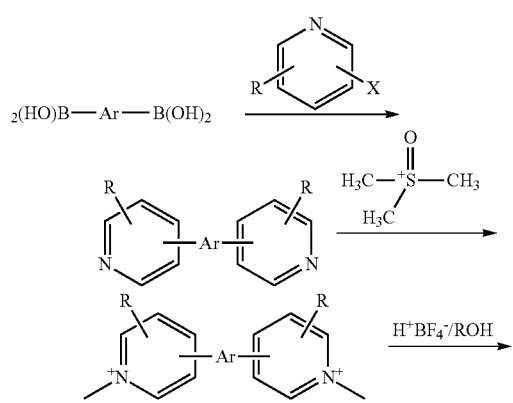

140

-continued

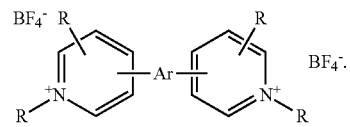

Scheme 8

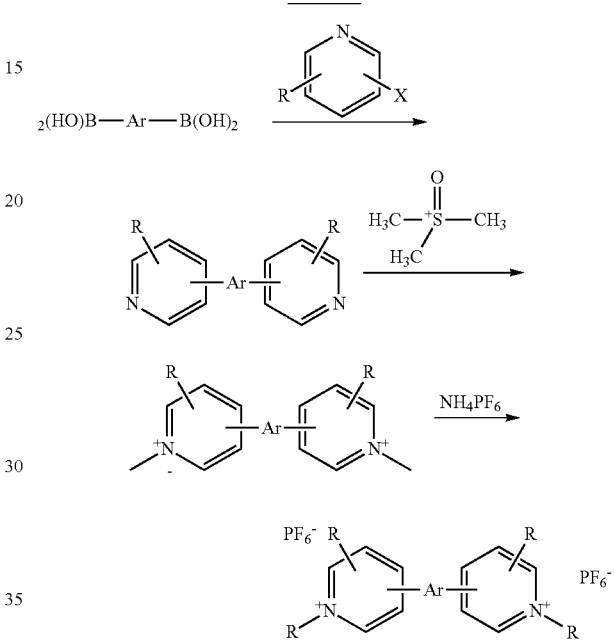

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

It will be appreciated that many of the features described above, particularly of the preferred embodiments, are inventive in their own right and not just as part of an embodiment of the present invention. Independent protection may be sought for these features in addition to or alternative to any invention presently claimed.

The teaching as disclosed here can be abstracted and combined with other examples disclosed.

Other features of the invention will become apparent in the course of the following description of exemplary embodiments, which are given for illustration of the invention and are not intended to be limiting thereof.

WORKING EXAMPLES

Example 1

Materials

TEG1 is a triplet green emitter, and synthesized according to WO 2004/026886.

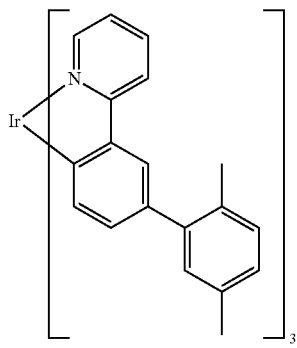

TMM1 is a triplet matrix material, which can be synthesized according to WO 2005/053055.

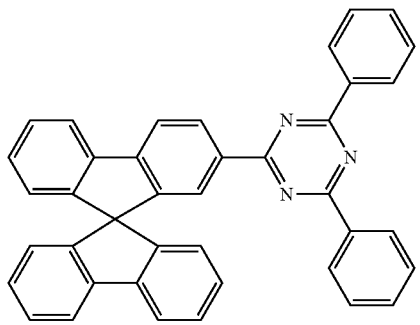 [SMILES: c1ccc(-c2nc(-c3ccccc3)nc(-c3ccc4c(c3)C3(c5ccccc5-c5ccccc53)c3ccccc3-4)n2)cc1]

TMM2 is wide-gap materials, used as triplet co-matrix material, which can be synthesized according to WO 2009124627.

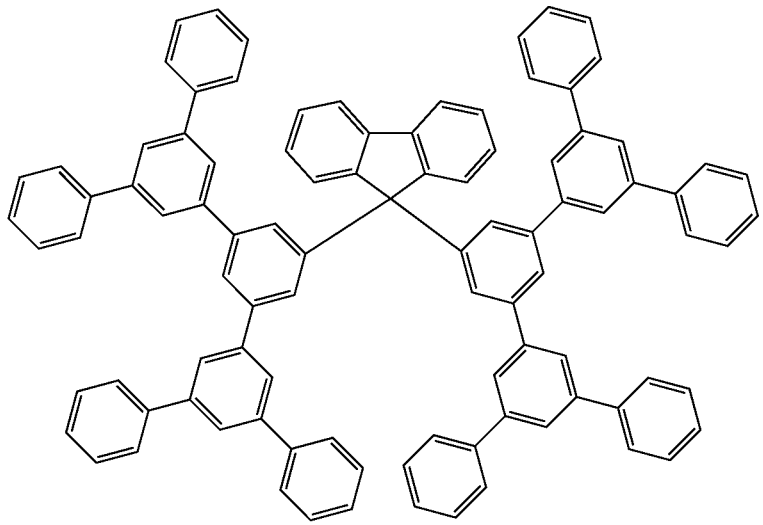 [SMILES: c1ccc(-c2cc(-c3ccccc3)cc(-c3cc(-c4cc(-c5ccccc5)cc(-c5ccccc5)c4)cc(C4(c5cc(-c6cc(-c7ccccc7)cc(-c7ccccc7)c6)cc(-c6cc(-c7ccccc7)cc(-c7ccccc7)c6)c5)c5ccccc5-c5ccccc54)c3)c2)cc1]

Poly(ethylene oxide) (PEO) is used as ion conducting material. PEO having a viscosity average molecular weight $M=1\times10^6$ can be purchased from Aldrich, and is used as received.

The first ionic material IM1, lithium trifluoromethanesulfonate ($LiCF_3SO_3$), can be purchased from Aldrich, and is used as received and as reference.

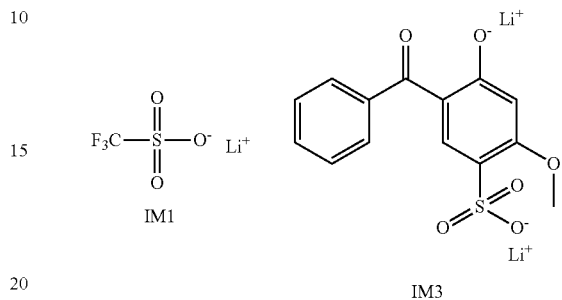

The second ionic material IM3 is a new double charged ionic compound according to the present invention, and can be synthesized as follows.

Example 2

Preparation of Dilithium Salt IM3

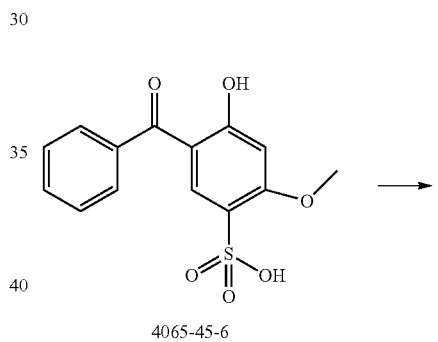

4065-45-6

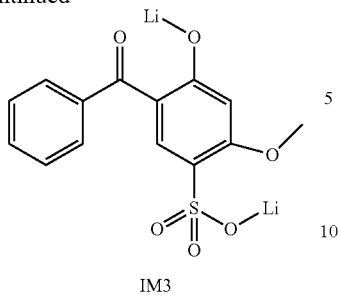

IM3

5-benzoyl-4-hydroxy-2-methoxy-benzenesulfonic acid (6 g, 19 mmol) is dissolved in 30 ml of ethanol and LiOH (0.98 g, 41 mmol) dissolved in 10 ml of ethanol is added. This resulting compound is re-crystallised in acetone. A white powder can be obtained by evaporation of the solvent and isolated by vacuum filtration. Yield 80%.

Example 3

Quantum Chemical Calculations on IM3 and its Precursors

Quantum simulations on organic non-ionic compounds are conducted employing Gaussian 03W software (Gaussian Inc.). For organic compound comprising no metal, at first a semi-empirical method "Ground State/Semi-empirical/Default Spin/AM1" (Charge 0/Spin Singlet) is used to optimise the molecular geometry, and then the energy is calculated by TD-DFT (time-dependent density functional theory) method "TD-SCF/DFT/Default Spin/B3PW91" with the basis set "6-31G(d)" (Charge 0/Spin Singlet). For metal complexes comprising transition metals (incl. lanthanide and actinide), the geometry optimisation is conducted using Hartree-Fock with Basis Set "LanL2 MB"; and the energy calculation is then conducted by using TD-DFT with correction functional B3PW91 and basis set 6-31G(d) for non-metal elements and Lanz2DZ (Los Alamos National Laboratory 2-double-z) for transition metals. A couple of data can be obtained by such calculations but one of the most important results provided by quantum chemical calculations in this field include HOMO/LUMO energy levels (highest occupied molecular orbital/lowest unoccupied molecular orbital), band gaps and energies for triplet and singlet excited states. Hereby, the first triplet (T1) and first singlet (S1) excited states are most important. From the energy calculation one gets HOMO HEh and LUMO LEh in Hartree units. And the HOMO and LUMO values in electron volts (eV) is determined with following equations, which can be derived from the calibration using Cyclovoltametry (CV) measurements.

$$HOMO(eV)=((HEh*27.212)-0.9899)/1.1206$$

$$LUMO(eV)=((LEh*27.212)-2.0041)/1.385$$

These values will be used as HOMO-LUMO levels of the compounds in the present invention. As an example, we obtain for the TMM1 (see also Table 1) from the calculation of a HOMO of −0.21292 Hartree and a LUMO of −0.06843 Hartree, which correspond a calibrated HOMO of −6.05 eV, and a calibrated LUMO of a calibrated −2.79 eV.

Instead of IM3, the precursor of IM3, Pre-IM3 is calculated

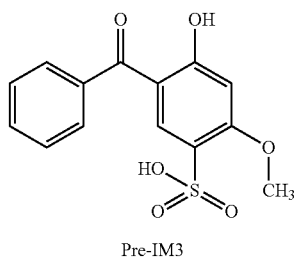 [SMILES: COc1cc(O)c(C(=O)c2ccccc2)cc1S(=O)(=O)O]

Pre-IM3

TABLE 1

Summary of energy levels of TMM1, TMM2, TEG1 and Pre-IM2

| Material | Homo Corr. [eV] | Lumo Corr. [eV] | Singulett S1 [eV] | Triplett T1 [eV] |
|---|---|---|---|---|
| TMM1 | −6.05 | −2.79 | 3.48 | 2.70 |
| TMM2 | −6.17 | −2.28 | 3.09 | 2.93 |
| TEG1 | −5.33 | −2.41 | 2.91 | 2.68 |
| Pre-IM3 | −6.83 | −2.81 | 3.52 | 2.89 |

Energy levels of TMM1, TMM2, TEG1 and Per-IM3 are summarized in Table 1. TMM1 and TMM2 both have a T1 higher that TEG1. Pre-IM2 has a T1 of 2.93 eV, which is suitable as a triplet matrix for TEG1, and a LUMO of −2.96 eV, which is good for electron transport. One skilled in the art will expect that IM3 has very similar electronic properties as Pre-IM3. Thus IM3 corresponds to an organic compound of formula (1), wherein M comprises an electron transport group and/or matrix group.

Example 4

Solutions 1 to 2

Two different solutions (formulations) comprising ionic compounds according to the invention (IM3) and a reference compound (IM1) are prepared employing standard techniques known to the person skilled in the art.
1. Preparation of a composition according to Table 2;
2. Preparation of solution 1 and 2 by dissolving the corresponding composition (see Table 2) in a mixed solvent of cyclohexanone and DMF in weight ratio of 1:1 with a concentration of 23 mg/ml;
3. Stirring the solutions in a glove box for 3 h;
4. The solutions are the filtered employing Millipore Millex LS, Hydrophobic PTFE 5.0 μm.

Both solutions can then be used to build an emissive layer in an electroluminescent device by coating, or to get mixed powders by evaporating the solvents for further use.

TABLE 2

Solutions with a concentration of 23 mg/ml

| | Composition for EML [wt %] |
|---|---|
| Solution 1 | TMM1(25%):TMM2(25%):TEG1(12%):IM1(15%):PEO(23%) |
| Solution 2 | TMM1(25%):TMM2(25%):TEG1(12%):IM3(15%):PEO(23%) |

Example 5

Preparation of OLEC1 and OLEC3

OLEC1 using IM1, and OLEC3 using IM3 in the emissive layer, in a sandwiched structure anode/PEDOT/Interlayer/EML/Cathode, are prepared according to the following steps:

1. PDEOT (Baytron P Al 4083) is deposited with a thickness of 80 nm onto ITO glass substrate (Technoprint Inc.) by spin coating and then heated for 10 min. at 120° C. in a clean room;
2. 20 nm Interlayer is deposited by spin coating from a toluene solution of HIL-012 (Merck KGaA) having a concentration of 0.5 wt %, and then heated at 180° C. for 60 min in a glove box;
3. The emissive layer is deposited by spin-coating the solution according to Example 4 yielding a layer with a thickness of 160 nm in the glove box;
4. The device is heated at 50° C. for 30 min. and then put in vacuum for 30 min to remove residual solvent;
5. An Al (150 nm) cathode is deposited by evaporation onto the emissive layer;
6. The device is encapsulated using a UV-cured resin, UV Resin T-470/UR7114 (Nagase Chemtex Corporation), and a glass cap.

In addition, an OLED device (OLED-Ref) is prepared as benchmark according to the following steps:

1. As step 1 for OLEC1;
2. As step 2 for OLEC1;
3. The emissive layer is deposited by spin-coating the solution of TMM1 (42 wt %):TMM2 (42 wt %):TEG1 (16 wt %) in toluene having a concentration of 24 mg/ml yielding a layer with a thickness of 80 nm in the glovebox;
4. The device is heated at 180° C. for 10 min. to remove residual solvent;
5. An Ba/Al (3 nm/150 nm) cathode is deposited by evaporation onto the emissive layer;
6. The device is encapsulated using a UV-cured resin, UV Resin T-470/UR7114 (Nagase Chemtex Corporation), and a glass cap

Example 6

Characterisation of OLEC1 and OLEC3

OLED-Ref, OLEC1 and OLEC3 are then characterized by employing standard techniques well known to one skilled in the art. The following properties are recorded: VIL characteristics, EL spectrum and color coordinates, efficiency, driving voltages.

The performance of OLECs and OLED-Ref is summarized in Table 3, wherein Uon stands for turn-on voltage, and U(100) for the voltage at 100 nits.

TABLE 3

|  | Max. Eff. | Uon | U (100) | CIE x | CIE y |
|---|---|---|---|---|---|
| OLEC1 | 4.3 | 5.5 | 8.4 | 0.36 | 0.60 |
| OLEC3 | 22.9 | 4.4 | 7.5 | 0.35 | 0.61 |
| OLED-Ref | 21.3 | 2.5 | 3.6 | 0.34 | 0.62 |

Both OLECs and OLED shows a similar color coordinates with only slight differences which might be due to cavity effect. As compared to OLEC1 with the reference ionic compound IM1, OLEC3, which comprises a new ionic compound according to the present invention, shows improved performance regarding efficiency and driving voltage.

Moreover, as compared to OLED-Ref, OLEC3 shows an improved efficiency. Even though the driving voltage of OLEC3 is higher than that of OLED-Ref the result is surprising for one skilled in that art, particularly if one considers that OLEC3 has an EML of 160 nm, and aluminium only as cathode.

Further improvement in performance can be achieved by different ways, for example by optimization of the concentration in the EML, the thickness of the EML and/or interlayer, and particularly by further exploiting the materials and the corresponding device disclosed in the present invention

The invention claimed is:

1. A composition comprising at least one non-polymeric organic ionic compound and at least one non-ionic organic functional compound, wherein the organic ionic compound is a compound of formula (1):

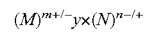  Formula (1);

wherein:
M is an organic ion having the charge m+ or m−;
N is an organic or inorganic counter ion being the same or different at each occurrence having the charge n− or n+;
m indicates the number of the charge of M and is an integer of ≥2;
y indicates the number of N, and is an integer of ≥1;
n indicates the number of the charge of N and is an integer of ≥1;
wherein the net charge of the compound of formula (1) is zero;
and wherein the non-ionic organic functional compound is selected from the group consisting of host materials, phosphorescent emitters, fluorescent emitters, hole transporting materials (HTM), hole injecting materials (HIM), electron transporting materials (ETM), and electron injecting materials (EIM).

2. The composition of claim 1, wherein the composition comprises a non-ionic fluorescent and/or phosphorescent emitter and a non-ionic host material.

3. The composition of claim 1, wherein $(M)^{m+/-}$ in the compound of formula (1) is a non-functional ion, i.e. is not a fluorescence or phosphorescence emitter, not a host, not a hole injecting material, not a hole transporting material, not an electron injecting material or not an electron transporting material.

4. The composition of claim 1, wherein $(M)^{m+/-}$ in the compound of formula (1) comprises an aliphatic hydrocarbyl group.

5. The composition of claim 1, wherein $(M)^{m+/-}$ comprises a functional organic group selected from a fluorescence emitting group, a host group, a hole injecting or transporting group, and an electron injecting or transporting group.

6. The composition of claim 1, wherein $(M)^{m+/-}$ has a molecular weight in the range from 6 to 1000 g/mol.

7. The composition of claim 1, wherein M is a cation and N is selected from $[HSO_4]^-$, $[SO_4]^{2-}$, $[NO_3]^-$, $[BF_4]^-$, $[(R_F)BF_3]^-$, $[(R_F)_2BF_2]^-$, $[(R_F)_3BF]^-$, $[(R_F)_4B]^-$, $[B(CN)_4]^-$, $[PO_4]^{3-}$, $[HPO_4]^{2-}$, $[H_2PO_4]^-$, $[Alkyl\text{-}OPO_3]^{2-}$, $[(Alkyl\text{-}O)_2PO_2]^-$, $[Alkyl\text{-}PO_3]^{2-}$, $[R_FPO_3]^{2-}$, $[(Alkyl)_2PO_2]^-$, $[(R_F)_2PO_2]^-$, $[R_FSO_3]^-$, $[HOSO_2(CF_2)_kSO_2O]^-$, $[OSO_2(CF_2)_kSO_2O]^{2-}$, $[Alkyl\text{-}SO_3]^-$, $[HOSO_2(CH_2)_kSO_2O]^-$, $[OSO_2(CH_2)_kSO_2O]^{2-}$, $[Alkyl\text{-}OSO_3]^-$, $[Alkyl\text{-}C$ (O)O]⁻, [HO(O)C(CH₂)ₖC(O)O]⁻, [R_FC(O)O]⁻, [HO(O)C(CF₂)ₖC(O)O]⁻, [O(O)C(CF₂)ₖC(O)O]²⁻, [(R_FSO₂)₂N]⁻, [(FSO₂)₂N]⁻, [((R_F)₂P(O))₂N]⁻, [(R_FSO₂)₃C]⁻, [(FSO₂)₃C]⁻, PF₆⁻, [PF₃(C₂F₅)₃]⁻, [PF₃(CF₃)₃]⁻, [B(COOCOO)₂⁻, [(CF₃SO₂)₂N]⁻, [(C₂F₅SO₂)₂N]⁻, [(CF₃SO₂)(C₄F₉SO₂)N]⁻, [(CN)₂N]⁻, [CF₃SO₂]₃C]⁻, and [(CN)₃C]⁻; wherein k is an integer from 1 to 8; R_F is a fluorinated aryl or alkyl-aryl or a fluorinated alkyl of formula (C_oF_{2o−x+1}H_x), wherein o is an integer from 1 to 12 and x is an integer of from 0 to 7.

8. The composition of claim 1, wherein M is an anion and N is selected from K⁺, Na⁺, Li⁺, ammonium-, phosphonium-, thiouronium-, thioxonium-, guanidinium-cations, heterocylic cations, and derivatives thereof.

9. The composition of claim 1, wherein m is 2 or 3, y is 3 or 2 and n is 2 or 1.

10. The composition of claim 1, wherein the composition further comprises at least one ion conductor compound.

11. The composition of claim 1, wherein the composition further comprises at least one dye.

12. A non-polymeric functional ionic organic compound selected from host materials, phosphorescent emitters, fluorescent emitters, hole transporting materials (HTM), hole injecting materials (HIM), electron transporting materials (ETM), and electron injecting materials (EIM), having a formula (1):

wherein

N is an organic or inorganic counter ion being the same or different at each occurrence having the charge n− or n+;

m indicates the number of the charge of M and is an integer of ≥2;

y indicates the number of N, and is an integer of ≥1;

n indicates the number of the charge of N and is an integer of ≥1;

(M)^{m+/−} comprises a functional organic group selected from a fluorescence emitting group, a host group, a hole injecting or transporting group, and an electron injecting or transporting group, and has a molecular weight in the range from 6 to 1000 g/mol;

wherein the molecular weight of the compound of formula (1) is below 1000 g/mol; and wherein the net charge of the compound of formula (1) is zero.

13. A formulation comprising:

the compound of claim 12 or a composition comprising at least one non-polymeric organic ionic compound and at least one non-ionic organic functional compound, wherein the organic ionic compound is a compound of formula (1):

wherein:

M is an organic ion having the charge m+ or m−;

N is an organic or inorganic counter ion being the same or different at each occurrence having the charge n− or n+;

m indicates the number of the charge of M and is an integer of ≥2;

y indicates the number of N, and is an integer of ≥1;

n indicates the number of the charge of N and is an integer of ≥1;

wherein the net charge of the compound of formula (1) is zero;

and wherein the non-ionic organic functional compound is selected from the group consisting of host materials, phosphorescent emitters, fluorescent emitters, hole transporting materials (HTM), hole injecting materials (HIM), electron transporting materials (ETM), and electron injecting materials (EIM);

and at least one solvent.

14. An electronic device comprising at least one compound according to claim 12 or a composition comprising at least one non-polymeric organic ionic compound and at least one non-ionic organic functional compound, wherein the organic ionic compound is a compound of formula (1):

wherein:

M is an organic ion having the charge m+ or m−;

N is an organic or inorganic counter ion being the same or different at each occurrence having the charge n− or n+;

m indicates the number of the charge of M and is an integer of ≥2;

y indicates the number of N, and is an integer of ≥1;

n indicates the number of the charge of N and is an integer of ≥1;

wherein the net charge of the compound of formula (1) is zero;

and wherein the non-ionic organic functional compound is selected from the group consisting of host materials, phosphorescent emitters, fluorescent emitters, hole transporting materials (HTM), hole injecting materials (HIM), electron transporting materials (ETM), and electron injecting materials (EIM).

15. The electronic device of claim 14, wherein the device is an organic electroluminescent device, or an organic sensor, or an organic solar cell.

16. The electronic device of claim 14, wherein the device is selected from organic light emitting diodes (OLED), polymer light emitting diodes (PLED), organic light emitting transistors (OLET), organic light emitting electrochemical cells (OLEC), organic light emitting electrochemical transistors (OLEETs), organic field effect transistors (OFET), thin film transistors (TFT), organic solar cells (O-SC), organic laser diodes (O-laser), organic integrated circuits (O-IC), radio frequency identification (RFID) tags, photodetector, sensors, logic circuits, memory elements, capacitor, charge injection layers, Schottky diodes, planarising layers, antistatic films, conducting substrates or patterns, photoconductors, electrophotographic elements, organic solar concentrator, organic spintronic devices, and organic plasmon emitting devices (OPEDs).

17. The electronic device of claim 14 selected from an organic light emitting diodes (OLED) or an organic light emitting electrochemical cells (OLEC), wherein the light emitted from the OLED or OLEC is adjusted for irradiation times, irradiation intensities and/or wavelength with a control unit.

18. A method of phototherapy comprising irradiating skin of a patient in need of phototherapy with an electronic device that includes at least one non-polymeric organic ionic compound and at least one non-ionic organic functional compound, wherein the organic ionic compound is a compound of formula (1):

wherein:

M is an organic ion having the charge m+ or m−;

N is an organic or inorganic counter ion being the same or different at each occurrence having the charge n− or n+;

m indicates the number of the charge of M and is an integer of ≥2;

y indicates the number of N, and is an integer of ≥1;

n indicates the number of the charge of N and is an integer of ≥1; and the net charge of the compound of formula (1) is zero; and wherein the non-ionic organic functional compound is selected from the group consisting of host materials, phosphorescent emitters, fluorescent emitters, hole transporting materials (HTM), hole injecting materials (HIM), electron transporting materials (ETM), and electron injecting materials (EIM); and wherein the electronic device is selected from an organic light emitting diodes (OLED) or an organic light emitting electrochemical cells (OLEC), and adjusting the light emitted from the OLED or OLEC by irradiation time, irradiation intensity and/or wavelength with a control unit.

19. The method of claim 18, wherein the electronic device is in a form article selected from plasters, pads, tapes, bandages, cuffs, blankets, caps, sleeping bags, textiles or stents.

20. The method of claim 19, wherein the form article is separable from the control unit, and the form article can be disposed of following the phototherapy.

* * * * *